US006797272B1

(12) United States Patent
Potter et al.

(10) Patent No.: US 6,797,272 B1
(45) Date of Patent: *Sep. 28, 2004

(54) ENHANCED IMMUNOGENICITY USING LEUKOTOXIN CHIMERAS

(75) Inventors: Andrew A. Potter, Saskatoon (CA); Mark J. Redmond, Saskatoon (CA); Huw P. A. Hughes, Saskatoon (CA)

(73) Assignee: University of Saskatchewan, Saskatchewan (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 38 days.

(21) Appl. No.: 08/976,566

(22) Filed: Nov. 24, 1997

Related U.S. Application Data

(63) Continuation of application No. 08/455,970, filed on May 31, 1995, now Pat. No. 5,708,155, which is a division of application No. 07/960,932, filed on Oct. 14, 1992, now Pat. No. 5,422,110, which is a continuation-in-part of application No. 07/779,171, filed on Oct. 16, 1991, now abandoned.

(51) Int. Cl.[7] .................................................. A61K 39/00

(52) U.S. Cl. ................................ 424/192.1; 424/255.1; 424/185.1; 424/193.1; 424/195.11; 424/236.1; 424/241.1; 530/350; 530/351

(58) Field of Search ........................... 424/192.1, 255.1, 424/185.1, 193.1, 195.11, 236.11, 241.1; 530/350, 351

(56) References Cited

U.S. PATENT DOCUMENTS

| | | | |
|---|---|---|---|
| 4,722,840 | A | 2/1988 | Valenzuela et al. |
| 4,867,973 | A | 9/1989 | Goers et al. |
| 4,957,739 | A | 9/1990 | Berget et al. |
| 4,975,420 | A | 12/1990 | Silversides et al. |
| 5,028,423 | A | 7/1991 | Prickett |
| 5,055,400 | A | 10/1991 | Lo et al. |
| 5,238,823 | A | 8/1993 | Potter et al. |
| 5,273,889 | A | 12/1993 | Potter et al. |
| 5,422,110 | A | 6/1995 | Potter et al. |
| 5,476,657 | A | 12/1995 | Potter |
| 5,594,107 | A | 1/1997 | Potter et al. |
| 5,708,155 | A | 1/1998 | Potter et al. |
| 5,723,129 | A | 3/1998 | Potter et al. |
| 5,837,268 | A | 11/1998 | Potter et al. |
| 5,969,126 | A | 10/1999 | Potter et al. |
| 6,022,960 | A | 2/2000 | Potter et al. |
| 6,521,746 | B1 | 2/2003 | Potter et al. |

FOREIGN PATENT DOCUMENTS

| | | |
|---|---|---|
| WO | WO 90/10458 | 9/1990 |
| WO | WO 91/15237 | 10/1991 |
| WO | WO 92/03558 | 3/1992 |

OTHER PUBLICATIONS

Adams et al., *J. Anim. Sci.* (1990) 68:1691–1698.
Adams et al., *J. Anim. Sci.* (1990) 68:2793–2802.
Bittle et al., *Nature* (1982) 298:30–33.
Bruggemann et al., *Bio Techniques* (1991) 10(2):202–209.
Burke et al., *Nature* (1988) 332:81–82.
Clarke et al., *Vaccines 88* Ginsberg, H., et al., Eds., (1988) pp. 127–131.
Delpeyroux et al., *Science* (1986) 233:472–475.
Forestier et al., *Infection and Immunity* (1991) 59(11):4212–4220.
Gentry et al., *Vet. Immunology and Immunopathology* (1985) 9:239–250.
Haynes et al., *Bio/Technology* (1986) 4:637–641.
Hughes et al., *Infection and Immunity* (1992) 10(2):545–570.
Jeffcoate et al., *Theriogenology* (1982) 18:65–77.
Kingsman et al., *Vaccine* (1988) 6:304–306.
Lo et al., *Infect. Immun.* (1985) 50(3):667–671.
Lowell et al., *Science* (1988) 240:800–802.
Morein et al., *Nature* (1984) 308:457–460.
Muller et al., *Proc. Natl. Acad. Sci.* (1982) 79:569–573.
Neurath et al., *Mol. Immunol.* (1989) 26(1):53–62.
Phalipon et al., *Gene* (1987) 55:255–263.
Que et al., *Infection and Immunity* (1988) 56(10):2645–2649.
Redmond et al., *Mol. Immunol.* (1991) 28(3):269–278.
Sad et al., *Immunology* (1991) 74:223–227.
Schutze et al., *J. Immunol.* (1985) 135(4):2319–2322.
Strathde et al., *Infect. Immun.* (1987) 55(12):3233–3236.
Valenzuela et al., *Bio/Technology* (1985) 3:323–326.

*Primary Examiner*—Jennifer E. Graser
(74) *Attorney, Agent, or Firm*—Robins & Pasternak LLP

(57) ABSTRACT

New immunological carrier systems, DNA encoding the same, and the use of these systems, are disclosed. The carrier systems include chimeric proteins which comprise a leukotoxin polypeptide fused to a selected antigen. The leukotoxin functions to increase the immunogenicity of the antigen fused thereto.

5 Claims, 45 Drawing Sheets

```
                640         650         660         670         680         690         700         710         720
                 .     .     .     .     .     .     .     .     .
GGG CTA TTA TCG GGC GCA ACA GCT GCA CTT GTA CAT GAT AAA AAT GCT TCA ACA GCT AAA AAA GTG GGT GCG GGT TTT GAA TTG GCA
CCC GAT AAT AGC CCG CGT TGT CGA CAT GAA CGT CTA TTT TTA CGA AGT TGT CAC CCA CGC CCA AAA CTT AAC CGT
Gly Leu Leu Ser Gly Ala Thr Ala Ala Leu Val His Asp Lys Asn Ala Ser Thr Ala Lys Lys Val Gly Ala Gly Phe Glu Leu Ala>
--c-----c-----c-----c-----c-----c-----c-----c-----c-----c-----c-----c---RECOMBINANT LEUKOTOXIN PEPTIDE-c

```
      910            920            930            940            950            960            970            980            990
       •              •              •              •              •              •              •              •              •
GAG AGT TAT GCC GAA CGC TTT AAA AAA TTA GGC TAT GAC GGA GAT AAT TTA TTA GCA GAA TAT CAG CGG GCC GGA ACA GGG ACT ATT GAT GCA
CTC TCA ATA CGG CTT GCG AAA TTT GCG CTT AAT CCG ATA CTG CCT ATA TTA AAT CGT CTT ATA GTC GCC CCT TGT TGA TAA CTA CGT
Glu Ser Tyr Ala Glu Arg Phe Lys Lys Leu Gly Tyr Asp Gly Asp Asn Leu Leu Ala Glu Tyr Gln Arg Ala Gly Thr Gly Thr Ile Asp Ala
---c---------c---------c---------c---------c---RECOMBINANT LEUKOTOXIN PEPTIDE_c---------c---------c---------c---------c---

```
                    2530.       2540.       2550.       2560.       2570.       2580.       2590.       2600.       2610.
AAT GGC GAG CGG ATC ACC TCA AAG CAA GTT GAT GAT CTA ATC GCA AAA GGT AAC TTG CCA TAG CGT TTT CCA TTG AAA ATT ACC CAA GAT GAG CTA GAT CTA TCA AAA GTT GTT
TTA CCG CTC GCC TAG TGG AGT TTC GTT CAA CTA CTA GAT TAG GAA TTG GGT CAA CAT TAA TGG GTT CTA GAT CTA AGT TTT CAA CAA
Asn Gly Arg Ile Thr Ser Lys Gln Val Asp Leu Ile Ala Lys Gly Asn Leu Ala       Ile Thr Gln Asp Glu Leu Asp Leu Ser Lys Val Val
---C---C---C---C---C---C---C---C---C-----RECOMBINANT LEUKOTOXIN PEPTIDE--

SRIF-1: 5'-GATCCAGCTCTTCTGCCGGCTGCAAAAACTTCTTCTGGAAAAACTTCACCAGCTGCTAGG-3'
SRIF-2: 3'-GTCGAGAAGACGGCCGACGTTTTTGAAGAAGACCTTTTGGAAGTGGTCGACGATCCCTAG-5'

GNRH-1: 5'-GATCTCAGCATTGGAGCTACGGCCTGCGCCCTGGCTAAG-3'
GNRH-2: 3'-AGTCGTAACCTCGATGCCGGACGCGGGACCGATTCCTAG-5'

VP4-1: 5'-GATCTTGCAACATTGTGCCTGTGAGCATTGTGTACACCCGGCGCAACCTAACCAAGACATTGTGTAG-3'
VP4-2: 3'-AACGTTGTAACACGGACACTCGTAACACATGTGGGCGGCGCGTTGAATTGGTTCTGTAACACATCCTAG-5'

FIG. 4

```
              10           20           30           40
               *            *            *            *            *
ATG GCT ACT GTT ATA GAT CTA AGC TTC CCA AAA ACT GGG GCA AAA AAA
TAC CGA TGA CAA TAT CTA GAT TCG AAG GGT TTT TGA CCC CGT TTT TTT
Met Ala Thr Val Ile Asp Leu Ser Phe Pro Lys Thr Gly Ala Lys Lys>
___a___a____RECOMBINANT LEUKOTOXIN PEPTIDE [SPLIT]_a___a___a___>

50           60           70           80           90
       *            *            *            *            *            *
ATT ATC CTC TAT ATT CCC CAA AAT TAC CAA TAT GAT ACT GAA CAA GGT
TAA TAG GAG ATA TAA GGG GTT TTA ATG GTT ATA CTA TGA CTT GTT CCA
Ile Ile Leu Tyr Ile Pro Gln Asn Tyr Gln Tyr Asp Thr Glu Gln Gly>
___a___a____RECOMBINANT LEUKOTOXIN PEPTIDE [SPLIT]_a___a___a___>

100          110          120          130          140
       *            *            *            *            *            *
AAT GGT TTA CAG GAT TTA GTC AAA GCG GCC GAA GAG TTG GGG ATT GAG
TTA CCA AAT GTC CTA AAT CAG TTT CGC CGG CTT CTC AAC CCC TAA CTC
Asn Gly Leu Gln Asp Leu Val Lys Ala Ala Glu Glu Leu Gly Ile Glu>
___a___a____RECOMBINANT LEUKOTOXIN PEPTIDE [SPLIT]_a___a___a___>

150          160          170          180          190
       *            *            *            *            *            *
GTA CAA AGA GAA GAA CGC AAT AAT ATT GCA ACA GCT CAA ACC AGT TTA
CAT GTT TCT CTT CTT GCG TTA TTA TAA CGT TGT CGA GTT TGG TCA AAT
Val Gln Arg Glu Glu Arg Asn Asn Ile Ala Thr Ala Gln Thr Ser Leu>
___a___a____RECOMBINANT LEUKOTOXIN PEPTIDE [SPLIT]_a___a___a___>

200          210          220          230          240
       *            *            *            *            *            *
GGC ACG ATT CAA ACC GCT ATT GGC TTA ACT GAG CGT GGC ATT GTG TTA
CCG TGC TAA GTT TGG CGA TAA CCG AAT TGA CTC GCA CCG TAA CAC AAT
Gly Thr Ile Gln Thr Ala Ile Gly Leu Thr Glu Arg Gly Ile Val Leu>
___a___a____RECOMBINANT LEUKOTOXIN PEPTIDE [SPLIT]_a___a___a___>
```

FIG. 6A

```
            250           260           270           280
       *     *     *     *     *     *     *     *     *
      TCC   GCT   CCA   CAA   ATT   GAT   AAA   TTG   CTA   CAG   AAA   ACT   AAA   GCA   GGC   CAA
      AGG   CGA   GGT   GTT   TAA   CTA   TTT   AAC   GAT   GTC   TTT   TGA   TTT   CGT   CCG   GTT
      Ser   Ala   Pro   Gln   Ile   Asp   Lys   Leu   Leu   Gln   Lys   Thr   Lys   Ala   Gly   Gln>
      ___a___a____RECOMBINANT LEUKOTOXIN PEPTIDE [SPLIT]_a___a___a___>

290           300           310           320           330
        *     *     *     *     *     *     *     *     *     *
      GCA   TTA   GGT   TCT   GCC   GAA   AGC   ATT   GTA   CAA   AAT   GCA   AAT   AAA   GCC   AAA
      CGT   AAT   CCA   AGA   CGG   CTT   TCG   TAA   CAT   GTT   TTA   CGT   TTA   TTT   CGG   TTT
      Ala   Leu   Gly   Ser   Ala   Glu   Ser   Ile   Val   Gln   Asn   Ala   Asn   Lys   Ala   Lys>
      ___a___a____RECOMBINANT LEUKOTOXIN PEPTIDE [SPLIT]_a___a___a___>

340           350           360           370           380
        *     *     *     *     *     *     *     *     *     *
      ACT   GTA   TTA   TCT   GGC   ATT   CAA   TCT   ATT   TTA   GGC   TCA   GTA   TTG   GCT   GGA
      TGA   CAT   AAT   AGA   CCG   TAA   GTT   AGA   TAA   AAT   CCG   AGT   CAT   AAC   CGA   CCT
      Thr   Val   Leu   Ser   Gly   Ile   Gln   Ser   Ile   Leu   Gly   Ser   Val   Leu   Ala   Gly>
      ___a___a____RECOMBINANT LEUKOTOXIN PEPTIDE [SPLIT]_a___a___a___>

390           400           410           420           430
   *    *     *     *     *     *     *     *     *     *     *
      ATG   GAT   TTA   GAT   GAG   GCC   TTA   CAG   AAT   AAC   AGC   AAC   CAA   CAT   GCT   CTT
      TAC   CTA   AAT   CTA   CTC   CGG   AAT   GTC   TTA   TTG   TCG   TTG   GTT   GTA   CGA   GAA
      Met   Asp   Leu   Asp   Glu   Ala   Leu   Gln   Asn   Asn   Ser   Asn   Gln   His   Ala   Leu>
      ___a___a____RECOMBINANT LEUKOTOXIN PEPTIDE [SPLIT]_a___a___a___>

440           450           460           470           480
        *     *     *     *     *     *     *     *     *     *
      GCT   AAA   GCT   GGC   TTG   GAG   CTA   ACA   AAT   TCA   TTA   ATT   GAA   AAT   ATT   GCT
      CGA   TTT   CGA   CCG   AAC   CTC   GAT   TGT   TTA   AGT   AAT   TAA   CTT   TTA   TAA   CGA
      Ala   Lys   Ala   Gly   Leu   Glu   Leu   Thr   Asn   Ser   Leu   Ile   Glu   Asn   Ile   Ala>
      ___a___a____RECOMBINANT LEUKOTOXIN PEPTIDE [SPLIT]_a___a___a___>

490           500           510           520
        *     *     *     *     *     *     *     *     *     *
      AAT   TCA   GTA   AAA   ACA   CTT   GAC   GAA   TTT   GGT   GAG   CAA   ATT   AGT   CAA   TTT
      TTA   AGT   CAT   TTT   TGT   GAA   CTG   CTT   AAA   CCA   CTC   GTT   TAA   TCA   GTT   AAA
      Asn   Ser   Val   Lys   Thr   Leu   Asp   Glu   Phe   Gly   Glu   Gln   Ile   Ser   Gln   Phe>
      ___a___a____RECOMBINANT LEUKOTOXIN PEPTIDE [SPLIT]_a___a___a___>
```

FIG. 6B

```
      530         540         550         560         570
       *           *           *           *           *
GGT TCA AAA CTA CAA AAT ATC AAA GGC TTA GGG ACT TTA GGA GAC AAA
CCA AGT TTT GAT GTT TTA TAG TTT CCG AAT CCC TGA AAT CCT CTG TTT
Gly Ser Lys Leu Gln Asn Ile Lys Gly Leu Gly Thr Leu Gly Asp Lys>
___a___a____RECOMBINANT LEUKOTOXIN PEPTIDE (SPLIT)_a___a___a___>

580         590         600         610         620
       *           *           *           *           *
CTC AAA AAT ATC GGT GGA CTT GAT AAA GCT GGC CTT GGT TTA GAT GTT
GAG TTT TTA TAG CCA CCT GAA CTA TTT CGA CCG GAA CCA AAT CTA CAA
Leu Lys Asn Ile Gly Gly Leu Asp Lys Ala Gly Leu Gly Leu Asp Val>
___a___a____RECOMBINANT LEUKOTOXIN PEPTIDE (SPLIT)_a___a___a___>

630         640         650         660         670
       *           *           *           *           *
ATC TCA GGG CTA TTA TCG GGC GCA ACA GCT GCA CTT GTA CTT GCA GAT
TAG AGT CCC GAT AAT AGC CCG CGT TGT CGA CGT GAA CAT GAA CGT CTA
Ile Ser Gly Leu Leu Ser Gly Ala Thr Ala Ala Leu Val Leu Ala Asp>
___a___a____RECOMBINANT LEUKOTOXIN PEPTIDE (SPLIT)_a___a___a___>

680         690         700         710         720
       *           *           *           *           *
AAA AAT GCT TCA ACA GCT AAA AAA GTG GGT GCG GGT TTT GAA TTG GCA
TTT TTA CGA AGT TGT CGA TTT TTT CAC CCA CGC CCA AAA CTT AAC CGT
Lys Asn Ala Ser Thr Ala Lys Lys Val Gly Ala Gly Phe Glu Leu Ala>
___a___a____RECOMBINANT LEUKOTOXIN PEPTIDE (SPLIT)_a___a___a___>

730         740         750         760
       *           *           *           *
AAC CAA GTT GTT GGT AAT ATT ACC AAA GCC GTT TCT TCT TAC ATT TTA
TTG GTT CAA CAA CCA TTA TAA TGG TTT CGG CAA AGA AGA ATG TAA AAT
Asn Gln Val Val Gly Asn Ile Thr Lys Ala Val Ser Ser Tyr Ile Leu>
___a___a____RECOMBINANT LEUKOTOXIN PEPTIDE (SPLIT)_a___a___a___>

770        780         790         800         810
  *          *           *           *           *
GCC CAA CGT GTT GCA GCA GGT TTA TCT TCA ACT GGG CCT GTG GCT GCT
CGG GTT GCA CAA CGT CGT CCA AAT AGA AGT TGA CCC GGA CAC CGA CGA
Ala Gln Arg Val Ala Ala Gly Leu Ser Ser Thr Gly Pro Val Ala Ala>
___a___a____RECOMBINANT LEUKOTOXIN PEPTIDE (SPLIT)_a___a___a___>

820        830         840         850         860
  *          *           *           *           *
TTA ATT GCT TCT ACT GTT TCT CTT GCG ATT AGC CCA TTA GCA TTT GCC
AAT TAA CGA AGA TGA CAA AGA GAA CGC TAA TCG GGT AAT CGT AAA CGG
Leu Ile Ala Ser Thr Val Ser Leu Ala Ile Ser Pro Leu Ala Phe Ala>
___a___a____RECOMBINANT LEUKOTOXIN PEPTIDE (SPLIT)_a___a___a___>
```

FIG. 6C

```
       870           880           890           900           910
  *     *     *     *     *     *     *     *     *     *
GGT ATT GCC GAT AAA TTT AAT CAT GCA AAA AGT TTA GAG AGT TAT GCC
CCA TAA CGG CTA TTT AAA TTA GTA CGT TTT TCA AAT CTC TCA ATA CGG
Gly Ile Ala Asp Lys Phe Asn His Ala Lys Ser Leu Glu Ser Tyr Ala>
___a___a____RECOMBINANT LEUKOTOXIN PEPTIDE [SPLIT]_a___a___a___>

920           930           940           950           960
  *     *     *     *     *     *     *     *     *     *
GAA CGC TTT AAA AAA TTA GGC TAT GAC GGA GAT AAT TTA TTA GCA GAA
CTT GCG AAA TTT TTT AAT CCG ATA CTG CCT CTA TTA AAT AAT CGT CTT
Glu Arg Phe Lys Lys Leu Gly Tyr Asp Gly Asp Asn Leu Leu Ala Glu>
___a___a____RECOMBINANT LEUKOTOXIN PEPTIDE [SPLIT]_a___a___a___>

970           980           990          1000
  *     *     *     *     *     *     *     *     *
TAT CAG CGG GGA ACA GGG ACT ATT GAT GCA TCG GTT ACT GCA ATT AAT
ATA GTC GCC CCT TGT CCC TGA TAA CTA CGT AGC CAA TGA CGT TAA TTA
Tyr Gln Arg Gly Thr Gly Thr Ile Asp Ala Ser Val Thr Ala Ile Asn>
___a___a____RECOMBINANT LEUKOTOXIN PEPTIDE [SPLIT]_a___a___a___>

1010          1020          1030          1040          1050
  *     *     *     *     *     *     *     *     *     *
ACC GCA TTG GCC GCT ATT GCT GGT GGT GTG TCT GCT GCT GCA GCC GGC
TGG CGT AAC CGG CGA TAA CGA CCA CCA CAC AGA CGA CGA CGT CGG CCG
Thr Ala Leu Ala Ala Ile Ala Gly Gly Val Ser Ala Ala Ala Ala Gly>
___a___a____RECOMBINANT LEUKOTOXIN PEPTIDE [SPLIT]_a___a___a___>

1060          1070          1080          1090          1100
  *     *     *     *     *     *     *     *     *     *
TCG GTT ATT GCT TCA CCG ATT GCC TTA TTA GTA TCT GGG ATT ACC GGT
AGC CAA TAA CGA AGT GGC TAA CGG AAT AAT CAT AGA CCC TAA TGG CCA
Ser Val Ile Ala Ser Pro Ile Ala Leu Leu Val Ser Gly Ile Thr Gly>
___a___a____RECOMBINANT LEUKOTOXIN PEPTIDE [SPLIT]_a___a___a___>

1110          1120          1130          1140          1150
  *     *     *     *     *     *     *     *     *     *
GTA ATT TCT ACG ATT CTG CAA TAT TCT AAA CAA GCA ATG TTT GAG CAC
CAT TAA AGA TGC TAA GAC GTT ATA AGA TTT GTT CGT TAC AAA CTC GTG
Val Ile Ser Thr Ile Leu Gln Tyr Ser Lys Gln Ala Met Phe Glu His>
___a___a____RECOMBINANT LEUKOTOXIN PEPTIDE [SPLIT]_a___a___a___>
```

FIG. 6D

```
        1160           1170           1180           1190           1200
         *      *      *      *       *      *      *      *       *      *
GTT GCA AAT AAA ATT CAT AAC AAA ATT GTA GAA TGG GAA AAA AAT AAT
CAA CGT TTA TTT TAA GTA TTG TTT TAA CAT CTT ACC CTT TTT TTA TTA
Val Ala Asn Lys Ile His Asn Lys Ile Val Glu Trp Glu Lys Asn Asn>
___a___a____RECOMBINANT LEUKOTOXIN PEPTIDE [SPLIT]_a___a___a___>

1210           1220           1230           1240
         *      *      *      *       *      *      *      *
CAC GGT AAG AAC TAC TTT GAA AAT GGT TAC GAT GCC CGT TAT CTT GCG
GTG CCA TTC TTG ATG AAA CTT TTA CCA ATG CTA CGG GCA ATA GAA CGC
His Gly Lys Asn Tyr Phe Glu Asn Gly Tyr Asp Ala Arg Tyr Leu Ala>
___a___a____RECOMBINANT LEUKOTOXIN PEPTIDE [SPLIT]_a___a___a___>

1250           1260           1270           1280           1290
    *      *      *      *       *      *      *      *       *      *
AAT TTA CAA GAT AAT ATG AAA TTC TTA CTG AAC TTA AAC AAA GAG TTA
TTA AAT GTT CTA TTA TAC TTT AAG AAT GAC TTG AAT TTG TTT CTC AAT
Asn Leu Gln Asp Asn Met Lys Phe Leu Leu Asn Leu Asn Lys Glu Leu>
___a___a____RECOMBINANT LEUKOTOXIN PEPTIDE [SPLIT]_a___a___a___>

1300           1310           1320           1330           1340
         *      *      *      *       *      *      *      *       *
CAG GCA GAA CGT GTC ATC GCT ATT ACT CAG CAG CAA TGG GAT AAC AAC
GTC CGT CTT GCA CAG TAG CGA TAA TGA GTC GTC GTT ACC CTA TTG TTG
Gln Ala Glu Arg Val Ile Ala Ile Thr Gln Gln Gln Trp Asp Asn Asn>
___a___a____RECOMBINANT LEUKOTOXIN PEPTIDE [SPLIT]_a___a___a___>

1350           1360           1370           1380           1390
         *      *      *      *       *      *      *      *       *      *
ATT GGT GAT TTA GCT GGT ATT AGC CGT TTA GGT GAA AAA GTC CTT AGT
TAA CCA CTA AAT CGA CCA TAA TCG GCA AAT CCA CTT TTT CAG GAA TCA
Ile Gly Asp Leu Ala Gly Ile Ser Arg Leu Gly Glu Lys Val Leu Ser>
___a___a____RECOMBINANT LEUKOTOXIN PEPTIDE [SPLIT]_a___a___a___>

1400           1410           1420           1430           1440
         *      *      *      *       *      *      *      *       *      *
GGT AAA GCC TAT GTG GAT GCG TTT GAA GAA GGC AAA CAC ATT AAA GCC
CCA TTT CGG ATA CAC CTA CGC AAA CTT CTT CCG TTT GTG TAA TTT CGG
Gly Lys Ala Tyr Val Asp Ala Phe Glu Glu Gly Lys His Ile Lys Ala>
___a___a____RECOMBINANT LEUKOTOXIN PEPTIDE [SPLIT]_a___a___a___>

1450           1460           1470           1480
         *      *      *      *       *      *      *      *
GAT AAA TTA GTA CAG TTG GAT TCG GCA AAC GGT ATT ATT GAT GTG AGT
CTA TTT AAT CAT GTC AAC CTA AGC CGT TTG CCA TAA TAA CTA CAC TCA
Asp Lys Leu Val Gln Leu Asp Ser Ala Asn Gly Ile Ile Asp Val Ser>
___a___a____RECOMBINANT LEUKOTOXIN PEPTIDE [SPLIT]_a___a___a___>
```

FIG. 6E

```
        1490          1500          1510          1520          1530
          *     *       *     *       *     *       *     *       *     *
   AAT TCG GGT AAA GCG AAA ACT CAG CAT ATC TTA TTC AGA ACG CCA TTA
   TTA AGC CCA TTT CGC TTT TGA GTC GTA TAG AAT AAG TCT TGC GGT AAT
   Asn Ser Gly Lys Ala Lys Thr Gln His Ile Leu Phe Arg Thr Pro Leu>
   ___a___a____RECOMBINANT LEUKOTOXIN PEPTIDE [SPLIT]_a___a___a___>

1540          1550          1560          1570          1580
          *     *       *     *       *     *       *     *       *     *
   TTG ACG CCG GGA ACA GAG CAT CGT GAA CGC GTA CAA ACA GGT AAA TAT
   AAC TGC GGC CCT TGT CTC GTA GCA CTT GCG CAT GTT TGT CCA TTT ATA
   Leu Thr Pro Gly Thr Glu His Arg Glu Arg Val Gln Thr Gly Lys Tyr>
   ___a___a____RECOMBINANT LEUKOTOXIN PEPTIDE [SPLIT]_a___a___a___>

1590          1600          1610          1620          1630
          *     *       *     *       *     *       *     *       *     *
   GAA TAT ATT ACC AAG CTC AAT ATT AAC CGT GTA GAT AGC TGG AAA ATT
   CTT ATA TAA TGG TTC GAG TTA TAA TTG GCA CAT CTA TCG ACC TTT TAA
   Glu Tyr Ile Thr Lys Leu Asn Ile Asn Arg Val Asp Ser Trp Lys Ile>
   ___a___a____RECOMBINANT LEUKOTOXIN PEPTIDE [SPLIT]_a___a___a___>

1640          1650          1660          1670          1680
          *     *       *     *       *     *       *     *       *     *
   ACA GAT GGT GCA GCA AGT TCT ACC TTT GAT TTA ACT AAC GTT GTT CAG
   TGT CTA CCA CGT CGT TCA AGA TGG AAA CTA AAT TGA TTG CAA CAA GTC
   Thr Asp Gly Ala Ala Ser Ser Thr Phe Asp Leu Thr Asn Val Val Gln>
   ___a___a____RECOMBINANT LEUKOTOXIN PEPTIDE [SPLIT]_a___a___a___>

1690          1700          1710          1720
          *     *       *     *       *     *       *     *
   CGT ATT GGT ATT GAA TTA GAC AAT GCT GGA AAT GTA ACT AAA ACC AAA
   GCA TAA CCA TAA CTT AAT CTG TTA CGA CCT TTA CAT TGA TTT TGG TTT
   Arg Ile Gly Ile Glu Leu Asp Asn Ala Gly Asn Val Thr Lys Thr Lys>
   ___a___a____RECOMBINANT LEUKOTOXIN PEPTIDE [SPLIT]_a___a___a___>

1730          1740          1750          1760          1770
    *     *       *     *       *     *       *     *       *     *
   GAA ACA AAA ATT ATT GCC AAA CTT GGT GAA GGT GAT GAC AAC GTA TTT
   CTT TGT TTT TAA TAA CGG TTT GAA CCA CTT CCA CTA CTG TTG CAT AAA
   Glu Thr Lys Ile Ile Ala Lys Leu Gly Glu Gly Asp Asp Asn Val Phe>
   ___a___a____RECOMBINANT LEUKOTOXIN PEPTIDE [SPLIT]_a___a___a___>
```

FIG. 6F

```
        1780            1790            1800            1810            1820
         *       *       *       *       *       *       *       *       *       *
        GTT GGT TCT GGT ACG ACG GAA ATT GAT GGC GGT GAA GGT TAC GAC CGA
        CAA CCA AGA CCA TGC TGC CTT TAA CTA CCG CCA CTT CCA ATG CTG GCT
        Val Gly Ser Gly Thr Thr Glu Ile Asp Gly Gly Glu Gly Tyr Asp Arg>
        ___a___a____RECOMBINANT LEUKOTOXIN PEPTIDE [SPLIT]_a___a___a___>

1830            1840            1850            1860            1870
         *       *       *       *       *       *       *       *       *       *
        GTT CAC TAT AGC CGT GGA AAC TAT GGT GCT TTA ACT ATT GAT GCA ACC
        CAA GTG ATA TCG GCA CCT TTG ATA CCA CGA AAT TGA TAA CTA CGT TGG
        Val His Tyr Ser Arg Gly Asn Tyr Gly Ala Leu Thr Ile Asp Ala Thr>
        ___a___a____RECOMBINANT LEUKOTOXIN PEPTIDE [SPLIT]_a___a___a___>

1880            1890            1900            1910            1920
             *       *       *       *       *       *       *       *       *       *
            AAA GAG ACC GAG CAA GGT AGT TAT ACC GTA AAT CGT TTC GTA GAA ACC
            TTT CTC TGG CTC GTT CCA TCA ATA TGG CAT TTA GCA AAG CAT CTT TGG
            Lys Glu Thr Glu Gln Gly Ser Tyr Thr Val Asn Arg Phe Val Glu Thr>
            ___a___a____RECOMBINANT LEUKOTOXIN PEPTIDE [SPLIT]_a___a___a___>

1930            1940            1950            1960
                 *       *       *       *       *       *       *       *       *       *
                GGT AAA GCA CTA CAC GAA GTG ACT TCA ACC CAT ACC GCA TTA GTG GGC
                CCA TTT CGT GAT GTG CTT CAC TGA AGT TGG GTA TGG CGT AAT CAC CCG
                Gly Lys Ala Leu His Glu Val Thr Ser Thr His Thr Ala Leu Val Gly>
                ___a___a____RECOMBINANT LEUKOTOXIN PEPTIDE [SPLIT]_a___a___a___>

1970            1980            1990            2000            2010
         *       *       *       *       *       *       *       *       *       *
        AAC CGT GAA GAA AAA ATA GAA TAT CGT CAT AGC AAT AAC CAG CAC CAT
        TTG GCA CTT CTT TTT TAT CTT ATA GCA GTA TCG TTA TTG GTC GTG GTA
        Asn Arg Glu Glu Lys Ile Glu Tyr Arg His Ser Asn Asn Gln His His>
        ___a___a____RECOMBINANT LEUKOTOXIN PEPTIDE [SPLIT]_a___a___a___>

2020            2030            2040            2050            2060
             *       *       *       *       *       *       *       *       *       *
            GCC GGT TAT TAC ACC AAA GAT ACC TTG AAA GCT GTT GAA GAA ATT ATC
            CGG CCA ATA ATG TGG TTT CTA TGG AAC TTT CGA CAA CTT CTT TAA TAG
            Ala Gly Tyr Tyr Thr Lys Asp Thr Leu Lys Ala Val Glu Glu Ile Ile>
            ___a___a____RECOMBINANT LEUKOTOXIN PEPTIDE [SPLIT]_a___a___a___>

2070            2080            2090            2100            2110
         *       *       *       *       *       *       *       *       *       *
        GGT ACA TCA CAT AAC GAT ATC TTT AAA GGT AGT AAG TTC AAT GAT GCC
        CCA TGT AGT GTA TTG CTA TAG AAA TTT CCA TCA TTC AAG TTA CTA CGG
        Gly Thr Ser His Asn Asp Ile Phe Lys Gly Ser Lys Phe Asn Asp Ala>
        ___a___a____RECOMBINANT LEUKOTOXIN PEPTIDE [SPLIT]_a___a___a___>
```

FIG. 6G

```
        2120         2130         2140         2150         2160
     *    *       *    *       *    *       *    *       *    *
    TTT  AAC  GGT  GGT  GAT  GGT  GTC  GAT  ACT  ATT  GAC  GGT  AAC  GAC  GGC  AAT
    AAA  TTG  CCA  CCA  CTA  CCA  CAG  CTA  TGA  TAA  CTG  CCA  TTG  CTG  CCG  TTA
    Phe  Asn  Gly  Gly  Asp  Gly  Val  Asp  Thr  Ile  Asp  Gly  Asn  Asp  Gly  Asn>
    ___a___a___RECOMBINANT  LEUKOTOXIN  PEPTIDE  [SPLIT]_a___a___a___>

2170         2180         2190         2200
       *    *       *    *       *    *       *    *       *
      GAC  CGC  TTA  TTT  GGT  GGT  AAA  GGC  GAT  GAT  ATT  CTC  GAT  GGT  GGA  AAT
      CTG  GCG  AAT  AAA  CCA  CCA  TTT  CCG  CTA  CTA  TAA  GAG  CTA  CCA  CCT  TTA
      Asp  Arg  Leu  Phe  Gly  Gly  Lys  Gly  Asp  Asp  Ile  Leu  Asp  Gly  Gly  Asn>
      ___a___a___RECOMBINANT  LEUKOTOXIN  PEPTIDE  [SPLIT]_a___a___a___>

2210         2220         2230         2240         2250
   *    *       *    *       *    *       *    *       *    *
  GGT  GAT  GAT  TTT  ATC  GAT  GGC  GGT  AAA  GGC  AAC  GAC  CTA  TTA  CAC  GGT
  CCA  CTA  CTA  AAA  TAG  CTA  CCG  CCA  TTT  CCG  TTG  CTG  GAT  AAT  GTG  CCA
  Gly  Asp  Asp  Phe  Ile  Asp  Gly  Gly  Lys  Gly  Asn  Asp  Leu  Leu  His  Gly>
  ___a___a___RECOMBINANT  LEUKOTOXIN  PEPTIDE  [SPLIT]_a___a___a___>

2260         2270         2280         2290         2300
       *    *       *    *       *    *       *    *       *    *
      GGC  AAG  GGC  GAT  GAT  ATT  TTC  GTT  CAC  CGT  AAA  GGC  GAT  GGT  AAT  GAT
      CCG  TTC  CCG  CTA  CTA  TAA  AAG  CAA  GTG  GCA  TTT  CCG  CTA  CCA  TTA  CTA
      Gly  Lys  Gly  Asp  Asp  Ile  Phe  Val  His  Arg  Lys  Gly  Asp  Gly  Asn  Asp>
      ___a___a___RECOMBINANT  LEUKOTOXIN  PEPTIDE  [SPLIT]_a___a___a___>

2310         2320         2330         2340         2350
       *    *       *    *       *    *       *    *       *    *
      ATT  ATT  ACC  GAT  TCT  GAC  GGC  AAT  GAT  AAA  TTA  TCA  TTC  TCT  GAT  TCG
      TAA  TAA  TGG  CTA  AGA  CTG  CCG  TTA  CTA  TTT  AAT  AGT  AAG  AGA  CTA  AGC
      Ile  Ile  Thr  Asp  Ser  Asp  Gly  Asn  Asp  Lys  Leu  Ser  Phe  Ser  Asp  Ser>
      ___a___a___RECOMBINANT  LEUKOTOXIN  PEPTIDE  [SPLIT]_a___a___a___>

2360         2370         2380         2390         2400
       *    *       *    *       *    *       *    *       *    *
      AAC  TTA  AAA  GAT  TTA  ACA  TTT  GAA  AAA  GTT  AAA  CAT  AAT  CTT  GTC  ATC
      TTG  AAT  TTT  CTA  AAT  TGT  AAA  CTT  TTT  CAA  TTT  GTA  TTA  GAA  CAG  TAG
      Asn  Leu  Lys  Asp  Leu  Thr  Phe  Glu  Lys  Val  Lys  His  Asn  Leu  Val  Ile>
      ___a___a___RECOMBINANT  LEUKOTOXIN  PEPTIDE  [SPLIT]_a___a___a___>
```

FIG. 6H

```
         2410           2420           2430           2440
    *      *       *      *       *      *       *      *
ACG AAT AGC AAA AAA GAG AAA GTG ACC ATT CAA AAC TGG TTC CGA GAG
TGC TTA TCG TTT TTT CTC TTT CAC TGG TAA GTT TTG ACC AAG GCT CTC
Thr Asn Ser Lys Lys Glu Lys Val Thr Ile Gln Asn Trp Phe Arg Glu>
___a___a____RECOMBINANT LEUKOTOXIN PEPTIDE [SPLIT]_a___a___a___>

2450           2460           2470           2480           2490
  *      *       *      *       *      *       *      *       *      *
GCT GAT TTT GCT AAA GAA GTG CCT AAT TAT AAA GCA ACT AAA GAT GAG
CGA CTA AAA CGA TTT CTT CAC GGA TTA ATA TTT CGT TGA TTT CTA CTC
Ala Asp Phe Ala Lys Glu Val Pro Asn Tyr Lys Ala Thr Lys Asp Glu>
___a___a____RECOMBINANT LEUKOTOXIN PEPTIDE [SPLIT]_a___a___a___>

2500           2510           2520           2530           2540
  *      *       *      *       *      *       *      *       *
AAA ATC GAA GAA ATC ATC GGT CAA AAT GGC GAG CGG ATC ACC TCA AAG
TTT TAG CTT CTT TAG TAG CCA GTT TTA CCG CTC GCC TAG TGG AGT TTC
Lys Ile Glu Glu Ile Ile Gly Gln Asn Gly Glu Arg Ile Thr Ser Lys>
___a___a____RECOMBINANT LEUKOTOXIN PEPTIDE [SPLIT]_a___a___a___>

2550           2560           2570           2580           2590
    *      *       *      *       *      *       *      *       *      *
CAA GTT GAT GAT CTT ATC GCA AAA GGT AAC GGC AAA ATT ACC CAA GAT
GTT CAA CTA CTA GAA TAG CGT TTT CCA TTG CCG TTT TAA TGG GTT CTA
Gln Val Asp Asp Leu Ile Ala Lys Gly Asn Gly Lys Ile Thr Gln Asp>
___a___a____RECOMBINANT LEUKOTOXIN PEPTIDE [SPLIT]_a___a___a___>

2600           2610           2620           2630           2640
    *      *       *      *       *      *       *      *       *      *
GAG CTA TCA AAA GTT GTT GAT AAC TAT GAA TTG CTC AAA CAT AGC AAA
CTC GAT AGT TTT CAA CAA CTA TTG ATA CTT AAC GAG TTT GTA TCG TTT
Glu Leu Ser Lys Val Val Asp Asn Tyr Glu Leu Leu Lys His Ser Lys>
___a___a____RECOMBINANT LEUKOTOXIN PEPTIDE [SPLIT]_a___a___a___>

2650           2660           2670           2680
    *      *       *      *       *      *       *      *
AAT GTG ACA AAC AGC TTA GAT AAG TTA ATC TCA TCT GTA AGT GCA TTT
TTA CAC TGT TTG TCG AAT CTA TTC AAT TAG AGT AGA CAT TCA CGT AAA
Asn Val Thr Asn Ser Leu Asp Lys Leu Ile Ser Ser Val Ser Ala Phe>
___a___a____RECOMBINANT LEUKOTOXIN PEPTIDE [SPLIT]_a___a___a___>

2690           2700           2710           2720           2730
  *      *       *      *       *      *       *      *       *      *
ACC TCG TCT AAT GAT TCG AGA AAT GTA TTA GTG GCT CCA ACT TCA ATG
TGG AGC AGA TTA CTA AGC TCT TTA CAT AAT CAC CGA GGT TGA AGT TAC
Thr Ser Ser Asn Asp Ser Arg Asn Val Leu Val Ala Pro Thr Ser M t>
___a___a____RECOMBINANT LEUKOTOXIN PEPTIDE [SPLIT]_a___a___a___>
```

FIG. 6I

```
       2740          2750          2760          2770          2780
   *      *      *      *      *      *      *      *      *      *
TTG GAT CAA AGT TTA TCT TCT CTT CAA TTT GCT AGG GGA TCC AGC TCT
AAC CTA GTT TCA AAT AGA AGA GAA GTT AAA CGA TCC CCT AGG TCG AGA
Leu Asp Gln Ser Leu Ser Ser Leu Gln Phe Ala Arg Gly Ser>
___a____RECOMBINANT LEUKOTOXIN PEPTIDE [SPLIT]_a___a___>
                                                            Ser Ser>
                                                            ___b___>

2790          2800          2810          2820          2830
   *      *      *      *      *      *      *      *      *      *
TCT GCC GGC TGC AAA AAC TTC TTC TGG AAA ACC TTC ACC AGC TGC TAG
AGA CGG CCG ACG TTT TTG AAG AAG ACC TTT TGG AAG TGG TCG ACG ATC
Ser>
___>
    Ala Gly Cys Lys Asn Phe Phe Trp Lys Thr Phe Thr Ser Cys End>
    ___c___c___c___c___c___SRIF PEPTIDE___c___c___c___c___c___>

*
GGATCC
CCTAGG
```

FIG. 6J

```
              10            20            30            40
         *    *        *    *        *    *        *    *        *
ATG GCT ACT GTT ATA GAT CTA AGC TTC CCA AAA ACT GGG GCA AAA AAA
TAC CGA TGA CAA TAT CTA GAT TCG AAG GGT TTT TGA CCC CGT TTT TTT
Met Ala Thr Val Ile Asp Leu Ser Phe Pro Lys Thr Gly Ala Lys Lys>
___b___b____RECOMBINANT LEUKOTOXIN PEPTIDE [SPLIT]_b___b___b___>

50            60            70            80            90
    *        *    *        *    *        *    *        *    *        *
ATT ATC CTC TAT ATT CCC CAA AAT TAC CAA TAT GAT ACT GAA CAA GGT
TAA TAG GAG ATA TAA GGG GTT TTA ATG GTT ATA CTA TGA CTT GTT CCA
Ile Ile Leu Tyr Ile Pro Gln Asn Tyr Gln Tyr Asp Thr Glu Gln Gly>
___b___b____RECOMBINANT LEUKOTOXIN PEPTIDE [SPLIT]_b___b___b___>

100           110           120           130           140
         *    *        *    *        *    *        *    *        *
AAT GGT TTA CAG GAT TTA GTC AAA GCG GCC GAA GAG TTG GGG ATT GAG
TTA CCA AAT GTC CTA AAT CAG TTT CGC CGG CTT CTC AAC CCC TAA CTC
Asn Gly Leu Gln Asp Leu Val Lys Ala Ala Glu Glu Leu Gly Ile Glu>
___b___b____RECOMBINANT LEUKOTOXIN PEPTIDE [SPLIT]_b___b___b___>

150           160           170           180           190
    *        *    *        *    *        *    *        *    *        *
GTA CAA AGA GAA GAA CGC AAT AAT ATT GCA ACA GCT CAA ACC AGT TTA
CAT GTT TCT CTT CTT GCG TTA TTA TAA CGT TGT CGA GTT TGG TCA AAT
Val Gln Arg Glu Glu Arg Asn Asn Ile Ala Thr Ala Gln Thr Ser Leu>
___b___b____RECOMBINANT LEUKOTOXIN PEPTIDE [SPLIT]_b___b___b___>

200           210           220           230           240
    *        *    *        *    *        *    *        *    *        *
GGC ACG ATT CAA ACC GCT ATT GGC TTA ACT GAG CGT GGC ATT GTG TTA
CCG TGC TAA GTT TGG CGA TAA CCG AAT TGA CTC GCA CCG TAA CAC AAT
Gly Thr Ile Gln Thr Ala Ile Gly Leu Thr Glu Arg Gly Ile Val Leu>
___b___b____RECOMBINANT LEUKOTOXIN PEPTIDE [SPLIT]_b___b___b___>
```

FIG. 8A

```
           250          260         270         280
            *    *       *    *      *     *    *     *
    TCC GCT CCA CAA ATT GAT AAA TTG CTA CAG AAA ACT AAA GCA GGC CAA
    AGG CGA GGT GTT TAA CTA TTT AAC GAT GTC TTT TGA TTT CGT CCG GTT
    Ser Ala Pro Gln Ile Asp Lys Leu Leu Gln Lys Thr Lys Ala Gly Gln>
    ___b___b____RECOMBINANT LEUKOTOXIN PEPTIDE [SPLIT]_b___b___b___>

290         300         310         320         330
      *    *      *     *     *     *     *     *     *     *
    GCA TTA GGT TCT GCC GAA AGC ATT GTA CAA AAT GCA AAT AAA GCC AAA
    CGT AAT CCA AGA CGG CTT TCG TAA CAT GTT TTA CGT TTA TTT CGG TTT
    Ala Leu Gly Ser Ala Glu Ser Ile Val Gln Asn Ala Asn Lys Ala Lys>
    ___b___b____RECOMBINANT LEUKOTOXIN PEPTIDE [SPLIT]_b___b___b___>

340         350         360         370         380
       *    *      *     *     *     *     *     *    *
    ACT GTA TTA TCT GGC ATT CAA TCT ATT TTA GGC TCA GTA TTG GCT GGA
    TGA CAT AAT AGA CCG TAA GTT AGA TAA AAT CCG AGT CAT AAC CGA CCT
    Thr Val Leu Ser Gly Ile Gln Ser Ile Leu Gly Ser Val Leu Ala Gly>
    ___b___b____RECOMBINANT LEUKOTOXIN PEPTIDE [SPLIT]_b___b___b___>

390         400         410         420         430
       *    *      *     *     *     *     *     *     *     *
    ATG GAT TTA GAT GAG GCC TTA CAG AAT AAC AGC AAC CAA CAT GCT CTT
    TAC CTA AAT CTA CTC CGG AAT GTC TTA TTG TCG TTG GTT GTA CGA GAA
    Met Asp Leu Asp Glu Ala Leu Gln Asn Asn Ser Asn Gln His Ala Leu>
    ___b___b____RECOMBINANT LEUKOTOXIN PEPTIDE [SPLIT]_b___b___b___>

440         450         460         470         480
           *    *      *     *     *     *     *     *     *     *
    GCT AAA GCT GGC TTG GAG CTA ACA AAT TCA TTA ATT GAA AAT ATT GCT
    CGA TTT CGA CCG AAC CTC GAT TGT TTA AGT AAT TAA CTT TTA TAA CGA
    Ala Lys Ala Gly Leu Glu Leu Thr Asn Ser Leu Ile Glu Asn Ile Ala>
    ___b___b____RECOMBINANT LEUKOTOXIN PEPTIDE [SPLIT]_b___b___b___>

490         500         510         520
          *    *      *     *     *     *     *     *     *
    AAT TCA GTA AAA ACA CTT GAC GAA TTN -GT GAG CAA ATT AGT CAA TTT
    TTA AGT CAT TTT TGT GAA CTG CTT AAN -CA CTC GTT TAA TCA GTT AAA
    Asn Ser Val Lys Thr Leu Asp Glu Xxx Cys Glu Gln Ile Ser Gln Phe>
    ___b___b____RECOMBINANT LEUKOTOXIN PEPTIDE [SPLIT]_b___b___b___>

530         540         550         560         570
     *    *      *     *     *     *     *     *     *     *
    GGT TCA AAA CTA CAA AAT ATC AAA GGC TTA GGG ACT TTA GGA GAC AAA
    CCA AGT TTT GAT GTT TTA TAG TTT CCG AAT CCC TGA AAT CCT CTG TTT
    Gly Ser Lys Leu Gln Asn Ile Lys Gly Leu Gly Thr Leu Gly Asp Lys>
    ___b___b____RECOMBINANT LEUKOTOXIN PEPTIDE [SPLIT]_b___b___b___>
```

FIG. 8B

```
        580           590           600           610           620
         *             *             *             *             *
CTC AAA AAT ATC GGT GGA CTT GAT AAA GCT GGC CTT GGT TTA GAT GTT
GAG TTT TTA TAG CCA CCT GAA CTA TTT CGA CCG GAA CCA AAT CTA CAA
Leu Lys Asn Ile Gly Gly Leu Asp Lys Ala Gly Leu Gly Leu Asp Val>
 __b___b____RECOMBINANT LEUKOTOXIN PEPTIDE [SPLIT]_b___b___b___>

630           640           650           660           670
         *             *             *             *             *
ATC TCA GGG CTA TTA TCG GGC GCA ACA GCT GCA CTT GTA CTT GCA GAT
TAG AGT CCC GAT AAT AGC CCG CGT TGT CGA CGT GAA CAT GAA CGT CTA
Ile Ser Gly Leu Leu Ser Gly Ala Thr Ala Ala Leu Val Leu Ala Asp>
 __b___b____RECOMBINANT LEUKOTOXIN PEPTIDE [SPLIT]_b___b___b___>

680           690           700           710           720
         *             *             *             *             *
AAA AAT GCT TCA ACA GCT AAA AAA GTG GGT GCG GGT TTT GAA TTG GCA
TTT TTA CGA AGT TGT CGA TTT TTT CAC CCA CGC CCA AAA CTT AAC CGT
Lys Asn Ala Ser Thr Ala Lys Lys Val Gly Ala Gly Phe Glu Leu Ala>
 __b___b____RECOMBINANT LEUKOTOXIN PEPTIDE [SPLIT]_b___b___b___>

730           740           750           760
               *             *             *             *
AAC CAA GTT GTT GGT AAT ATT ACC AAA GCC GTT TCT TCT TAC ATT TTA
TTG GTT CAA CAA CCA TTA TAA TGG TTT CGG CAA AGA AGA ATG TAA AAT
Asn Gln Val Val Gly Asn Ile Thr Lys Ala Val Ser Ser Tyr Ile Leu>
 __b___b____RECOMBINANT LEUKOTOXIN PEPTIDE [SPLIT]_b___b___b___>

770           780           790           800           810
 *             *             *             *             *
GCC CAA CGT GTT GCA GCA GGT TTA TCT TCA ACT GGG CCT GTG GCT GCT
CGG GTT GCA CAA CGT CGT CCA AAT AGA AGT TGA CCC GGA CAC CGA CGA
Ala Gln Arg Val Ala Ala Gly Leu Ser Ser Thr Gly Pro Val Ala Ala>
 __b___b____RECOMBINANT LEUKOTOXIN PEPTIDE [SPLIT]_b___b___b___>

820           830           840           850           860
         *             *             *             *             *
TTA ATT GCT TCT ACT GTT TCT CTT GCG ATT AGC CCA TTA GCA TTT GCC
AAT TAA CGA AGA TGA CAA AGA GAA CGC TAA TCG GGT AAT CGT AAA CGG
Leu Ile Ala Ser Thr Val Ser Leu Ala Ile Ser Pro Leu Ala Phe Ala>
 __b___b____RECOMBINANT LEUKOTOXIN PEPTIDE [SPLIT]_b___b___b___>
```

FIG. 8C

```
      870          880          890          900          910
*     *     *      *     *      *      *     *      *     *
GGT ATT GCC GAT AAA TTT AAT CAT GCA AAA AGT TTA GAG AGT TAT GCC
CCA TAA CGG CTA TTT AAA TTA GTA CGT TTT TCA AAT CTC TCA ATA CGG
Gly Ile Ala Asp Lys Phe Asn His Ala Lys Ser Leu Glu Ser Tyr Ala>
___b___b____RECOMBINANT LEUKOTOXIN PEPTIDE [SPLIT]_b___b___b___>

920          930          940          950          960
  *       *      *     *      *     *       *     *      *     *
GAA CGC TTT AAA AAA TTA GGC TAT GAC GGA GAT AAT TTA TTA GCA GAA
CTT GCG AAA TTT TTT AAT CCG ATA CTG CCT CTA TTA AAT AAT CGT CTT
Glu Arg Phe Lys Lys Leu Gly Tyr Asp Gly Asp Asn Leu Leu Ala Glu>
___b___b____RECOMBINANT LEUKOTOXIN PEPTIDE [SPLIT]_b___b___b___>

970          980          990          1000
      *      *      *     *      *     *      *     *      *
TAT CAG CGG GGA ACA GGG ACT ATT GAT GCA TCG GTT ACT GCA ATT AAT
ATA GTC GCC CCT TGT CCC TGA TAA CTA CGT AGC CAA TGA CGT TAA TTA
Tyr Gln Arg Gly Thr Gly Thr Ile Asp Ala Ser Val Thr Ala Ile Asn>
___b___b____RECOMBINANT LEUKOTOXIN PEPTIDE [SPLIT]_b___b___b___>

1010           1020          1030          1040          1050
  *       *      *      *      *     *      *     *      *     *
ACC GCA TTG GCC GCT ATT GCT GGT GGT GTG TCT GCT GCT GCA GCC GGC
TGG CGT AAC CGG CGA TAA CGA CCA CCA CAC AGA CGA CGA CGT CGG CCG
Thr Ala Leu Ala Ala Ile Ala Gly Gly Val Ser Ala Ala Ala Ala Gly>
___b___b____RECOMBINANT LEUKOTOXIN PEPTIDE [SPLIT]_b___b___b___>

1060          1070          1080          1090          1100
      *     *      *     *      *      *     *      *     *
TCG GTT ATT GCT TCA CCG ATT GCC TTA TTA GTA TCT GGG ATT ACC GGT
AGC CAA TAA CGA AGT GGC TAA CGG AAT AAT CAT AGA CCC TAA TGG CCA
Ser Val Ile Ala Ser Pro Ile Ala Leu Leu Val Ser Gly Ile Thr Gly>
___b___b____RECOMBINANT LEUKOTOXIN PEPTIDE [SPLIT]_b___b___b___>

1110          1120          1130          1140          1150
*     *     *      *     *      *      *     *      *     *
GTA ATT TCT ACG ATT CTG CAA TAT TCT AAA CAA GCA ATG TTT GAG CAC
CAT TAA AGA TGC TAA GAC GTT ATA AGA TTT GTT CGT TAC AAA CTC GTG
Val Ile Ser Thr Ile Leu Gln Tyr Ser Lys Gln Ala Met Phe Glu His>
___b___b____RECOMBINANT LEUKOTOXIN PEPTIDE [SPLIT]_b___b___b___>

1160          1170          1180          1190          1200
  *       *      *     *      *     *      *     *      *     *
GTT GCA AAT AAA ATT CAT AAC AAA ATT GTA GAA TGG GAA AAA AAT AAT
CAA CGT TTA TTT TAA GTA TTG TTT TAA CAT CTT ACC CTT TTT TTA TTA
Val Ala Asn Lys Ile His Asn Lys Ile Val Glu Trp Glu Lys Asn Asn>
___b___b____RECOMBINANT LEUKOTOXIN PEPTIDE [SPLIT]_b___b___b___>
```

FIG. 8D

```
          1210          1220          1230          1240
       *     *     *     *     *     *     *     *     *
CAC GGT AAG AAC TAC TTT GAA AAT GGT TAC GAT GCC CGT TAT CTT GCG
GTG CCA TTC TTG ATG AAA CTT TTA CCA ATG CTA CGG GCA ATA GAA CGC
His Gly Lys Asn Tyr Phe Glu Asn Gly Tyr Asp Ala Arg Tyr Leu Ala>
___b___b____RECOMBINANT LEUKOTOXIN PEPTIDE [SPLIT]_b___b___b___>

1250       1260          1270          1280          1290
 *     *     *     *     *     *     *     *     *     *
AAT TTA CAA GAT AAT ATG AAA TTC TTA CTG AAC TTA AAC AAA GAG TTA
TTA AAT GTT CTA TTA TAC TTT AAG AAT GAC TTG AAT TTG TTT CTC AAT
Asn Leu Gln Asp Asn Met Lys Phe Leu Leu Asn Leu Asn Lys Glu Leu>
___b___b____RECOMBINANT LEUKOTOXIN PEPTIDE [SPLIT]_b___b___b___>

1300          1310          1320          1330          1340
    *     *     *     *     *     *     *     *     *
CAG GCA GAA CGT GTC ATC GCT ATT ACT CAG CAG CAA TGG GAT AAC AAC
GTC CGT CTT GCA CAG TAG CGA TAA TGA GTC GTC GTT ACC CTA TTG TTG
Gln Ala Glu Arg Val Ile Ala Ile Thr Gln Gln Gln Trp Asp Asn Asn>
___b___b____RECOMBINANT LEUKOTOXIN PEPTIDE [SPLIT]_b___b___b___>

1350          1360          1370          1380          1390
*     *     *     *     *     *     *     *     *     *
ATT GGT GAT TTA GCT GGT ATT AGC CGT TTA GGT GAA AAA GTC CTT AGT
TAA CCA CTA AAT CGA CCA TAA TCG GCA AAT CCA CTT TTT CAG GAA TCA
Ile Gly Asp Leu Ala Gly Ile Ser Arg Leu Gly Glu Lys Val Leu Ser>
___b___b____RECOMBINANT LEUKOTOXIN PEPTIDE [SPLIT]_b___b___b___>

1400          1410          1420          1430          1440
  *     *     *     *     *     *     *     *     *     *
GGT AAA GCC TAT GTG GAT GCG TTT GAA GAA GGC AAA CAC ATT AAA GCC
CCA TTT CGG ATA CAC CTA CGC AAA CTT CTT CCG TTT GTG TAA TTT CGG
Gly Lys Ala Tyr Val Asp Ala Phe Glu Glu Gly Lys His Ile Lys Ala>
___b___b____RECOMBINANT LEUKOTOXIN PEPTIDE [SPLIT]_b___b___b___>

1450          1460          1470          1480
       *     *     *     *     *     *     *     *     *
GAT AAA TTA GTA CAG TTG GAT TCG GCA AAC GGT ATT ATT GAT GTG AGT
CTA TTT AAT CAT GTC AAC CTA AGC CGT TTG CCA TAA TAA CTA CAC TCA
Asp Lys Leu Val Gln Leu Asp Ser Ala Asn Gly Ile Ile Asp Val Ser>
___b___b____RECOMBINANT LEUKOTOXIN PEPTIDE [SPLIT]_b___b___b___>
```

FIG. 8E

```
        1490         1500         1510         1520         1530
         *     *      *     *      *     *      *     *      *     *
       AAT  TCG  GGT  AAA  GCG  AAA  ACT  CAG  CAT  ATC  TTA  TTC  AGA  ACG  CCA  TTA
       TTA  AGC  CCA  TTT  CGC  TTT  TGA  GTC  GTA  TAG  AAT  AAG  TCT  TGC  GGT  AAT
       Asn  Ser  Gly  Lys  Ala  Lys  Thr  Gln  His  Ile  Leu  Phe  Arg  Thr  Pro  Leu>
         b    b     RECOMBINANT LEUKOTOXIN PEPTIDE [SPLIT]_b    b    b   >

1540         1550         1560         1570         1580
         *     *      *     *      *     *      *     *      *     *
       TTG  ACG  CCG  GGA  ACA  GAG  CAT  CGT  GAA  CGC  GTA  CAA  ACA  GGT  AAA  TAT
       AAC  TGC  GGC  CCT  TGT  CTC  GTA  GCA  CTT  GCG  CAT  GTT  TGT  CCA  TTT  ATA
       Leu  Thr  Pro  Gly  Thr  Glu  His  Arg  Glu  Arg  Val  Gln  Thr  Gly  Lys  Tyr>
         b    b     RECOMBINANT LEUKOTOXIN PEPTIDE [SPLIT]_b    b    b   >

1590         1600         1610         1620         1630
         *     *      *     *      *     *      *     *      *     *
       GAA  TAT  ATT  ACC  AAG  CTC  AAT  ATT  AAC  CGT  GTA  GAT  AGC  TGG  AAA  ATT
       CTT  ATA  TAA  TGG  TTC  GAG  TTA  TAA  TTG  GCA  CAT  CTA  TCG  ACC  TTT  TAA
       Glu  Tyr  Ile  Thr  Lys  Leu  Asn  Ile  Asn  Arg  Val  Asp  Ser  Trp  Lys  Ile>
         b    b     RECOMBINANT LEUKOTOXIN PEPTIDE [SPLIT]_b    b    b   >

1640         1650         1660         1670         1680
         *     *      *     *      *     *      *     *      *     *
       ACA  GAT  GGT  GCA  GCA  AGT  TCT  ACC  TTT  GAT  TTA  ACT  AAC  GTT  GTT  CAG
       TGT  CTA  CCA  CGT  CGT  TCA  AGA  TGG  AAA  CTA  AAT  TGA  TTG  CAA  CAA  GTC
       Thr  Asp  Gly  Ala  Ala  Ser  Ser  Thr  Phe  Asp  Leu  Thr  Asn  Val  Val  Gln>
         b    b     RECOMBINANT LEUKOTOXIN PEPTIDE [SPLIT]_b    b    b   >

1690         1700         1710         1720
         *     *      *     *      *     *      *     *      *
       CGT  ATT  GGT  ATT  GAA  TTA  GAC  AAT  GCT  GGA  AAT  GTA  ACT  AAA  ACC  AAA
       GCA  TAA  CCA  TAA  CTT  AAT  CTG  TTA  CGA  CCT  TTA  CAT  TGA  TTT  TGG  TTT
       Arg  Ile  Gly  Ile  Glu  Leu  Asp  Asn  Ala  Gly  Asn  Val  Thr  Lys  Thr  Lys>
         b    b     RECOMBINANT LEUKOTOXIN PEPTIDE [SPLIT]_b    b    b   >

1730         1740         1750         1760         1770
   *     *      *     *      *     *      *     *      *     *
 GAA  ACA  AAA  ATT  ATT  GCC  AAA  CTT  GGT  GAA  GGT  GAT  GAC  AAC  GTA  TTT
 CTT  TGT  TTT  TAA  TAA  CGG  TTT  GAA  CCA  CTT  CCA  CTA  CTG  TTG  CAT  AAA
 Glu  Thr  Lys  Ile  Ile  Ala  Lys  Leu  Gly  Glu  Gly  Asp  Asp  Asn  Val  Phe>
   b    b     RECOMBINANT LEUKOTOXIN PEPTIDE [SPLIT]_b    b    b   >

1780         1790         1800         1810         1820
         *     *      *     *      *     *      *     *      *     *
       GTT  GGT  TCT  GGT  ACG  ACG  GAA  ATT  GAT  GGC  GGT  GAA  GGT  TAC  GAC  CGA
       CAA  CCA  AGA  CCA  TGC  TGC  CTT  TAA  CTA  CCG  CCA  CTT  CCA  ATG  CTG  GCT
       Val  Gly  Ser  Gly  Thr  Thr  Glu  Ile  Asp  Gly  Gly  Glu  Gly  Tyr  Asp  Arg>
         b    b     RECOMBINANT LEUKOTOXIN PEPTIDE [SPLIT]_b    b    b   >
```

FIG. 8F

```
          1830          1840          1850          1860          1870
           *     *       *     *       *     *       *     *       *     *
         GTT CAC TAT AGC CGT GGA AAC TAT GGT GCT TTA ACT ATT GAT GCA ACC
         CAA GTG ATA TCG GCA CCT TTG ATA CCA CGA AAT TGA TAA CTA CGT TGG
         Val His Tyr Ser Arg Gly Asn Tyr Gly Ala Leu Thr Ile Asp Ala Thr>
         ___b___b____RECOMBINANT LEUKOTOXIN PEPTIDE [SPLIT]_b___b___b___>

1880          1890          1900          1910          1920
           *     *       *     *       *     *       *     *       *     *
         AAA GAG ACC GAG CAA GGT AGT TAT ACC GTA AAT CGT TTC GTA GAA ACC
         TTT CTC TGG CTC GTT CCA TCA ATA TGG CAT TTA GCA AAG CAT CTT TGG
         Lys Glu Thr Glu Gln Gly Ser Tyr Thr Val Asn Arg Phe Val Glu Thr>
         ___b___b____RECOMBINANT LEUKOTOXIN PEPTIDE [SPLIT]_b___b___b___>

1930          1940          1950          1960
           *     *       *     *       *     *       *     *       *     *
         GGT AAA GCA CTA CAC GAA GTG ACT TCA ACC CAT ACC GCA TTA GTG GGC
         CCA TTT CGT GAT GTG CTT CAC TGA AGT TGG GTA TGG CGT AAT CAC CCG
         Gly Lys Ala Leu His Glu Val Thr Ser Thr His Thr Ala Leu Val Gly>
         ___b___b____RECOMBINANT LEUKOTOXIN PEPTIDE [SPLIT]_b___b___b___>

1970          1980          1990          2000          2010
   *     *       *     *       *     *       *     *       *     *
 AAC CGT GAA GAA AAA ATA GAA TAT CGT CAT AGC AAT AAC CAG CAC CAT
 TTG GCA CTT CTT TTT TAT CTT ATA GCA GTA TCG TTA TTG GTC GTG GTA
 Asn Arg Glu Glu Lys Ile Glu Tyr Arg His Ser Asn Asn Gln His His>
 ___b___b____RECOMBINANT LEUKOTOXIN PEPTIDE [SPLIT]_b___b___b___>

2020          2030          2040          2050          2060
           *     *       *     *       *     *       *     *       *     *
         GCC GGT TAT TAC ACC AAA GAT ACC TTG AAA GCT GTT GAA GAA ATT ATC
         CGG CCA ATA ATG TGG TTT CTA TGG AAC TTT CGA CAA CTT CTT TAA TAG
         Ala Gly Tyr Tyr Thr Lys Asp Thr Leu Lys Ala Val Glu Glu Ile Ile>
         ___b___b____RECOMBINANT LEUKOTOXIN PEPTIDE [SPLIT]_b___b___b___>

2070          2080          2090          2100          2110
           *     *       *     *       *     *       *     *       *     *
         GGT ACA TCA CAT AAC GAT ATC TTT AAA GGT AGT AAG TTC AAT GAT GCC
         CCA TGT AGT GTA TTG CTA TAG AAA TTT CCA TCA TTC AAG TTA CTA CGG
         Gly Thr Ser His Asn Asp Ile Phe Lys Gly Ser Lys Phe Asn Asp Ala>
         ___b___b____RECOMBINANT LEUKOTOXIN PEPTIDE [SPLIT]_b___b___b___>
```

FIG. 8G

```
                2120          2130          2140          2150          2160
                 *     *       *     *       *     *       *     *       *     *
         TTT AAC GGT GGT GAT GGT GTC GAT ACT ATT GAC GGT AAC GAC GGC AAT
         AAA TTG CCA CCA CTA CCA CAG CTA TGA TAA CTG CCA TTG CTG CCG TTA
         Phe Asn Gly Gly Asp Gly Val Asp Thr Ile Asp Gly Asn Asp Gly Asn>
         ___b___b____RECOMBINANT LEUKOTOXIN PEPTIDE [SPLIT]_b___b___b___>

2170          2180          2190          2200
                 *     *       *     *       *     *       *     *
         GAC CGC TTA TTT GGT GGT AAA GGC GAT GAT ATT CTC GAT GGT GGA AAT
         CTG GCG AAT AAA CCA CCA TTT CCG CTA CTA TAA GAG CTA CCA CCT TTA
         Asp Arg Leu Phe Gly Gly Lys Gly Asp Asp Ile Leu Asp Gly Gly Asn>
         ___b___b____RECOMBINANT LEUKOTOXIN PEPTIDE [SPLIT]_b___b___b___>

2210          2220          2230          2240          2250
        *     *       *     *       *     *       *     *       *     *
   GGT GAT GAT TTT ATC GAT GGC GGT AAA GGC AAC GAC CTA TTA CAC GGT
   CCA CTA CTA AAA TAG CTA CCG CCA TTT CCG TTG CTG GAT AAT GTG CCA
   Gly Asp Asp Phe Ile Asp Gly Gly Lys Gly Asn Asp Leu Leu His Gly>
   ___b___b____RECOMBINANT LEUKOTOXIN PEPTIDE [SPLIT]_b___b___b___>

2260          2270          2280          2290          2300
              *     *       *     *       *     *       *     *       *
         GGC AAG GGC GAT GAT ATT TTC GTT CAC CGT AAA GGC GAT GGT AAT GAT
         CCG TTC CCG CTA CTA TAA AAG CAA GTG GCA TTT CCG CTA CCA TTA CTA
         Gly Lys Gly Asp Asp Ile Phe Val His Arg Lys Gly Asp Gly Asn Asp>
         ___b___b____RECOMBINANT LEUKOTOXIN PEPTIDE [SPLIT]_b___b___b___>

2310          2320          2330          2340          2350
                 *     *       *     *       *     *       *     *       *
         ATT ATT ACC GAT TCT GAC GGC AAT GAT AAA TTA TCA TTC TCT GAT TCG
         TAA TAA TGG CTA AGA CTG CCG TTA CTA TTT AAT AGT AAG AGA CTA AGC
         Ile Ile Thr Asp Ser Asp Gly Asn Asp Lys Leu Ser Phe Ser Asp Ser>
         ___b___b____RECOMBINANT LEUKOTOXIN PEPTIDE [SPLIT]_b___b___b___>

2360          2370          2380          2390          2400
                 *     *       *     *       *     *       *     *       *
         AAC TTA AAA GAT TTA ACA TTT GAA AAA GTT AAA CAT AAT CTT GTC ATC
         TTG AAT TTT CTA AAT TGT AAA CTT TTT CAA TTT GTA TTA GAA CAG TAG
         Asn Leu Lys Asp Leu Thr Phe Glu Lys Val Lys His Asn Leu Val Ile>
         ___b___b____RECOMBINANT LEUKOTOXIN PEPTIDE [SPLIT]_b___b___b___>

2410          2420          2430          2440
                    *     *       *     *       *     *       *     *
            ACG AAT AGC AAA AAA GAG AAA GTG ACC ATT CAA AAC TGG TTC CGA GAG
            TGC TTA TCG TTT TTT CTC TTT CAC TGG TAA GTT TTG ACC AAG GCT CTC
            Thr Asn Ser Lys Lys Glu Lys Val Thr Ile Gln Asn Trp Phe Arg Glu>
            ___b___b____RECOMBINANT LEUKOTOXIN PEPTIDE [SPLIT]_b___b___b___>
```

FIG. 8H

```
2450      2460      2470      2480      2490
 *     *     *     *     *     *     *     *     *     *
GCT GAT TTT GCT AAA GAA GTG CCT AAT TAT AAA GCA ACT AAA GAT GAG
CGA CTA AAA CGA TTT CTT CAC GGA TTA ATA TTT CGT TGA TTT CTA CTC
Ala Asp Phe Ala Lys Glu Val Pro Asn Tyr Lys Ala Thr Lys Asp Glu>
___b___b____RECOMBINANT LEUKOTOXIN PEPTIDE [SPLIT]_b___b___b___>

2500      2510      2520      2530      2540
   *     *     *     *     *     *     *     *     *
AAA ATC GAA GAA ATC ATC GGT CAA AAT GGC GAG CGG ATC ACC TCA AAG
TTT TAG CTT CTT TAG TAG CCA GTT TTA CCG CTC GCC TAG TGG AGT TTC
Lys Ile Glu Glu Ile Ile Gly Gln Asn Gly Glu Arg Ile Thr Ser Lys>
___b___b____RECOMBINANT LEUKOTOXIN PEPTIDE [SPLIT]_b___b___b___>

2550      2560      2570      2580      2590
 *     *     *     *     *     *     *     *     *     *
CAA GTT GAT GAT CTT ATC GCA AAA GGT AAC GGC AAA ATT ACC CAA GAT
GTT CAA CTA CTA GAA TAG CGT TTT CCA TTG CCG TTT TAA TGG GTT CTA
Gln Val Asp Asp Leu Ile Ala Lys Gly Asn Gly Lys Ile Thr Gln Asp>
___b___b____RECOMBINANT LEUKOTOXIN PEPTIDE [SPLIT]_b___b___b___>

2600      2610      2620      2630      2640
  *     *     *     *     *     *     *     *     *     *
GAG CTA TCA AAA GTT GTT GAT AAC TAT GAA TTG CTC AAA CAT AGC AAA
CTC GAT AGT TTT CAA CAA CTA TTG ATA CTT AAC GAG TTT GTA TCG TTT
Glu Leu Ser Lys Val Val Asp Asn Tyr Glu Leu Leu Lys His Ser Lys>
___b___b____RECOMBINANT LEUKOTOXIN PEPTIDE [SPLIT]_b___b___b___>

2650      2660      2670      2680
    *     *     *     *     *     *     *     *     *
AAT GTG ACA AAC AGC TTA GAT AAG TTA ATC TCA TCT GTA AGT GCA TTT
TTA CAC TGT TTG TCG AAT CTA TTC AAT TAG AGT AGA CAT TCA CGT AAA
Asn Val Thr Asn Ser Leu Asp Lys Leu Ile Ser Ser Val Ser Ala Phe>
___b___b____RECOMBINANT LEUKOTOXIN PEPTIDE [SPLIT]_b___b___b___>

2690      2700      2710      2720      2730
 *     *     *     *     *     *     *     *     *     *
ACC TCG TCT AAT GAT TCG AGA AAT GTA TTA GTG GCT CCA ACT TCA ATG
TGG AGC AGA TTA CTA AGC TCT TTA CAT AAT CAC CGA GGT TGA AGT TAC
Thr Ser Ser Asn Asp Ser Arg Asn Val Leu Val Ala Pro Thr Ser Met>
___b___b____RECOMBINANT LEUKOTOXIN PEPTIDE [SPLIT]_b___b___b___>
```

FIG. 8I

```
         2740          2750          2760          2770          2780
           *             *             *             *             *
       TTG GAT CAA AGT TTA TCT TCT CTT CAA TTT GCT AGG GGA TCT CAG CAT
       AAC CTA GTT TCA AAT AGA AGA GAA GTT AAA CGA TCC CCT AGA GTC GTA
                                                                Gln His>
       Leu Asp Gln Ser Leu Ser Ser Leu Gln Phe Ala Arg Gly Ser>___a___>
       ___b____RECOMBINANT LEUKOTOXIN PEPTIDE [SPLIT]_b___b___>

2790          2800          2810
            *             *             *
       TGG AGC TAC GGC CTG CGC CCT GGC TAA GGATCC
       ACC TCG ATG CCG GAC GCG GGA CCG ATT CCTAGG
       Trp Ser Tyr Gly Leu Arg Pro Gly End>
       ___a___a___a___GNRH____a___a___a___>
```

FIG. 8J

```
              10             20             30             40
    *    *    *    *    *    *    *    *    *    *
ATG  GCT  ACT  GTT  ATA  GAT  CTA  AGC  TTC  CCA  AAA  ACT  GGG  GCA  AAA  AAA
TAC  CGA  TGA  CAA  TAT  CTA  GAT  TCG  AAG  GGT  TTT  TGA  CCC  CGT  TTT  TTT
Met  Ala  Thr  Val  Ile  Asp  Leu  Ser  Phe  Pro  Lys  Thr  Gly  Ala  Lys  Lys>
___b___b____RECOMBINANT LEUKOTOXIN PEPTIDE [SPLIT]_b___b___b___>

50             60             70             80             90
 *    *    *    *    *    *    *    *    *    *    *
ATT  ATC  CTC  TAT  ATT  CCC  CAA  AAT  TAC  CAA  TAT  GAT  ACT  GAA  CAA  GGT
TAA  TAG  GAG  ATA  TAA  GGG  GTT  TTA  ATG  GTT  ATA  CTA  TGA  CTT  GTT  CCA
Ile  Ile  Leu  Tyr  Ile  Pro  Gln  Asn  Tyr  Gln  Tyr  Asp  Thr  Glu  Gln  Gly>
___b___b____RECOMBINANT LEUKOTOXIN PEPTIDE [SPLIT]_b___b___b___>

100            110            120            130            140
 *    *    *    *    *    *    *    *    *    *
AAT  GGT  TTA  CAG  GAT  TTA  GTC  AAA  GCG  GCC  GAA  GAG  TTG  GGG  ATT  GAG
TTA  CCA  AAT  GTC  CTA  AAT  CAG  TTT  CGC  CGG  CTT  CTC  AAC  CCC  TAA  CTC
Asn  Gly  Leu  Gln  Asp  Leu  Val  Lys  Ala  Ala  Glu  Glu  Leu  Gly  Ile  Glu>
___b___b____RECOMBINANT LEUKOTOXIN PEPTIDE [SPLIT]_b___b___b___>

150            160            170            180            190
 *    *    *    *    *    *    *    *    *    *
GTA  CAA  AGA  GAA  GAA  CGC  AAT  AAT  ATT  GCA  ACA  GCT  CAA  ACC  AGT  TTA
CAT  GTT  TCT  CTT  CTT  GCG  TTA  TTA  TAA  CGT  TGT  CGA  GTT  TGG  TCA  AAT
Val  Gln  Arg  Glu  Glu  Arg  Asn  Asn  Ile  Ala  Thr  Ala  Gln  Thr  Ser  Leu>
___b___b____RECOMBINANT LEUKOTOXIN PEPTIDE [SPLIT]_b___b___b___>

200            210            220            230            240
 *    *    *    *    *    *    *    *    *    *
GGC  ACG  ATT  CAA  ACC  GCT  ATT  GGC  TTA  ACT  GAG  CGT  GGC  ATT  GTG  TTA
CCG  TGC  TAA  GTT  TGG  CGA  TAA  CCG  AAT  TGA  CTC  GCA  CCG  TAA  CAC  AAT
Gly  Thr  Ile  Gln  Thr  Ala  Ile  Gly  Leu  Thr  Glu  Arg  Gly  Ile  Val  Leu>
___b___b____RECOMBINANT LEUKOTOXIN PEPTIDE [SPLIT]_b___b___b___>
```

FIG. 10A

```
            250         260         270         280
     *       *     *     *     *     *     *     *     *
TCC GCT CCA CAA ATT GAT AAA TTG CTA CAG AAA ACT AAA GCA GGC CAA
AGG CGA GGT GTT TAA CTA TTT AAC GAT GTC TTT TGA TTT CGT CCG GTT
Ser Ala Pro Gln Ile Asp Lys Leu Leu Gln Lys Thr Lys Ala Gly Gln>
___b___b____RECOMBINANT LEUKOTOXIN PEPTIDE [SPLIT]_b___b___b___>

290         300         310         320         330
 *     *     *     *     *     *     *     *     *     *
GCA TTA GGT TCT GCC GAA AGC ATT GTA CAA AAT GCA AAT AAA GCC AAA
CGT AAT CCA AGA CGG CTT TCG TAA CAT GTT TTA CGT TTA TTT CGG TTT
Ala Leu Gly Ser Ala Glu Ser Ile Val Gln Asn Ala Asn Lys Ala Lys>
___b___b____RECOMBINANT LEUKOTOXIN PEPTIDE [SPLIT]_b___b___b___>

340         350         360         370         380
    *     *     *     *     *     *     *     *     *
ACT GTA TTA TCT GGC ATT CAA TCT ATT TTA GGC TCA GTA TTG GCT GGA
TGA CAT AAT AGA CCG TAA GTT AGA TAA AAT CCG AGT CAT AAC CGA CCT
Thr Val Leu Ser Gly Ile Gln Ser Ile Leu Gly Ser Val Leu Ala Gly>
___b___b____RECOMBINANT LEUKOTOXIN PEPTIDE [SPLIT]_b___b___b___>

390         400         410         420         430
*     *     *     *     *     *     *     *     *     *
ATG GAT TTA GAT GAG GCC TTA CAG AAT AAC AGC AAC CAA CAT GCT CTT
TAC CTA AAT CTA CTC CGG AAT GTC TTA TTG TCG TTG GTT GTA CGA GAA
Met Asp Leu Asp Glu Ala Leu Gln Asn Asn Ser Asn Gln His Ala Leu>
___b___b____RECOMBINANT LEUKOTOXIN PEPTIDE [SPLIT]_b___b___b___>

440         450         460         470         480
  *     *     *     *     *     *     *     *     *     *
GCT AAA GCT GGC TTG GAG CTA ACA AAT TCA TTA ATT GAA AAT ATT GCT
CGA TTT CGA CCG AAC CTC GAT TGT TTA AGT AAT TAA CTT TTA TAA CGA
Ala Lys Ala Gly Leu Glu Leu Thr Asn Ser Leu Ile Glu Asn Ile Ala>
___b___b____RECOMBINANT LEUKOTOXIN PEPTIDE [SPLIT]_b___b___b___>

490         500         510         520
    *     *     *     *     *     *     *     *     *
AAT TCA GTA AAA ACA CTT GAC GAA TTN -GT GAG CAA ATT AGT CAA TTT
TTA AGT CAT TTT TGT GAA CTG CTT AAN -CA CTC GTT TAA TCA GTT AAA
Asn Ser Val Lys Thr Leu Asp Glu Xxx Cys Glu Gln Ile Ser Gln Phe>
___b___b____RECOMBINANT LEUKOTOXIN PEPTIDE [SPLIT]_b___b___b___>

530         540         550         560         570
 *     *     *     *     *     *     *     *     *     *
GGT TCA AAA CTA CAA AAT ATC AAA GGC TTA GGG ACT TTA GGA GAC AAA
CCA AGT TTT GAT GTT TTA TAG TTT CCG AAT CCC TGA AAT CCT CTG TTT
Gly Ser Lys Leu Gln Asn Ile Lys Gly Leu Gly Thr Leu Gly Asp Lys>
___b___b____RECOMBINANT LEUKOTOXIN PEPTIDE [SPLIT]_b___b___b___>
```

FIG. 10B

```
          580           590           600           610           620
           *             *             *             *             *
CTC AAA AAT ATC GGT GGA CTT GAT AAA GCT GGC CTT GGT TTA GAT GTT
GAG TTT TTA TAG CCA CCT GAA CTA TTT CGA CCG GAA CCA AAT CTA CAA
Leu Lys Asn Ile Gly Gly Leu Asp Lys Ala Gly Leu Gly Leu Asp Val>
___b___b____RECOMBINANT LEUKOTOXIN PEPTIDE [SPLIT]_b___b___b___>

630           640           650           660           670
  *             *             *             *             *             *
ATC TCA GGG CTA TTA TCG GGC GCA ACA GCT GCA CTT GTA CTT GCA GAT
TAG AGT CCC GAT AAT AGC CCG CGT TGT CGA CGT GAA CAT GAA CGT CTA
Ile Ser Gly Leu Leu Ser Gly Ala Thr Ala Ala Leu Val Leu Ala Asp>
___b___b____RECOMBINANT LEUKOTOXIN PEPTIDE [SPLIT]_b___b___b___>

680           690           700           710           720
  *         *             *             *             *             *
AAA AAT GCT TCA ACA GCT AAA AAA GTG GGT GCG GGT TTT GAA TTG GCA
TTT TTA CGA AGT TGT CGA TTT TTT CAC CCA CGC CCA AAA CTT AAC CGT
Lys Asn Ala Ser Thr Ala Lys Lys Val Gly Ala Gly Phe Glu Leu Ala>
___b___b____RECOMBINANT LEUKOTOXIN PEPTIDE [SPLIT]_b___b___b___>

730           740           750           760
  *             *             *      *      *             *             *
AAC CAA GTT GTT GGT AAT ATT ACC AAA GCC GTT TCT TCT TAC ATT TTA
TTG GTT CAA CAA CCA TTA TAA TGG TTT CGG CAA AGA AGA ATG TAA AAT
Asn Gln Val Val Gly Asn Ile Thr Lys Ala Val Ser Ser Tyr Ile Leu>
___b___b____RECOMBINANT LEUKOTOXIN PEPTIDE [SPLIT]_b___b___b___>

770           780           790           800           810
  *       *         *         *         *         *             *
GCC CAA CGT GTT GCA GCA GGT TTA TCT TCA ACT GGG CCT GTG GCT GCT
CGG GTT GCA CAA CGT CGT CCA AAT AGA AGT TGA CCC GGA CAC CGA CGA
Ala Gln Arg Val Ala Ala Gly Leu Ser Ser Thr Gly Pro Val Ala Ala>
___b___b____RECOMBINANT LEUKOTOXIN PEPTIDE [SPLIT]_b___b___b___>

820           830           840           850           860
           *             *             *             *             *
TTA ATT GCT TCT ACT GTT TCT CTT GCG ATT AGC CCA TTA GCA TTT GCC
AAT TAA CGA AGA TGA CAA AGA GAA CGC TAA TCG GGT AAT CGT AAA CGG
Leu Ile Ala Ser Thr Val Ser Leu Ala Ile Ser Pro Leu Ala Phe Ala>
___b___b____RECOMBINANT LEUKOTOXIN PEPTIDE [SPLIT]_b___b___b___>
```

FIG. 10C

```
         870          880          890          900          910
     *    *      *    *      *    *      *    *      *    *      *
    GGT ATT GCC GAT AAA TTT AAT CAT GCA AAA AGT TTA GAG AGT TAT GCC
    CCA TAA CGG CTA TTT AAA TTA GTA CGT TTT TCA AAT CTC TCA ATA CGG
    Gly Ile Ala Asp Lys Phe Asn His Ala Lys Ser Leu Glu Ser Tyr Ala>
    ___b___b____RECOMBINANT LEUKOTOXIN PEPTIDE [SPLIT]_b___b___b___>

920          930          940          950          960
     *    *      *    *      *    *      *    *      *    *      *
    GAA CGC TTT AAA AAA TTA GGC TAT GAC GGA GAT AAT TTA TTA GCA GAA
    CTT GCG AAA TTT TTT AAT CCG ATA CTG CCT CTA TTA AAT AAT CGT CTT
    Glu Arg Phe Lys Lys Leu Gly Tyr Asp Gly Asp Asn Leu Leu Ala Glu>
    ___b___b____RECOMBINANT LEUKOTOXIN PEPTIDE [SPLIT]_b___b___b___>

970          980          990          1000
     *    *      *    *      *    *      *    *      *    *
    TAT CAG CGG GGA ACA GGG ACT ATT GAT GCA TCG GTT ACT GCA ATT AAT
    ATA GTC GCC CCT TGT CCC TGA TAA CTA CGT AGC CAA TGA CGT TAA TTA
    Tyr Gln Arg Gly Thr Gly Thr Ile Asp Ala Ser Val Thr Ala Ile Asn>
    ___b___b____RECOMBINANT LEUKOTOXIN PEPTIDE [SPLIT]_b___b___b___>

1010         1020         1030         1040         1050
     *    *      *    *      *    *      *    *      *    *      *
    ACC GCA TTG GCC GCT ATT GCT GGT GGT GTG TCT GCT GCT GCA GCC GGC
    TGG CGT AAC CGG CGA TAA CGA CCA CCA CAC AGA CGA CGA CGT CGG CCG
    Thr Ala Leu Ala Ala Ile Ala Gly Gly Val Ser Ala Ala Ala Ala Gly>
    ___b___b____RECOMBINANT LEUKOTOXIN PEPTIDE [SPLIT]_b___b___b___>

1060         1070         1080         1090         1100
     *    *      *    *      *    *      *    *      *    *      *
    TCG GTT ATT GCT TCA CCG ATT GCC TTA TTA GTA TCT GGG ATT ACC GGT
    AGC CAA TAA CGA AGT GGC TAA CGG AAT AAT CAT AGA CCC TAA TGG CCA
    Ser Val Ile Ala Ser Pro Ile Ala Leu Leu Val Ser Gly Ile Thr Gly>
    ___b___b____RECOMBINANT LEUKOTOXIN PEPTIDE [SPLIT]_b___b___b___>

1110         1120         1130         1140         1150
     *    *      *    *      *    *      *    *      *    *      *
    GTA ATT TCT ACG ATT CTG CAA TAT TCT AAA CAA GCA ATG TTT GAG CAC
    CAT TAA AGA TGC TAA GAC GTT ATA AGA TTT GTT CGT TAC AAA CTC GTG
    Val Ile Ser Thr Ile Leu Gln Tyr Ser Lys Gln Ala Met Phe Glu His>
    ___b___b____RECOMBINANT LEUKOTOXIN PEPTIDE [SPLIT]_b___b___b___>

1160         1170         1180         1190         1200
     *    *      *    *      *    *      *    *      *    *      *
    GTT GCA AAT AAA ATT CAT AAC AAA ATT GTA GAA TGG GAA AAA AAT AAT
    CAA CGT TTA TTT TAA GTA TTG TTT TAA CAT CTT ACC CTT TTT TTA TTA
    Val Ala Asn Lys Ile His Asn Lys Ile Val Glu Trp Glu Lys Asn Asn>
    ___b___b____RECOMBINANT LEUKOTOXIN PEPTIDE [SPLIT]_b___b___b___>
```

FIG. 10D

```
        1210        1220        1230        1240
     *     *     *     *     *     *     *     *     *
CAC GGT AAG AAC TAC TTT GAA AAT GGT TAC GAT GCC CGT TAT CTT GCG
GTG CCA TTC TTG ATG AAA CTT TTA CCA ATG CTA CGG GCA ATA GAA CGC
His Gly Lys Asn Tyr Phe Glu Asn Gly Tyr Asp Ala Arg Tyr Leu Ala>
___b___b____RECOMBINANT LEUKOTOXIN PEPTIDE [SPLIT]_b___b___b___>

1250        1260        1270        1280        1290
 *     *     *     *     *     *     *     *     *     *
AAT TTA CAA GAT AAT ATG AAA TTC TTA CTG AAC TTA AAC AAA GAG TTA
TTA AAT GTT CTA TTA TAC TTT AAG AAT GAC TTG AAT TTG TTT CTC AAT
Asn Leu Gln Asp Asn Met Lys Phe Leu Leu Asn Leu Asn Lys Glu Leu>
___b___b____RECOMBINANT LEUKOTOXIN PEPTIDE [SPLIT]_b___b___b___>

1300        1310        1320        1330        1340
     *     *     *     *     *     *     *     *     *
CAG GCA GAA CGT GTC ATC GCT ATT ACT CAG CAG CAA TGG GAT AAC AAC
GTC CGT CTT GCA CAG TAG CGA TAA TGA GTC GTC GTT ACC CTA TTG TTG
Gln Ala Glu Arg Val Ile Ala Ile Thr Gln Gln Gln Trp Asp Asn Asn>
___b___b____RECOMBINANT LEUKOTOXIN PEPTIDE [SPLIT]_b___b___b___>

1350        1360        1370        1380        1390
 *     *     *     *     *     *     *     *     *     *
ATT GGT GAT TTA GCT GGT ATT AGC CGT TTA GGT GAA AAA GTC CTT AGT
TAA CCA CTA AAT CGA CCA TAA TCG GCA AAT CCA CTT TTT CAG GAA TCA
Ile Gly Asp Leu Ala Gly Ile Ser Arg Leu Gly Glu Lys Val Leu Ser>
___b___b____RECOMBINANT LEUKOTOXIN PEPTIDE [SPLIT]_b___b___b___>

1400        1410        1420        1430        1440
   *     *     *     *     *     *     *     *     *     *
GGT AAA GCC TAT GTG GAT GCG TTT GAA GAA GGC AAA CAC ATT AAA GCC
CCA TTT CGG ATA CAC CTA CGC AAA CTT CTT CCG TTT GTG TAA TTT CGG
Gly Lys Ala Tyr Val Asp Ala Phe Glu Glu Gly Lys His Ile Lys Ala>
___b___b____RECOMBINANT LEUKOTOXIN PEPTIDE [SPLIT]_b___b___b___>

1450        1460        1470        1480
     *     *     *     *     *     *     *     *     *
GAT AAA TTA GTA CAG TTG GAT TCG GCA AAC GGT ATT ATT GAT GTG AGT
CTA TTT AAT CAT GTC AAC CTA AGC CGT TTG CCA TAA TAA CTA CAC TCA
Asp Lys Leu Val Gln Leu Asp Ser Ala Asn Gly Ile Ile Asp Val Ser>
___b___b____RECOMBINANT LEUKOTOXIN PEPTIDE [SPLIT]_b___b___b___>
```

FIG. 10E

```
      1490          1500          1510          1520          1530
        *     *       *     *       *     *       *     *       *     *
      AAT TCG GGT AAA GCG AAA ACT CAG CAT ATC TTA TTC AGA ACG CCA TTA
      TTA AGC CCA TTT CGC TTT TGA GTC GTA TAG AAT AAG TCT TGC GGT AAT
      Asn Ser Gly Lys Ala Lys Thr Gln His Ile Leu Phe Arg Thr Pro Leu>
      ___b___b____RECOMBINANT LEUKOTOXIN PEPTIDE [SPLIT]_b___b___b___>

1540          1550          1560          1570          1580
           *     *       *     *       *     *       *     *       *
         TTG ACG CCG GGA ACA GAG CAT CGT GAA CGC GTA CAA ACA GGT AAA TAT
         AAC TGC GGC CCT TGT CTC GTA GCA CTT GCG CAT GTT TGT CCA TTT ATA
         Leu Thr Pro Gly Thr Glu His Arg Glu Arg Val Gln Thr Gly Lys Tyr>
         ___b___b____RECOMBINANT LEUKOTOXIN PEPTIDE [SPLIT]_b___b___b___>

1590          1600          1610          1620          1630
            *     *       *     *       *     *       *     *       *     *
         GAA TAT ATT ACC AAG CTC AAT ATT AAC CGT GTA GAT AGC TGG AAA ATT
         CTT ATA TAA TGG TTC GAG TTA TAA TTG GCA CAT CTA TCG ACC TTT TAA
         Glu Tyr Ile Thr Lys Leu Asn Ile Asn Arg Val Asp Ser Trp Lys Ile>
         ___b___b____RECOMBINANT LEUKOTOXIN PEPTIDE [SPLIT]_b___b___b___>

1640          1650          1660          1670          1680
                *     *       *     *       *     *       *     *       *     *
            ACA GAT GGT GCA GCA AGT TCT ACC TTT GAT TTA ACT AAC GTT GTT CAG
            TGT CTA CCA CGT CGT TCA AGA TGG AAA CTA AAT TGA TTG CAA CAA GTC
            Thr Asp Gly Ala Ala Ser Ser Thr Phe Asp Leu Thr Asn Val Val Gln>
            ___b___b____RECOMBINANT LEUKOTOXIN PEPTIDE [SPLIT]_b___b___b___>

1690          1700          1710          1720
                    *     *       *     *       *     *       *     *
              CGT ATT GGT ATT GAA TTA GAC AAT GCT GGA AAT GTA ACT AAA ACC AAA
              GCA TAA CCA TAA CTT AAT CTG TTA CGA CCT TTA CAT TGA TTT TGG TTT
              Arg Ile Gly Ile Glu Leu Asp Asn Ala Gly Asn Val Thr Lys Thr Lys>
              ___b___b____RECOMBINANT LEUKOTOXIN PEPTIDE [SPLIT]_b___b___b___>

1730          1740          1750          1760          1770
        *     *       *     *       *     *       *     *       *     *
      GAA ACA AAA ATT ATT GCC AAA CTT GGT GAA GGT GAT GAC AAC GTA TTT
      CTT TGT TTT TAA TAA CGG TTT GAA CCA CTT CCA CTA CTG TTG CAT AAA
      Glu Thr Lys Ile Ile Ala Lys Leu Gly Glu Gly Asp Asp Asn Val Phe>
      ___b___b____RECOMBINANT LEUKOTOXIN PEPTIDE [SPLIT]_b___b___b___>

1780          1790          1800          1810          1820
            *     *       *     *       *     *       *     *       *     *
         GTT GGT TCT GGT ACG ACG GAA ATT GAT GGC GGT GAA GGT TAC GAC CGA
         CAA CCA AGA CCA TGC TGC CTT TAA CTA CCG CCA CTT CCA ATG CTG GCT
         Val Gly Ser Gly Thr Thr Glu Ile Asp Gly Gly Glu Gly Tyr Asp Arg>
         ___b___b____RECOMBINANT LEUKOTOXIN PEPTIDE [SPLIT]_b___b___b___>
```

FIG. 10F

```
   1830       1840       1850       1860       1870
*   *   *   *   *   *   *   *   *   *
GTT CAC TAT AGC CGT GGA AAC TAT GGT GCT TTA ACT ATT GAT GCA ACC
CAA GTG ATA TCG GCA CCT TTG ATA CCA CGA AAT TGA TAA CTA CGT TGG
Val His Tyr Ser Arg Gly Asn Tyr Gly Ala Leu Thr Ile Asp Ala Thr>
___b___b____RECOMBINANT LEUKOTOXIN PEPTIDE [SPLIT]_b___b___b___>

1880       1890       1900       1910       1920
 *   *   *   *   *   *   *   *   *   *
AAA GAG ACC GAG CAA GGT AGT TAT ACC GTA AAT CGT TTC GTA GAA ACC
TTT CTC TGG CTC GTT CCA TCA ATA TGG CAT TTA GCA AAG CAT CTT TGG
Lys Glu Thr Glu Gln Gly Ser Tyr Thr Val Asn Arg Phe Val Glu Thr>
___b___b____RECOMBINANT LEUKOTOXIN PEPTIDE [SPLIT]_b___b___b___>

1930       1940       1950       1960
    *   *   *   *   *   *   *   *   *
GGT AAA GCA CTA CAC GAA GTG ACT TCA ACC CAT ACC GCA TTA GTG GGC
CCA TTT CGT GAT GTG CTT CAC TGA AGT TGG GTA TGG CGT AAT CAC CCG
Gly Lys Ala Leu His Glu Val Thr Ser Thr His Thr Ala Leu Val Gly>
___b___b____RECOMBINANT LEUKOTOXIN PEPTIDE [SPLIT]_b___b___b___>

1970       1980       1990       2000       2010
 *   *   *   *   *   *   *   *   *   *
AAC CGT GAA GAA AAA ATA GAA TAT CGT CAT AGC AAT AAC CAG CAC CAT
TTG GCA CTT CTT TTT TAT CTT ATA GCA GTA TCG TTA TTG GTC GTG GTA
Asn Arg Glu Glu Lys Ile Glu Tyr Arg His Ser Asn Asn Gln His His>
___b___b____RECOMBINANT LEUKOTOXIN PEPTIDE [SPLIT]_b___b___b___>

2020       2030       2040       2050       2060
    *   *   *   *   *   *   *   *   *
GCC GGT TAT TAC ACC AAA GAT ACC TTG AAA GCT GTT GAA GAA ATT ATC
CGG CCA ATA ATG TGG TTT CTA TGG AAC TTT CGA CAA CTT CTT TAA TAG
Ala Gly Tyr Tyr Thr Lys Asp Thr Leu Lys Ala Val Glu Glu Ile Ile>
___b___b____RECOMBINANT LEUKOTOXIN PEPTIDE [SPLIT]_b___b___b___>

2070       2080       2090       2100       2110
*   *   *   *   *   *   *   *   *   *
GGT ACA TCA CAT AAC GAT ATC TTT AAA GGT AGT AAG TTC AAT GAT GCC
CCA TGT AGT GTA TTG CTA TAG AAA TTT CCA TCA TTC AAG TTA CTA CGG
Gly Thr Ser His Asn Asp Ile Phe Lys Gly Ser Lys Phe Asn Asp Ala>
___b___b____RECOMBINANT LEUKOTOXIN PEPTIDE [SPLIT]_b___b___b___>
```

FIG. 10G

```
           2120            2130           2140           2150            2160
            *               *              *               *               *
    *       *       *       *      *       *       *       *       *       *
   TTT     AAC     GGT     GGT    GAT     GGT     GTC     GAT     ACT     ATT     GAC     GGT     AAC     GAC     GGC     AAT
   AAA     TTG     CCA     CCA    CTA     CCA     CAG     CTA     TGA     TAA     CTG     CCA     TTG     CTG     CCG     TTA
   Phe     Asn     Gly     Gly    Asp     Gly     Val     Asp     Thr     Ile     Asp     Gly     Asn     Asp     Gly     Asn>
   ___b___b____RECOMBINANT LEUKOTOXIN PEPTIDE [SPLIT]_b___b___b___>

2170            2180           2190            2200
            *               *              *               *
    *       *       *       *      *       *       *       *       *
   GAC     CGC     TTA     TTT    GGT     GGT     AAA     GGC     GAT     GAT     ATT     CTC     GAT     GGT     GGA     AAT
   CTG     GCG     AAT     AAA    CCA     CCA     TTT     CCG     CTA     CTA     TAA     GAG     CTA     CCA     CCT     TTA
   Asp     Arg     Leu     Phe    Gly     Gly     Lys     Gly     Asp     Asp     Ile     Leu     Asp     Gly     Gly     Asn>
   ___b___b____RECOMBINANT LEUKOTOXIN PEPTIDE [SPLIT]_b___b___b___>

2210            2220           2230           2240            2250
   *              *              *              *               *               *
   *      *       *      *       *      *       *      *        *       *       *
   GGT    GAT    GAT    TTT     ATC    GAT     GGC    GGT     AAA     GGC     AAC     GAC     CTA     TTA     CAC     GGT
   CCA    CTA    CTA    AAA     TAG    CTA     CCG    CCA     TTT     CCG     TTG     CTG     GAT     AAT     GTG     CCA
   Gly    Asp    Asp    Phe     Ile    Asp     Gly    Gly     Lys     Gly     Asn     Asp     Leu     Leu     His     Gly>
   ___b___b____RECOMBINANT LEUKOTOXIN PEPTIDE [SPLIT]_b___b___b___>

2260            2270           2280           2290            2300
            *               *              *              *               *
    *       *       *       *      *       *      *       *       *       *
   GGC     AAG     GGC     GAT    GAT     ATT    TTC     GTT     CAC     CGT     AAA     GGC     GAT     GGT     AAT     GAT
   CCG     TTC     CCG     CTA    CTA     TAA    AAG     CAA     GTG     GCA     TTT     CCG     CTA     CCA     TTA     CTA
   Gly     Lys     Gly     Asp    Asp     Ile    Phe     Val     His     Arg     Lys     Gly     Asp     Gly     Asn     Asp>
   ___b___b____RECOMBINANT LEUKOTOXIN PEPTIDE [SPLIT]_b___b___b___>

2310            2320           2330           2340            2350
            *               *              *              *               *
    *       *       *       *      *       *      *       *       *       *       *
   ATT     ATT     ACC     GAT    TCT     GAC    GGC     AAT     GAT     AAA     TTA     TCA     TTC     TCT     GAT     TCG
   TAA     TAA     TGG     CTA    AGA     CTG    CCG     TTA     CTA     TTT     AAT     AGT     AAG     AGA     CTA     AGC
   Ile     Ile     Thr     Asp    Ser     Asp    Gly     Asn     Asp     Lys     Leu     Ser     Phe     Ser     Asp     Ser>
   ___b___b____RECOMBINANT LEUKOTOXIN PEPTIDE [SPLIT]_b___b___b___>

2360            2370          .2380           2390            2400
            *               *              *              *               *
    *       *       *       *      *       *      *       *       *       *
   AAC     TTA     AAA     GAT    TTA     ACA    TTT     GAA     AAA     GTT     AAA     CAT     AAT     CTT     GTC     ATC
   TTG     AAT     TTT     CTA    AAT     TGT    AAA     CTT     TTT     CAA     TTT     GTA     TTA     GAA     CAG     TAG
   Asn     Leu     Lys     Asp    Leu     Thr    Phe     Glu     Lys     Val     Lys     His     Asn     Leu     Val     Ile>
   ___b___b____RECOMBINANT LEUKOTOXIN PEPTIDE [SPLIT]_b___b___b___>

2410           2420            2430            2440
                    *              *               *               *
            *       *       *       *       *       *       *       *       *
           ACG     AAT     AGC     AAA     AAA     GAG     AAA     GTG     ACC     ATT     CAA     AAC     TGG     TTC     CGA     GAG
           TGC     TTA     TCG     TTT     TTT     CTC     TTT     CAC     TGG     TAA     GTT     TTG     ACC     AAG     GCT     CTC
           Thr     Asn     Ser     Lys     Lys     Glu     Lys     Val     Thr     Ile     Gln     Asn     Trp     Phe     Arg     Glu>
           ___b___b____RECOMBINANT LEUKOTOXIN PEPTIDE [SPLIT]_b___b___b___>
```

FIG. 10H

```
      2450          2460          2470          2480          2490
        *             *             *             *             *
   GCT GAT TTT GCT AAA GAA GTG CCT AAT TAT AAA GCA ACT AAA GAT GAG
   CGA CTA AAA CGA TTT CTT CAC GGA TTA ATA TTT CGT TGA TTT CTA CTC
   Ala Asp Phe Ala Lys Glu Val Pro Asn Tyr Lys Ala Thr Lys Asp Glu>
   ___b___b____RECOMBINANT LEUKOTOXIN PEPTIDE [SPLIT]_b___b___b___>

2500          2510          2520          2530          2540
        *             *             *             *             *
   AAA ATC GAA GAA ATC ATC GGT CAA AAT GGC GAG CGG ATC ACC TCA AAG
   TTT TAG CTT CTT TAG TAG CCA GTT TTA CCG CTC GCC TAG TGG AGT TTC
   Lys Ile Glu Glu Ile Ile Gly Gln Asn Gly Glu Arg Ile Thr Ser Lys>
   ___b___b____RECOMBINANT LEUKOTOXIN PEPTIDE [SPLIT]_b___b___b___>

2550          2560          2570          2580          2590
        *             *             *             *             *
   CAA GTT GAT GAT CTT ATC GCA AAA GGT AAC GGC AAA ATT ACC CAA GAT
   GTT CAA CTA CTA GAA TAG CGT TTT CCA TTG CCG TTT TAA TGG GTT CTA
   Gln Val Asp Asp Leu Ile Ala Lys Gly Asn Gly Lys Ile Thr Gln Asp>
   ___b___b____RECOMBINANT LEUKOTOXIN PEPTIDE [SPLIT]_b___b___b___>

2600          2610          2620          2630          2640
        *             *             *             *             *
   GAG CTA TCA AAA GTT GTT GAT AAC TAT GAA TTG CTC AAA CAT AGC AAA
   CTC GAT AGT TTT CAA CAA CTA TTG ATA CTT AAC GAG TTT GTA TCG TTT
   Glu Leu Ser Lys Val Val Asp Asn Tyr Glu Leu Leu Lys His Ser Lys>
   ___b___b____RECOMBINANT LEUKOTOXIN PEPTIDE [SPLIT]_b___b___b___>

2650          2660          2670          2680
        *             *             *             *             *
   AAT GTG ACA AAC AGC TTA GAT AAG TTA ATC TCA TCT GTA AGT GCA TTT
   TTA CAC TGT TTG TCG AAT CTA TTC AAT TAG AGT AGA CAT TCA CGT AAA
   Asn Val Thr Asn Ser Leu Asp Lys Leu Ile Ser Ser Val Ser Ala Ph >
   ___b___b____RECOMBINANT LEUKOTOXIN PEPTIDE [SPLIT]_b___b___b___>

2690      2700          2710          2720          2730
     *         *             *             *             *
   ACC TCG TCT AAT GAT TCG AGA AAT GTA TTA GTG GCT CCA ACT TCA ATG
   TGG AGC AGA TTA CTA AGC TCT TTA CAT AAT CAC CGA GGT TGA AGT TAC
   Thr Ser Ser Asn Asp Ser Arg Asn Val Leu Val Ala Pro Thr Ser Met>
   ___b___b____RECOMBINANT LEUKOTOXIN PEPTIDE [SPLIT]_b___b___b___>
```

FIG. 10I

```
         2740          2750          2760          2770          2780
           *             *             *             *             *
         *             *             *             *             *
TTG GAT CAA AGT TTA TCT TCT CTT CAA TTT GCT AGG GGA TCT TGC AAC
AAC CTA GTT TCA AAT AGA AGA GAA GTT AAA CGA TCC CCT AGA ACG TTG
                                                          Cys Asn>
                                                           a    >
Leu Asp Gln Ser Leu Ser Ser Leu Gln Phe Ala Arg Gly Ser>
   b    RECOMBINANT LEUKOTOXIN PEPTIDE [SPLIT]_b   b   >

2790          2800          2810          2820          2830
         *             *             *             *             *
       *             *             *             *             *
ATT GTG CCT GTG AGC ATT GTG AGC CGC AAC ATT GTG TAC ACC CGC GCG
TAA CAC GGA CAC TCG TAA CAC TCG GCG TTG TAA CAC ATG TGG GCG CGC
Ile Val Pro Val Ser Ile Val Ser Arg Asn Ile Val Tyr Thr Arg Ala>
   a   a   a   a   a   a   a_|VP4 a   a   a   a   a   a   a   >

2840          2850          2860
         *             *             *
       *             *             *
CAA CCT AAC CAA GAC ATT GTG TAG GATCC
GTT GGA TTG GTT CTG TAA CAC ATC CTAGG
Gln Pro Asn Gln Asp Ile Val End>
   a   a   a_|VP4 a   a   a   >
```

FIG. 10J

ENHANCED IMMUNOGENICITY USING LEUKOTOXIN CHIMERAS

CROSS-REFERENCE TO RELATED APPLICATION

This application is a continuation of U.S. patent application Ser. No. 08/455,970 filed on May 31, 1995 now U.S. Pat. No. 5,708,155, which is a divisional of application Ser. No. 07/960,932 filed Oct. 14, 1992 (now U.S. Pat. No. 5,422,110), which is a continuation-in-part of application Ser. No. 07/779,171 filed Oct. 16, 1991 now abandoned.

TECHNICAL FIELD

The present invention relates generally to immunological carrier systems. More particularly, the invention pertains to leukotoxin-antigen chimeras which demonstrate enhanced immunogenicity as compared to the immunogenicity of the antigen alone.

BACKGROUND OF THE INVENTION

Subunit vaccines are vaccines which are devoid of intact pathogen cells. These vaccines are usually composed of substantially purified antigens. Such vaccines are generally preferable to compositions which use attenuated or inactivated pathogens. However, many subunit vaccines which include proteins, such as peptide hormones and bacterial and viral antigens, require the help of a carrier protein in order to elicit a strong immune response. This is especially true for small proteins or endogenous substances, such as hormones, which are poorly immunogenic.

The carrier serves to non-specifically stimulate T helper cell activity and to direct the antigen to the antigen presenting cell, where the antigen is processed and presented at the cell surface in the context of molecules of the major histocompatibility complex (MHC).

Several carrier systems have been developed for this purpose. For example, small peptide antigens are often coupled to protein carriers such as keyhole limpet haemocyanin (Bittle, J. L., et al., *Nature* (1982) 298:30–33), tetanus toxoid (Muller, G., et al., *Proc. Natl. Acad. Sci. U.S.A.* (1982) 79:569–573), ovalbumin, and sperm whale myoglobin, to produce an immune response. However, carriers may elicit strong immunity not relevant to the peptide antigen and this may inhibit the immune response to the peptide vaccine on secondary immunization (Schutze, M. P., et al, *J. Immun.* (1985) 135:2319–2322).

Antigen delivery systems have also been based on particulate carriers. For example, preformed particles have been used as platforms onto which antigens can be coupled and incorporated. Systems based on proteosomes (Lowell, G. H., et al., *Science* (1988) 240:800–802), immune stimulatory complexes (Morein, B., et al., *Nature* (1984) 308:457–460), and viral particles such as HBsAg (Neurath, A. R., et al., *Mol. Immunol.* (1989) 26:53–62) and rotavirus inner capsid protein (Redmond, M. J., et al., *Mol. Immunol.* (1991) 28:269–278) have been developed.

Other carrier systems have been devised using recombinantly produced chimeric proteins that self assemble into particles. For example, the yeast retrotransposon, Ty, encodes a series of proteins that assemble into virus like particles (Ty-VLPs; Kingsman, S. M., and A. J. Kingsman *Vacc.* (1988) 6:304–306). Foreign genes have been inserted into the TyA gene and expressed in yeast as a fusion protein. The fusion protein retains the capacity to self assemble into particles of uniform size.

Other chimeric protein particles have been examined such as HBsAg, (Valenzuela, P., et al., *Bio/Technol.* (1985) 3:323–326; U.S. Pat. No. 4,722,840; Delpeyroux, F. N., et al., *Science* (1986) 233:472–475), Hepatitis B core antigen (Clarke, B. E., et al., *Vaccines* 88 (Ed. H. Ginsberg, et al., 1988) pp. 127–131), Poliovirus (Burke, K. L., et al., *Nature* (1988) =:81–82), and Tobacco Mosaic Virus (Haynes, J. R., et al., *Bio/Technol.* (1986) 4:637–641). However, these carriers are restricted in their usefulness by virtue of the limited size of the active agent which may be inserted into the structural protein without interfering with particle assembly.

Gene fusions provide a convenient method for the production of chimeric proteins. The expression of chimeric proteins affords an efficient means of linking a carrier protein to a desired antigen.

*Pasteurella haemolytica* produces a cytotoxin which is a leukotoxin. See, e.g. Gentry et al. *Vet. Immunology and Immunopathology* (1985) 9:239–250; Shewen, P. E., and Wilkie, B. N. *Infect. Immun.* (1987) 55:3233–3236. The gene encoding this cytotoxin has been cloned and expressed in bacterial cells. Lo et al. *Infect. Immun.* (1985) 50:667–671; U.S. Pat. No. 5,055,400. The leukotoxin has been used as an antigen in vaccine formulations to fight shipping fever pneumonia in livestock (See, e.g. U.S. Pat. No. 4,957,739) as well as to produce chimeric molecules for use in vaccines against shipping fever (see, e.g. International Publication No. WO 92/03558, published Mar. 5, 1992; and U.S. Pat. No. 5,028,423). However, the use of leukotoxin as a carrier molecule to increase the immune response of antigens associated therewith has not heretofore been described.

DISCLOSURE OF THE INVENTION

The present invention is based on the construction of novel gene fusions between the *P. haemolytica* leukotoxin gene and a nucleotide sequence encoding a selected antigen. These constructs produce a chimeric protein that displays enhanced immunogenicity when compared to the immunologic reaction elicited by administration of the antigen alone.

In one embodiment, the present invention is directed to an immunological carrier system comprising an immunogenic chimeric protein. The chimeric protein comprises a leukotoxin polypeptide fused to a selected antigen, whereby the leukotoxin portion of the chimeric protein acts to increase the immunogenicity of the antigen. In particularly preferred embodiments, the selected antigen is somatostatin (SRIF), gonadotropin releasing hormone (GnRH) or rotavirus viral protein 4 (VP4).

Also disclosed are vaccine compositions comprising the chimeric proteins and a pharmaceutically acceptable vehicle and methods of using the same.

In another embodiment, the subject invention is directed to DNA constructs encoding the chimeric proteins. The DNA constructs comprise a first nucleotide sequence encoding a leukotoxin polypeptide operably linked to a second nucleotide sequence encoding the selected antigen.

In yet another embodiment, the subject invention is directed to expression cassettes comprised of (a) the DNA constructs above and (b) control sequences that direct the transcription of the construct whereby the constructs can be transcribed and translated in a host cell.

In another embodiment, the invention is directed to host cells transformed with these expression cassettes.

Another embodiment of the invention provides a method of producing a recombinant polypeptide. The method comprises (a) providing a population of host cells described above and (b) growing the population of cells under conditions whereby the polypeptide encoded by the expression cassette is expressed.

These and other embodiments of the present invention will readily occur to those of ordinary skill in the art in view of the disclosure herein.

BRIEF DESCRIPTION OF THE FIGURES

FIGS. 3A through 3I (SEQ ID NOS:1 and 2) shows the nucleotide sequence and predicted amino acid sequence of leukotoxin 352 (LKT 352) from plasmid pAA352. Both the structural gene for LKT 352 and the sequences of the flanking vector regions are shown.

FIG. 4 (SEQ ID NOS:3–8) shows the nucleotide sequences of SRIF, GnRH and bovine rotavirus VP4, used in the construction of the leukotoxin-antigen gene fusions.

FIGS. 6A through 6J (SEQ ID NOS:9 and 10) the nucleotide sequence and predicted amino acid sequence of the LKT-SRIF chimeric protein from pAA496.

FIGS. 8A through 8J (SEQ ID NOS:11 and 12) the nucleotide sequence and predicted amino acid sequence of the LKT-GnRH chimeric protein from pAA502.

FIGS. 10A through 10J (SEQ ID NOS:13 and 14) the nucleotide sequence and predicted amino acid sequence of the LXT-VP4 chimeric protein from pAA501.

DETAILED DESCRIPTION

Figure 1:
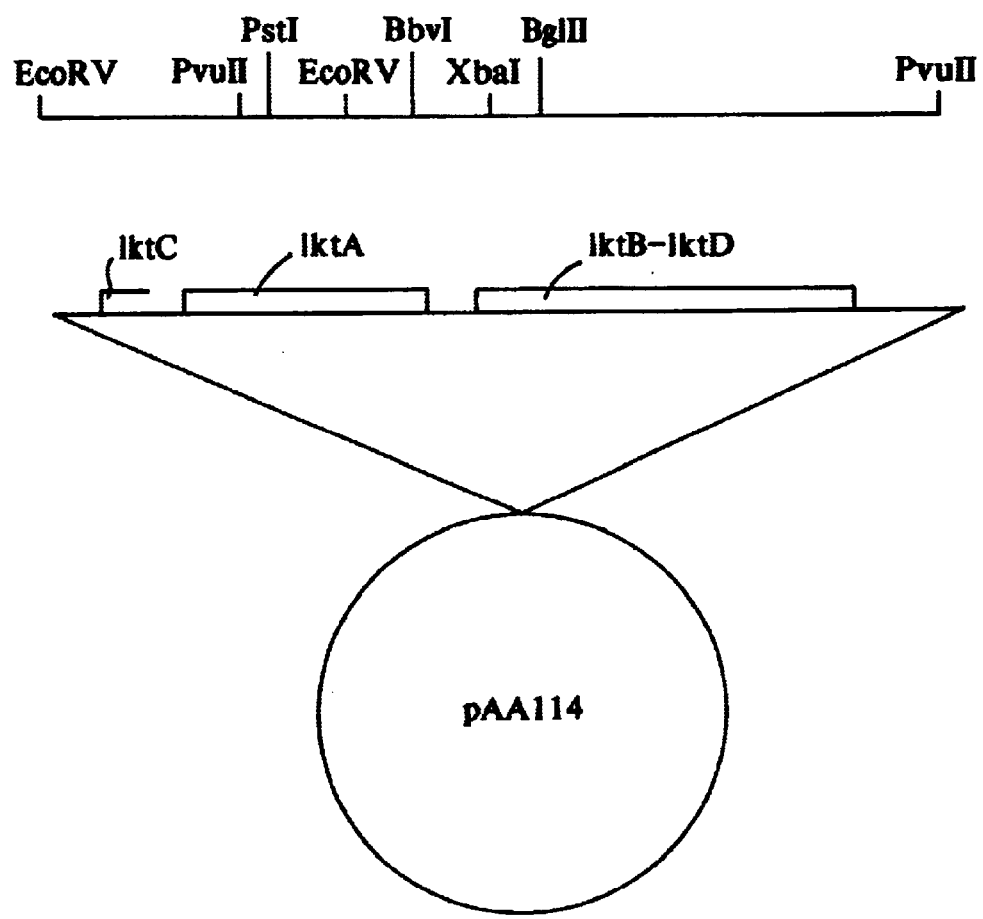
FIG. 1 depicts the structure of the leukotoxin gene of *P. haemolytica* cloned in *E. coli* (Plasmid pAA114).

The practice of the present invention will employ, unless otherwise indicated, conventional techniques of molecular biology, microbiology, virology, recombinant DNA technology, and immunology, which are within the skill of the art. Such techniques are explained fully in the literature. See, e.g., Sambrook, an Fritsch & Maniatis, *Molecular Clonina: A Laboratory Manual*, Second Edition (1989); Maniatis, Fritsch & Sambrook, *Molecular Clonina: A Laboratory Manual* (1982); *DNA Cloning*, Vols. I and II (D. N. Glover ed. 1985); *Oligonucleotide Synthesis* (M. J. Gait ed. 1984); *Nucleic Acid Hybridization* (B. D. Hames & S. J. Higgins eds. 1984); *Animal Cell Culture* (R. K. Freshney ed. 1986); *Immobilized Cells and Enzymes* (IRL press, 1986); B. Perbal, *A Practical Guide to Molecular Cloning* (1984); the series, *Methods In Enzymology* (S. Colowick and N. Kaplan eds., Academic Press, Inc.); and *Handbook of Experimental Immunology*, Vols. I–IV (D. M. Weir and C. C. Blackwell eds., 1986, Blackwell Scientific Publications).

All patents, patent applications, and publications mentioned herein, whether supra or infra, are hereby incorporated by reference in their entirety.

A. Definitions

In describing the present invention, the following terms will be employed, and are intended to be defined as indicated below.

An "antigen" refers to a molecule containing one or more epitopes that will stimulate a host's immune system to make a humoral and/or cellular antigen-specific response. The term is also used interchangeably with "immunogen." An antigen will include one or more epitopes from a protein molecule, such as but not limited to, bacterial and viral proteins, as well as peptide hormones which elicit an immune response. Additionally, an antigen can comprise one or more identical or different immunogenic repeating sequences of a protein. Specifically excluded from the definition for purposes of this application are cytokines such as interleukin-1 (IL1 ), interleukin-2 (IL2), interleukin-3 (IL3), interleukin-4 (IL4), and gamma-interferon (γIFN).

The term "leukotoxin polypeptide" intends a polypeptide derived from a protein belonging to the family of molecules characterized by the carboxy-terminus consensus amino acid sequence Gly-Gly-X-Gly-X-Asp (Highlander et al., *DNA* (1989) 8:15–28), where X is Lys, Asp(SEQ ID NOS:15), val or Asn. Such proteins include., among others, leukotoxins derived from *P. haemolytica* and *Actinobacillus pleuropneumoniae*, as well as *E. coli* alpha hemolysin (Strathdee, C. A., and Lo, R. Y. C. *Infect. Immun.* (1987) 55:3233–3236; Lo, R. Y. C., *Can. J. Vet. Res.* (1990) 54:S33–35; Welch, R. A., *Mol. Microbiol.* (1991) 5:521–528). This family of toxins is known as the "RTX" family of toxins (Lo, R. Y. C., *Can. J. Vet. Res.* (1990) 54:533–535). In addition, the term "leukotoxin polypeptide" refers to a leukotoxin polypeptide which is chemically synthesized, isolated from an organism expressing the same, or recombinantly produced. Furthermore, the term intends an immunogenic protein having an amino acid sequence substantially homologous to a contiguous amino acid sequence found in the particular native leukotoxin molecule. Thus, the term includes both full-length and partial sequences, as well as analogs. Although native full-length leukotoxins display leukotoxic activity, the term "leukotoxin" also intends molecules which remain immunogenic yet lack the cytotoxic character of native leukotoxins. The nucleotide sequences and corresponding amino acid sequences for several leukotoxins are known.

See, e.g., U.S. Pat. Nos. 4,957,739 and 5,055,400; Lo et al., *Infect. Immun.* (1985) 50:667–67; Lo et al., *Infect. Immun.* (1987) 55:1987–1996; Strathdee, C. A., and Lo, R. Y. C., *Infect. Immun.* (1987) 55:3233–3236; Highlander et al., *DNA* (1989) 8:15–28; Welch, R. A., *Mol. Microbial.* (1991) 5:521–528.

Figure 2:
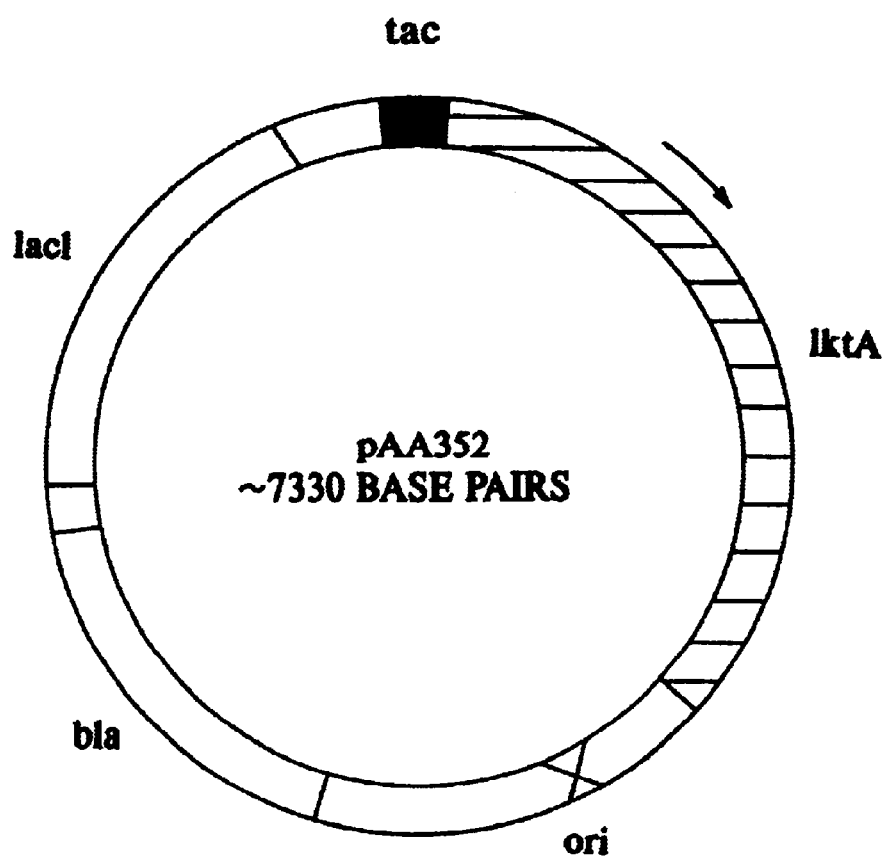
FIG. 2 depicts the structure of Plasmid pAA352 wherein tac is the hybrid trp::lac promoter from *E. coli*; bla represents the β-lactamase gene (ampicillin resistance); ori is the ColEl-based plasmid origin of replication; lktA is the *P. haemolytica* leukotoxin structural gene; and lacl is the *E. coli* lac operon repressor. The direction of transcription/translation of the leukotoxin gene is indicated by the arrow. The size of each component is not drawn to scale.

By "LKT 352" is meant a protein which is derived from the lktA gene present in plasmid pAA352 (FIG. 2, ATCC Accession No. 68283). The nucleotide sequence and corresponding amino acid sequence of this gene are described in International Publication No. W091/15237 and shown in FIG. 3A through 3I (SEQ ID NOS:1 and 2). The gene encodes a truncated leukotoxin, having 931 amino acids, which lacks the cytotoxic portion of the molecule. The derived LKT 352 is not necessarily physically derived from the sequence present in plasmid pAA352. Rather, it may be generated in any manner, including for example, by chemical synthesis or recombinant production. In addition, the amino acid sequence of the protein need only be substantially homologous to the depicted sequence. Thus, sequence variations may be present so long as the protein functions to enhance the immunogenicity of the antigen with which it is associated.

A "hapten" is a molecule containing one or more epitopes that does not stimulate a host's immune system to make a humoral or cellular response unless linked to a carrier.

The term "epitope" refers to the site on an antigen or hapten to which a specific antibody molecule binds. The term is also used interchangeably with "antigenic determinant" or "antigenic determinant site."

An "immunological response" to an antigen or vaccine is the development in the host of a cellular and/or antibody-mediated immune response to the composition or vaccine of interest. Usually, such a response includes but is not limited to one or more of the following effects; the production of antibodies, B cells, helper T cells, suppressor T cells, and/or cytotoxic T cells and/or γδ T cells, directed specifically to an antigen or antigens included in the composition or vaccine of interest.

An "immunogenic protein" or "immunogenic amino acid sequence" is a protein or amino acid sequence, respectively, which elicits an immunological response in a subject to which it is administered.

A leukotoxin-antigen chimera displays "increased immunogenicity" when it possesses a greater capacity to elicit an immune response than the corresponding antigen alone. Such increased immunogenicity can be determined by administering the particular leukotoxin-antigen and antigen controls to animals and comparing antibody titers against the two using standard assays such as radioimmunoassays and ELISAs, well known in the art.

By "carrier system" is meant a system which includes a molecule that serves to increase the immunogenicity of an antigen administered therewith, as defined above. Without being bound by any particular theory, the molecule may function to increase the immunogenicity of the antigen by presenting the same to cells of the immune system, such as antigen presenting cells, macrophages, follicular dendritic cells, B cells and T cells; or by stimulating the immune system to respond at a level greater than that observed when the antigen is administered alone.

By "subunit antigen composition" is meant a composition containing at least one immunogenic polypeptide, but not all antigens, derived from or homologous to an antigen from a pathogen of interest. Such a composition is substantially free of intact pathogen cells or particles. Generally, a "subunit antigen composition" is prepared from at least partially purified (preferably substantially purified) immunogenic polypeptides from the pathogen, or recombinant analogs thereof.

The term "protein" is used herein to designate a naturally occurring polypeptide. The term "polypeptide" is used in its broadest sense, i.e., any polymer of amino acids (dipeptide or greater) linked through peptide bonds. Thus, the term "polypeptide" includes proteins, oligopeptides, protein fragments, analogs, muteins, fusion proteins and the like.

"Native" proteins or polypeptides refer to proteins or polypeptides recovered from a source occurring in nature. Thus, the term "native leukotoxin" would include naturally occurring leukotoxin and fragments thereof.

"Recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

A "rotavirus VP6 protein" refers to the art-recognized major viral protein of the inner capsid from any species or strain within the family Reoviridae. See, e.g., Kapikian et al., 1985. Examples of rotavirus strains from which the VP6 protein can be isolated and employed in the present invention include, but are not limited to., Simian SA-11, human D rotavirus, bovine UK rotavirus, human Wa or W rotavirus, human DS-1 rotavirus, rhesus rotavirus, the "O" agent, bovine NCDV rotavirus, human S2 rotavirus, human KUN rotavirus, human 390 rotavirus, human P rotavirus, human N rotavirus, human Walk 57/14 rotavirus, human Mo rotavirus, human Ito rotavirus, human Nemoto rotavirus, human YO rotavirus, human McM2 rotavirus, rhesus monkey MMU18006 rotavirus, canine CU-1 rotavirus, feline Taka rotavirus, equine H-2 rotavirus, human St. Thomas No. 3 and No. 4 rotaviruses, human Hosokawa rotavirus, human Hochi rotavirus, porcine SB-2 rotavirus, porcine Gottfried rotavirus, porcine SB-1A rotavirus, porcine OSU rotavirus, equine H-1 rotavirus, chicken Ch.2 rotavirus, turkey Ty.1 rotavirus, bovine C486 rotavirus, and strains derived from them. Thus the present invention encompasses the use of VP6 from any rotavirus strain, whether from subgroup I, subgroup II, or any as yet unidentified subgroup, as well as from any of the serotypes 1–7, as well as any as yet unidentified serotypes. Such VP6 proteins can be used as immunologic carriers of polypeptides. These carrier molecules comprise amino acid sequences of rotavirus VP6 amino acid sequences which are unique to the class, or any member of the class, of VP6 polypeptides. Such unique sequences of VP6 proteins are referred to as a "rotavirus VP6 inner capsid protein amino acid sequence." VP6 carriers are further disclosed in U.S. Pat. No. 5,071,651, incorporated herein by reference in its entirety.

A carrier that is "substantially homologous to a rotavirus VP6 inner capsid protein or a functional fragment thereof" is one in which at least about 85%, preferably at least about 90%, and most preferably at least about 95%, of the amino acids match over a defined length of the molecule. A "functional fragment" of a rotavirus VP6 inner capsid protein is a fragment with the capability of acting as a carrier molecule for the novel chimeric proteins of the instant invention.

A "replicon" is any genetic element (e.g., plasmid, chromosome, virus) that functions as an autonomous unit of DNA replication in vivo or in vitro; i.e., capable of replication under its own control.

A "vector" is a replicon, such as a plasmid, phage, or cosmid, to which another DNA segment may be attached so as to bring about the replication of the attached segment.

A "double-stranded DNA molecule" refers to the polymeric form of deoxyribonucleotides in a double-stranded helix, both relaxed and supercoiled. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having the sequence homologous to the mRNA).

A DNA "coding sequence" or a "nucleotide sequence encoding" a particular protein, is a DNA sequence which is transcribed and translated into a polypeptide in vivo or in vitro when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences, cDNA from eucaryotic IRNA, genomic DNA sequences from eucaryotic (e.g., mammalian) DNA, and even synthetic DNA sequences. A transcription termination sequence will usually be located 3' to the coding sequence.

A "promoter sequence" is a DNA regulatory region capable of binding RNA polymerase in a cell and initiating transcription of a downstream (3' direction) coding sequence. For purposes of defining the present invention, the promoter sequence is bound at the 3' terminus by the translation start codon (ATG) of a coding sequence and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eucaryotic promoters will often, but not always, contain "TATA" boxes and "CAT" boxes. Procaryotic promoters contain Shine-Dalgarno sequences in addition to the -10 and -35 consensus sequences.

DNA "control sequences" refers collectively to promoter sequences, ribosome binding sites, polyadenylation signals, transcription termination sequences, upstream regulatory domains, enhancers, and the like, which collectively provide for the transcription and translation of a coding sequence in a host cell.

A coding sequence is "operably linked to" another coding sequence when RNA polymeras will transcribe the two coding sequences into mMA, which is then translated into a chimeric polypeptide encoded by the two coding sequences. The coding sequences need not be contiguous to one another so long as the transcribed sequence is ultimately processed to produce the desired chimeric protein.

A control sequence "directs the transcription" of a coding sequence in a cell when RNA polymerase will bind the promoter sequence and transcribe the coding sequence into mRNA, which is then translated into the polypeptide encoded by the coding sequence.

A "host cell" is a cell which has been transformed, or is capable of transformation, by an exogenous DNA sequence.

A cell has been "transformed" by exogenous DNA when such exogenous DNA has been introduced inside the cell membrane. Exogenous DNA may or may not be integrated (covalently linked) to chromosomal DNA making up the genome of the cell. In procaryotes and yeasts, for example, the exogenous DNA may be maintained on an episomal element, such as a plasmid. With respect to eucaryotic cells, a stably transformed cell is one in which the exogenous DNA has become integrated into the chromosome so that it is inherited by daughter cells through chromosome replication. This stability is demonstrated by the ability of the eucaryotic cell to establish cell lines or clones comprised of a population of daughter cell containing the exogenous DNA.

A "clone" is a population of cells derived from a single cell or common ancestor by mitosis. A "cell line" is a clone of a primary cell that is capable of stable growth in vitro for many generations.

Two DNA or polypeptide sequences are "substantially homologous" when at least about 80% (preferably at least about 90%, and most preferably at least about 95%) of the nucleotides or amino acids match over a defined length of the molecule. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning,* vols I & II, supra; *Nucleic Acid Hybridization,* supra.

The term "functionally equivalent" intends that the amino acid sequence of the subject fusion protein is one that will elicit an immunological response, as defined above, equivalent to an unmodified immunogenic leukotoxin-antigen chimeric protein.

A "heterologous" region of a DNA construct is an identifiable segment of DNA within or attached to another DNA molecule that is not found in association with the other molecule in nature. Thus, when the heterologous region encodes a bacterial gene, the gene will usually be flanked by DNA that does not flank the bacterial gene in the genome of the source bacteria. Another example of the heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

A composition containing A is "substantially free of" B when at least about 85% by weight of the total of A+B in the composition is A. Preferably, A comprises at least about 90% by weight of the total of A+B in the composition, more preferably at least about 95%, or even 99% by weight.

The term "treatment" as used herein refers to either (i) the prevention of infection or reinfection (prophylaxis), or (ii) the reduction or elimination of symptoms or the disease of interest (therapy).

B. General Methods

Central to the instant invention is the discovery that leukotoxin polypeptides, when coupled to selected antigens, are able to increase the immunogenicity of the antigen as compared to the immunogenicity of the antigen when presented alone. Thus, leukotoxin polypeptides can act as carrier proteins for the presentation of a desired antigen to the immune system. Accordingly, the chimeric proteins can be formulated into vaccine compositions which provide enhanced immunogenicity to the antigen presented therewith. The fusion of the leukotoxin gene to the selected antigen further functions to facilitate purification of the chimeric protein from cells expressing the same.

The leukotoxin carrier is especially useful for the presentation of small or endogenous peptide antigens, including peptide hormones, and bacterial and viral antigens, which typically elicit poor immune responses when presented without the aid of a carrier. Exemplified herein are leukotoxin chimeras which include leukotoxin fused to small peptide hormones—somatostatin (SRIF) and gonadatropin releasing hormone (GnRH). SRIF-14 has 14 amino acids and GnRH possesses 10 amino acids. The nucleotide sequences of SRIF and GnRH are depicted in FIG. 4(SEQ ID NOS:3–8). Because the sequences are relatively short, they can easily be generated using synthetic techniques, as described further below. Because these hormones are small in size and are endogenous to several mammals such as humans, bovines etc., these substances require the use of carrier proteins in order to elicit an adequate immune response in such mammals. Immunization with these hormones can regulate growth rate, lactation and reproductive efficiency. A detailed discussion of SRIF can be found in U.S. Pat. No. 5,212,156, filed Jun. 18, 1990, which is incorporated herein by reference in its entirety. GnRH is further discussed in U.S. Pat. No. 4,975,420, incorporated herein by reference in its entirety.

Also exemplified herein is a chimera comprised of leukotoxin and bovine rotavirus viral protein 4 (VP4). VP4 (molecular weight 86,719), functions as the viral hamagglutinin and forms the spike-like projections protruding from the surface of the virus. Antibodies capable of neutralizing the virus bind to the tip of the spike. VP4 appears to play a major role in viral attachment during infection. The nucleotide sequence of VP4 is depicted in FIG. 4. For a further discussion of rotavirus infection and VP4, see, Redmond, M. J. et al. in *Viral Diseases* (Ed. E. Kurstak, Marcel Dekker, New York, 1991, pp. 387–404); and International Publication No. WO/9207941, published May 14, 1992, both incorporated herein by reference in their entirety. Although the invention is described with respect to these particular proteins, leukotoxin polypeptides, or proteins functionally equivalent and substantially homologous thereto, can be easily fused to other antigens, based on the disclosure herein, in order to increase the immunogenicity thereof.

The leukotoxin-antigen complex can be conveniently produced recombinantly as a chimeric protein. The antigen portion of the chimera can be fused either 5' or 3' to the leukotoxin portion of the molecule.

Actively growing cells of *P. haemolytica* have been shown to secrete leukotoxin which can be cloned, the gene encoding the same isolated, and fused with a gene encoding a desired antigen, using techniques well known in the art. The resulting chimeric proteins can be expressed and used to immunize subjects against the particular antigen fused to leukotoxin.

The nucleotide sequence coding for full-length *P. haemolytica* Al leukotoxin has been determined. See, e.g., Lo, R. Y. C. *Infect. Immun.* (1987) 55:1987–1996; U.S. Pat. No. 5,055,400, incorporated herein by reference in its entirety. *P. haemolytica* leukotoxin can be produced using recombinant techniques and purified from, for example, bacterial cells. The leukotoxin can also be purified from native bacteria using immunoadsorbent chromatography.

Similarly, the coding sequences for numerous antigens are known or can be determined. Again, these antigens can be purified using standard techniques.

Purification of the above proteins, using standard techniques including those described herein, permits the sequencing of the same by any of the various methods known to those skilled in the art. For example, the amino acid sequences can be determined by repetitive cycles of Edman degradation, followed by amino acid analysis by HPLC. Other methods of amino acid sequencing are also known in the art. Furthermore, fragments of the proteins can be tested for biological activity and active epitopes used in compositions in lieu of the entire protein.

Once the amino acid sequences are determined, oligonucleotide probes which contain the codons for a portion of the determined amino acid sequences can be prepared and used to screen DNA libraries for genes encoding the subject proteins. The basic strategies for preparing oligonucleotide probes and DNA libraries, as well as their screening by nucleic acid hybridization, are well known to those of ordinary skill in the art. See, e.g., *DNA Cloninga:* Vol. I, supra; *Nucleic Acid Hybridization,* supra; *Oligonucleotide Synthesis,* supra; T. Maniatis et al., supra.

First, a DNA library is prepared. The library can consist of genomic DNA from *P. haemolytica* (for the isolation of the leukotoxin gene) or from appropriate cells or viruses (for the isolation of the desired antigen gene). Once the library is constructed, oligonucleotides to probe the library are prepared and used to isolate the gene encoding the desired protein. The oligonucleotides are synthesized by any appropriate method. The particular nucleotide sequences selected are chosen so as to correspond to the codons encoding a known amino acid sequence from the desired protein. Since the genetic code is degenerate, it will often be necessary to synthesize several oligonucleotides to cover all, or a reasonable number, of the possible nucleotide sequences which encode a particular region of the protein. Thus, it is generally preferred in selecting a region upon which to base the probes, that the region not contain amino acids whose codons are highly degenerate. In certain circumstances, one of skill in the art may find it desirable to prepare probes that are fairly long, and/or encompass regions of the amino acid sequence which would have a high degree of redundancy in corresponding nucleic acid sequences, particularly if this lengthy and/or redundant region is highly characteristic of the protein of interest. It may also be desirable to use two probes (or sets of probes), each to different regions of the gene, in a single hybridization experiment. Automated oligonucleotide synthesis has made the preparation of large families of probes relatively straight-forward. While the exact length of the probe employed is not critical, generally it is recognized in the art that probes from about 14 to about 20 base pairs are usually effective. Longer probes of about 25 to about 60 base pairs are also used.

The selected oligonucleotide probes are labeled with a marker, such as a radionucleotide or biotin, using standard procedures. The labeled set of probes is then used in the screening step, which consists of allowing the single-stranded probe to hybridize to isolated ssDNA from the library, according to standard techniques. Either stringent or permissive hybridization conditions could be appropriate, depending upon several factors, such as the length of the probe and whether the probe is derived from the same species as the library, or an evolutionarily close or distant species. The selection of the appropriate conditions is within the skill of the art. See, generally, *Nucleic Acid hybridization,* supra. The basic requirement is that hybridization conditions be of sufficient stringency so that selective hybridization occurs; i.e., hybridization is due to a sufficient degree of nucleic acid homology (e.g., at least about 75%), as opposed to nonspecific binding. Once a clone from the screened library has been identified by positive hybridization, it can be confirmed by restriction enzyme analysis and DNA sequencing that the particular library insert contains a gene for the desired protein.

Alternatively, DNA sequences encoding the proteins of interest can be prepared synthetically rather than cloned. The DNA sequence can be designed with the appropriate codons for the particular amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, *Nature* (1981) 292:756; Nambair et al. *Science* (1984) 223:1299; Jay et al. *J. Biol. Chem.* (1984) 259:6311.

Once coding sequences for the desired proteins have been prepared or isolated, they can be cloned into any suitable vector or replicon. Numerous cloning vectors are known to those of skill in the art, and the selection of an appropriate cloning vector is a matter of choice. Examples of recombinant DNA vectors for cloning and host cells which they can transform include the bacteriophage lambda (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (Bacillus), pIJ61 (Streptomyces), pUC6 (Streptomyces), YIp5 (Saccharomyces), YCp19 (Saccharomyces) and bovine papilloma virus (mammalian cells). See, generally, *DNA Cloning:* Vols. I & II, supra; T. Maniatis et al., supra; B. Perbal, supra.

Suitable restriction enzymes can then be employed to isolate the appropriate antigen gene or leukotoxin gene and these sequences can be ligated together and cloned to form a leukotoxin-antigen fusion gene.

The fusion gene can be placed under the control of a promoter, ribosome binding site (for bacterial expression) and, optionally, an operator (collectively referred to herein as "control" elements), so that the DNA sequence encoding the chimeric protein is transcribed into RNA in the host cell transformed by a vector containing this expression construction. The coding sequence may or may not contain a signal peptide or leader sequence. The chimeric proteins of the present invention can be expressed using, for example, native *P. haemolytica* promoter, the *E. coli* tac promoter or the protein A gene (spa) promoter and signal sequence. Leader sequences can be removed by the bacterial host in post-translational processing. See, e.g., U.S. Pat. Nos. 4,431,739; 4,425,437; 4,338,397.

In addition to control sequences, it may be desirable to add regulatory sequences which allow for regulation of the expression of the protein sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

An expression vector is constructed so that the particular fusion coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the sequences encoding the particular chimeric protein of interest may be desirable to achieve this end. For example, in some cases it may be necessary to modify the sequence so that it may be attached to the control sequences with the appropriate orientation; i.e., to maintain the reading frame. The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases, it may be desirable to add sequences which cause the secretion of the polypeptide from the host organism, with subsequent cleavage of the secretory signal.

It may also be desirable to produce mutants or analogs of the chimeric proteins of interest. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., T. Maniatis et al., supra; *DNA Cloning*, Vols. I and II, supra; *Nucleic Acid Hybridization*, supra.

A number of procaryotic expression vectors are known in the art. See, e.g., U.S. Pat. Nos. 4,440,859; 4,436,815; 4,431,740; 4,431,739; 4,428,941; 4,425,437; 4,418,149; 4,411,994; 4,366,246; 4,342,832; see also U.K. Patent Applications GB 2,121,054; GB 2,008,123; GB 2,007,675; and European Patent Application 103,395. Yeast expression vectors are also known in the art. See, e.g., U.S. Pat. Nos. 4,446,235; 4,443,539; 4,430,428; see also European Patent Applications 103,409; 100,561; 96,491.

Depending on the expression system and host selected, the proteins of the present invention are produced by growing host cells transformed by an expression vector described above under conditions whereby the protein of interest is expressed. The chimeric protein is then isolated from the host cells and purified. If the expression system secretes the protein into growth media, the protein can be purified directly from the media. If the protein is not secreted, it is isolated from cell lysates. The selection of the appropriate growth conditions and recovery methods are within the skill of the art.

An alternative method to identify proteins of the present invention is by constructing gene libraries, using the resulting clones to transform *E. coli* and pooling and screening individual colonies using polyclonal serum or monoclonal antibodies to the desired antigen.

The chimeric proteins of the present invention may also be produced by chemical synthesis such as solid phase peptide synthesis, using known amino acid sequences or amino acid sequences derived from the DNA sequence of the genes of interest. Such methods are known to those skilled in the art. Chemical synthesis of peptides may be preferable if a small fragment of the antigen in question is capable of raising an immunological response in the subject of interest.

The proteins of the present invention or their fragments can be used to produce antibodies, both polyclonal and monoclonal. If polyclonal antibodies are desired, a selected mammal, (e.g., mouse, rabbit, goat, horse, etc.) is immunized with an antigen of the present invention, or its fragment, or a mutated antigen. Serum from the immunized animal is collected and treated according to known procedures. If serum containing polyclonal antibodies is used, the polyclonal antibodies can be purified by immunoaffinity chromatography, using known procedures.

Monoclonal antibodies to the proteins of the present invention, and to the fragments thereof, can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. See, e.g., M. Schreier et al., *Hybridoma Techniques* (1980); Hammerling et al., *Monoclonal Antibodies and T-cell Hybridomas* (1981); Kennett et al., *Monotonal Antibodies* (1980); see also U.S. Pat. Nos. 4,341,761; 4,399,121; 4,427,783; 4,444,887; 4,452,570; 4,466,917; 4,472,500, 4,491,632; and 4,493,890. Panels of monoclonal antibodies produced against the antigen of interest, or fragment thereof, can be screened for various properties; i.e., for isotype, epitope, affinity, etc. Monoclonal antibodies are useful in purification, using immunoaffinity techniques, of the individual antigens which they are directed against.

Animals can be immunized with the compositions of the present invention by administration of the chimeric protein, or an active fragment thereof, or an analog thereof. The chimeric protein can consist of leukotoxin fused to an epitope of the desired antigen, as defined above. Thus, if the fragment or analog of the fusion protein is used, it will include the amino acid sequence of leukotoxin, or a fragment of the same which interacts with the immune system to increase the immunogenicity of the antigen or epitope thereof, linked to the antigen of interest.

Prior to immunization, it may be desirable to further increase the immunogenicity of the particular chimeric protein, or an analog of the protein, or particularly fragments of the protein. This can be accomplished in any one of several ways known those of skill in the art. For example, the antigenic peptide may be administered linked to a carrier, in addition to the leukotoxin carrier. For example, a fragment may be conjugated with a macromolecular carrier. Suitable carriers are typically large, slowly metabolized macro-molecules such as: proteins; polysaccharides, such as sepharose, agarose, cellulose, cellulose beads and the like; polymeric amino acids such as polyglutamic acid, polylysine, and the like; amino acid copolymers; and inactive virus particles. Especially useful protein substrates are serum albumins, keyhole limpet hemocyanin, immunoglobulin molecules, thyroglobulin, ovalbumin, and other proteins well known to those skilled in the art.

The protein substrates may be used in their native form or their functional group content may be modified by, for example, succinylation of lysine residues or reaction with Cys-thiolactone. A sulfhydryl group may also be incorporated into the carrier (or antigen) by, for example, reaction of amino functions with 2-iminothiolane or the N-hydroxysuccinimide ester of 3-(4-dithiopyridyl propionate. Suitable carriers may also be modified to incorporate spacer arms (such as hexamethylene diamine or other bifunctional molecules of similar size) for attachment of peptides.

Other suitable carriers for the chimeric proteins of the present invention include VP6 polypeptides of rotaviruses, or functional fragments thereof, as disclosed in U.S. Pat. No. 5,071,651, and incorporated herein by reference. Also useful is a fusion product of a viral protein and the subject leukotoxin-antigen immunogen made by methods disclosed in U.S. Pat. No. 4,722,840. Still other suitable carriers include cells, such as lymphocytes, since presentation in this form mimics the natural mode of presentation in the subject, which gives rise to the immunized state Alternatively, the fusion proteins of the present invention may be coupled to erythrocytes, preferably the subject's own erythrocytes. Methods of coupling peptides to proteins or cells are known to those of skill in the art.

The novel chimeric proteins of the instant invention can also be administered via a carrier virus which expresses the same. Carrier viruses which will find use with the instant invention include but are not limited to the vaccinia and other pox viruses, adenovirus, and herpes virus. By way of example, vaccinia virus recombinants expressing the novel chimeric proteins can be constructed as follows. The DNA encoding the particular leukotoxin-antigen chimeric protein is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the instant chimeric protein into the viral genome. The resulting TK-recombinant can be selected by culturing the cells in the presence of 5-bromodeoxyuridine and picking viral plaques resistant thereto.

It is also possible to immunize a subject with a protein of the present invention, or an immunogenic fragment thereof, or an analog thereof, which is administered alone, or mixed with a pharmaceutically acceptable vehicle or excipient. Typically, vaccines are prepared as injectables, either as liquid solutions or suspensions; solid forms suitable for solution in, or suspension in, liquid vehicles prior to injection may also be prepared. The preparation may also be emulsified or the active ingredient encapsulated in liposome vehicles. The active immunogenic ingredient is often mixed with vehicles containing excipients which are pharmaceutically acceptable and compatible with the active ingredient. Suitable vehicles are, for example, water, saline, dextrose, glycerol, ethanol, or the like, and combinations thereof. In addition, if desired, the vehicle may contain minor amounts of auxiliary substances such as wetting or emulsifying agents, pH buffering agents, or adjuvants which enhance the effectiveness of the vaccine. Adjuvants may include for example, muranyl dipeptides, avridine, aluminum hydroxide, oils, saponins and other substances known in the art. Actual methods of preparing such dosage forms are known, or will be apparent, to those skilled in the art. See, e.g., Remington's Pharmaceutical Sciences, Mack Publishing Company, Easton, Pa., 15th edition, 1975. The composition or formulation to be administered will, in any event, contain a quantity of the protein adequate to achieve the desired immunized state in the subject being treated.

Additional vaccine formulations which are suitable for other modes of administration include suppositories and, in some cases, aerosol, intranasal, oral formulations, and sustained release formulations. For suppositories, the vehicle composition will include traditional binders and carriers, such as, polyalkaline glycols, or triglycerides. Such suppositories may be formed from mixtures containing the active ingredient in the range of about 0.5% to about 10% (w/w), preferably about 1% to about 2%. Oral vehicles include such normally employed excipients as, for example, pharmaceutical grades of mannitol, lactose, starch, magnesium, stearate, sodium saccharin cellulose, magnesium carbonate, and the like. These oral vaccine compositions may be taken in the form of solutions, suspensions, tablets, pills, capsules, sustained release formulations, or powders, and contain from about10% to about 95% of the active ingredient, preferably about 25% 35 to about 70%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Controlled or sustained release formulations are made by incorporating the chimeric protein into carriers or vehicles such as liposomes, nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures. The chimeric proteins can also be presented using implanted mini-pumps, well known in the art.

Furthermore, the chimeric proteins (or complexes thereof) may be formulated into vaccine compositions in either neutral or salt forms. Pharmaceutically acceptable salts include the acid addition salts (formed with the free amino groups of the active polypeptides) and which are formed with inorganic acids such as, for example, hydrochloric or phosphoric acids, or such organic acids as acetic, oxalic, tartaric, mandelic, and the like. Salts formed from free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

To immunize a subject, th polypeptide of interest, or an immunologically active fragment thereof, is administered parenterally, usually by intramuscular injection in an appropriate vehicle. Other modes of administration, however, such as subcutaneous, intravenous injection and intranasal delivery, are also acceptable. Injectable vaccine formulations will contain an effective amount of the active ingredient in a vehicle, the exact amount being readily determined by one skilled in the art. The active ingredient may typically range from about 1% to about 95% (w/w) of the composition, or even higher or lower if appropriate. The quantity to be administered depends on the animal to be treated, the capacity of the animal's immune system to synthesize antibodies, and the degree of protection desired. With the present vaccine formulations, approximately 1 $\mu$g to 1 $\mu$g, more generally 5 $\mu$g to 100 $\mu$g of antigen per ml of injected solution, should be adequate to raise an immunological response when administered. Other effective dosages can be readily established by one of ordinary skill in the art through routine trials establishing dose response curves. The subject is immunized by administration of the particular antigen or fragment thereof, or analog thereof, in at least one dose, and preferably two doses. Moreover, the animal may be administered as many doses as is required to maintain a state of immunity.

Below are examples of specific embodiments for carrying out the present invention. The examples are offered for illustrative purposes only, and are not intended to limit the scope of the present invention in any way.

Deposits of Strains Useful in Practicing the Invention

A deposit of biologically pure cultures of th following strains was made with the American Type Culture Collection, 12301 Parklawn Drive, Rockville, Md. The accession number indicated was assigned after successful viability testing, and the requisite fees were paid. Access to said cultures will be available during pendency of the patent application to one determined by the Commissioner to be entitled thereto under 37 CFR 1.14 and 35 USC 122. All restriction on availability of said cultures to the public will be irrevocably removed upon the granting of a patent based upon the application. Moreover, the designated deposits will be maintained for a period of thirty (30) years from the date of deposit, or for five (5) years after the last request for the deposit; or for the enforceable life of the U.S. patent, whichever is longer. Should a culture become nonviable or be inadvertently destroyed, or, in the case of plasmid-containing strains, lose its plasmid, it will be replaced with a viable culture(s) of the same taxonomic description.

These deposits are provided merely as a convenience to those of skill in the art, and are not an admission that a deposit is required under 35 USC §112. The nucleic acid sequences of these plasmids, as well as the amino sequences of the polypeptides encoded thereby, are incorporated herein by reference and are controlling in the event of any conflict with the description herein. A license may be required to make, use, or sell the deposited materials, and no such license is hereby granted.

| Strain | Deposit Date | ATCC No. |
|---|---|---|
| *P. haemolytica* serotype 1 B122 | Feb. 1, 1989 | 53863 |
| pAA352 in *E. coli* W1485 | Mar. 30, 1990 | 68283 |

C. Experimental

Materials and Methods

Enzymes were purchased from commercial sources, and used according to the manufacturers' directions. Radionucleotides and nitrocellulose filters were also purchased from commercial sources.

In the cloning of DNA fragments, except where noted, all DNA manipulations were done according to standard procedures. See Sambrook et al., supra. Restriction enzymes, $T_4$ DNA ligase, *E. coli,* DNA polymerase I, Klenow fragment, and other biological reagents were purchased from commercial suppliers and used according to the manufacturers' directions. Double-stranded DNA fragments were separated on agarose gels.

cDNA and genomic libraries were prepared by standard techniques in pUC13 and the bacteriophage lambda gt11, respectively. See DNA CLONING: Vols I and II, supra.

*P. haemolytica* biotype A, serotype 1 ("A1") strain B122 was isolated from the lung of a calf which died of pneumonic pasteurellosis and was stored at −70° C. in defibrinated blood. Routine propagation was carried out on blood agar plates or in brain heart infusion broth (Difco Laboratories, Detroit, Mich.) supplemented with 5% (v/v) horse serum (Gibco Canada Ltd., Burlington, Canada). All cultures were incubated at 37° C.

EXAMPLE 1

Isolation of *P. haemolytica* Leukotoxin Gene

To isolate the leukotoxin gene, gene libraries of *P. haemolytica* A1 (strain B122) were constructed using standard techniques. See, Lo et al., *Infect. Immun.,* supra; *DNA CLONING: Vols. I and II,* supra; and T. MANIATIS et al., supra. A genomic library was constructed in the plasmid vector pUC13 and a DNA library constructed in the bacteriophage lambda gt11. The resulting clones were used to transform *E. coli* and individual colonies were pooled and screened for reaction with serum from a calf which had survived a *P. haemolytica* infection and that had been boosted with a concentrated culture supernatant of *P. haemolytica* to increase anti-leukotoxin antibody levels. Positive colonies were screened for their ability to produce leukotoxin by incubating cell lysates with bovine neutrophils and subsequently measuring release of lactate dehydrogenase from the latter.

Several positive colonies were identified and these recombinants were analyzed by restriction endonuclease mapping.

One clone appeared to be identical to a leukotoxin gene cloned previously. See, Lo et al., *Infect. Immun.,* supra. To confirm this, smaller fragments were recloned and the restriction maps compared. It was determined that approximately 4 kilobase pairs of DNA had been cloned. Progressively larger clones were isolated by carrying out a chromosome walk (5' to 3' direction) in order to isolate full-length recombinants which were approximately 8 kb in length. The final construct was termed pAA114. This construct contained the entire leukotoxin gene sequence. The structure of this plasmid is shown in FIG. 1.

lktA, a MaeI restriction endonuclease fragment from pAA114 which contained the entire leukotoxin gene, was treated with the Klenow fragment of DNA polymerase I plus nucleotide triphosphates and ligated into the Smar site of the cloning vector pUC13. This plasmid was named pAA179. From this, two expression constructs where made in the ptac-based vector pGH432: lac1 digested with SmaI. One, pAA342, consisted of the 5'-AhaIII fragment of the lktA gene while the other, pAA345, contained the entire MaeI fragment described above. The clone pAA342 expressed a truncated leukotoxin peptide at high levels while pAA345 expressed full length leukotoxin at very low levels. Therefore, the 3' end of the lktA gene (StyI BamHI fragment from pAA345) was ligated to StyI BanHI-digested pAA342, yielding the plasmid pAA352. The structure of pAA352 is shown in FIG. 2 and the nucleotide sequence and predicted amino acid sequence of *P. haemloytica* leukotoxin shown in FIGS. 3A through 3J(SEQ ID NOS:1and 2).

EXAMPLE 2

Construction of LXT-antigen Fusions

Figure 5:
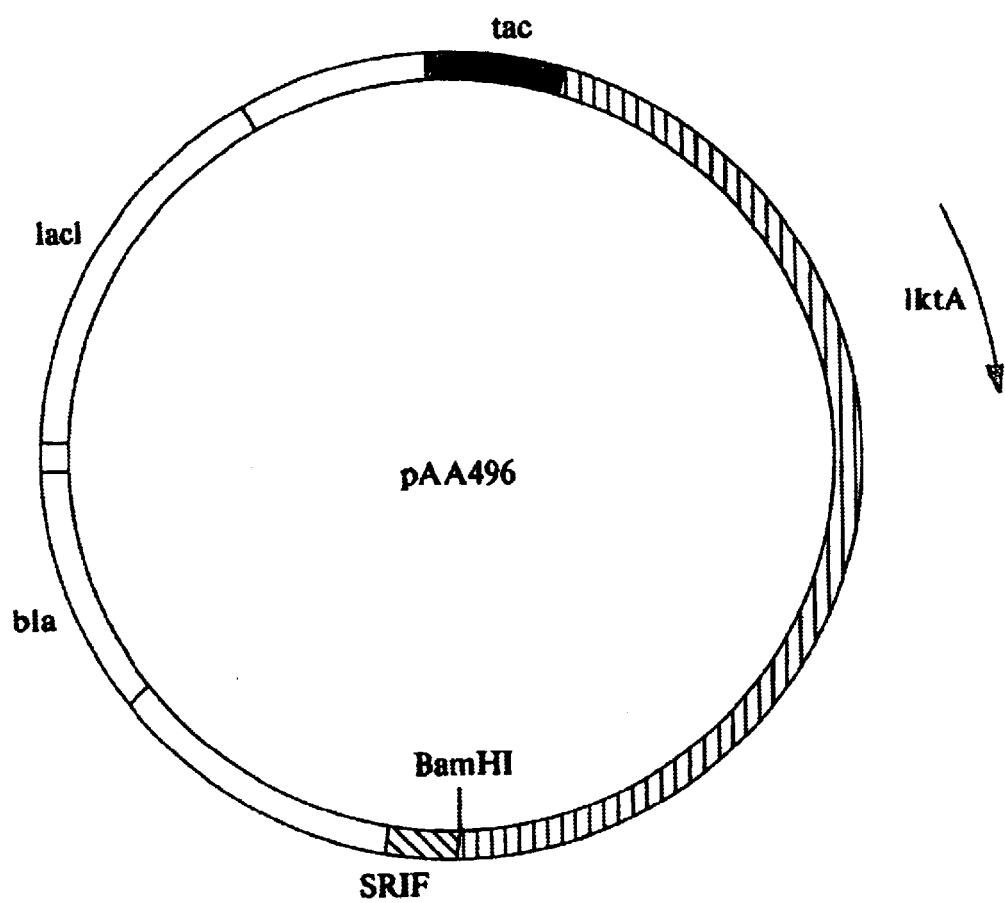
FIG. 5 shows the structure of Plasmid pAA496 carrying a leukotoxin-SRIF (LKT-SRIF) gene fusion wherein tac is the hybrid trp::lac promoter from *E. coli*; bla represents the β-lactamase gene (ampicillin resistance); lktA is the *P. haemolytica* leukotoxin structural gene; SRIF is the somatostatin structural gene; and lacl is the *E. coli* lac operon repressor. The direction of transcription/translation of the leukotoxin gene is indicated by the arrow. The size of each component is not drawn to scale.
Figure 7:
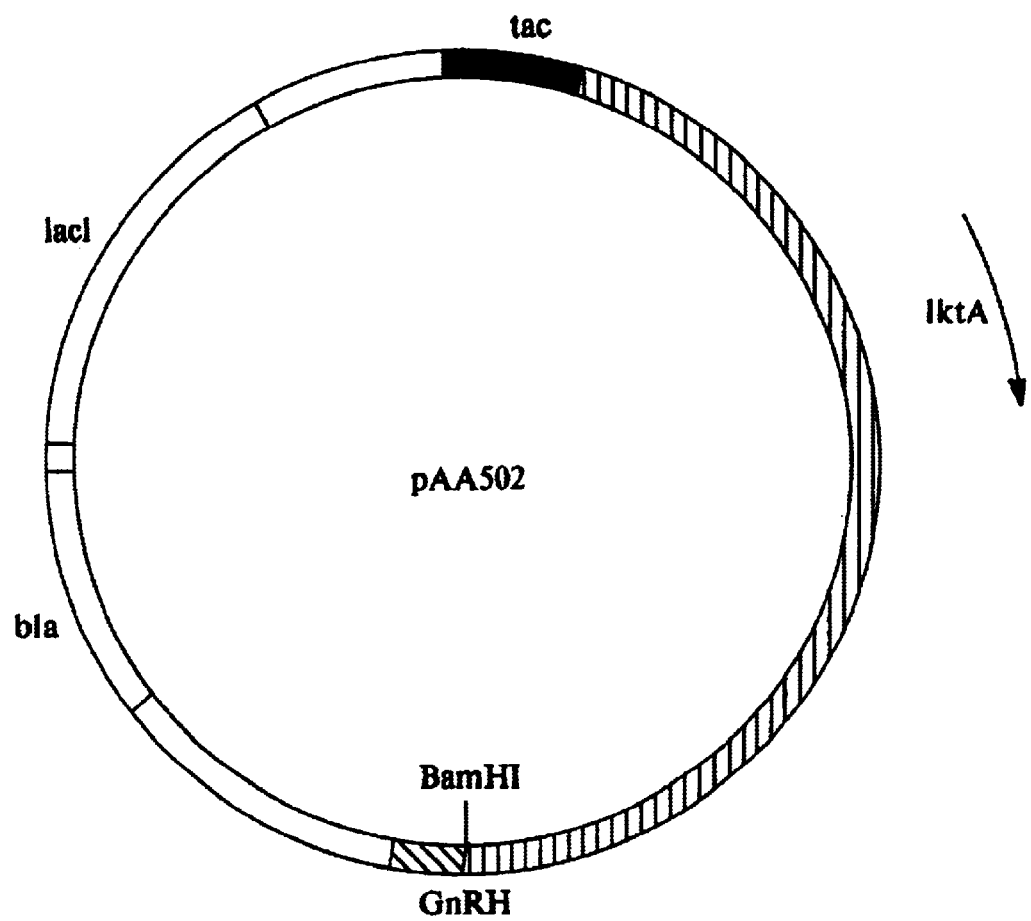
FIG. 7 shows the structure of Plasmid pAA502 carrying a leukotoxin-GnRH (LKT-GnRH) gene fusion wherein tac is the hybrid trp::lac promoter from *E. coli*; bla represents the β-lactamase gene (ampicillin resistance); lktA is the *P. haemolytica* leukotoxin structural gene; GnRH is the gonadotropin releasing hormone structural gene; and lacl is the *E. coli* lac operon repressor. The direction of transcription/translation of the leukotoxin gene is indicated by the arrow. The size of each component is not drawn to scale.
Figure 9:
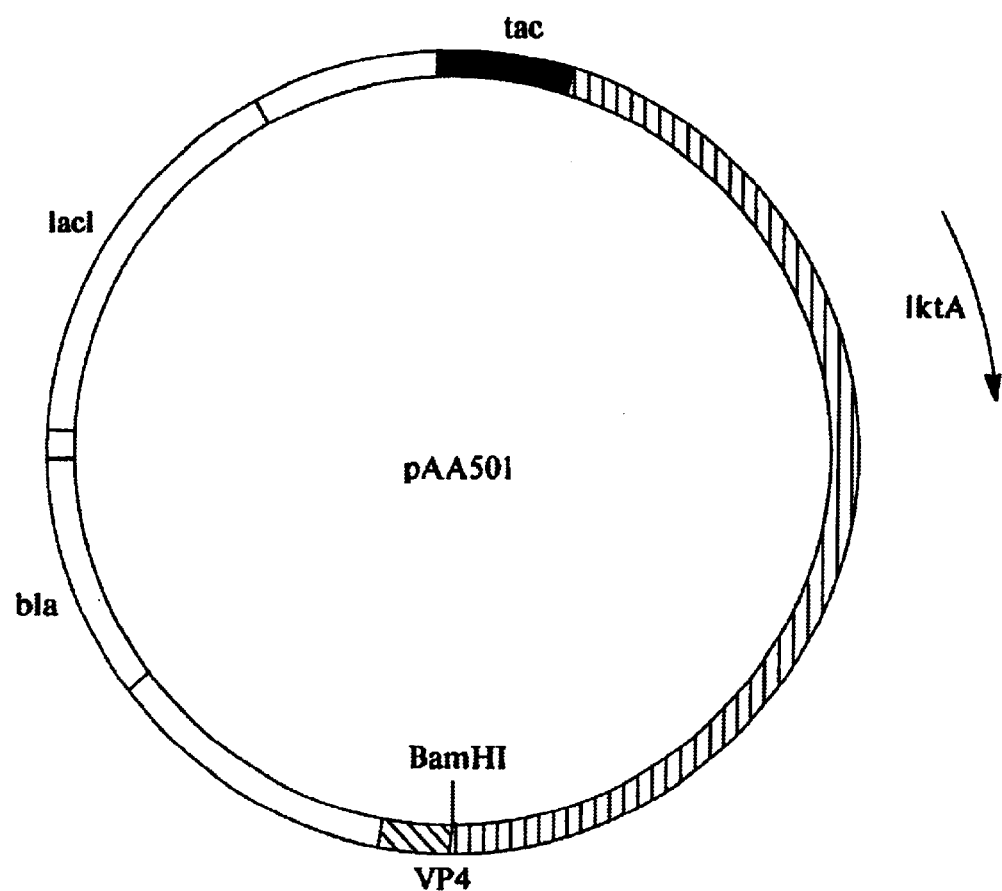
FIG. 9 depicts the structure of Plasmid pAA501 carrying a leukotoxin-VP4 (LKT-VP4) gene fusion wherein tac is the hybrid trp::lac promoter froze *E. coli*; bla represents the β-lactamase gene (ampicillin resistance); lktA is the *P. haemolytica* leukotoxin structural gene; VP4 is the bovine rotavirus viral protein 4 (232–255) structural gene; and lacl is the *E. coli* lac operon repressor. The direction of transcription/translation of the leukotoxin gene is indicated by the arrow. The size of each component is not drawn to scale.

Three representative LXT-antigen fusions were constructed as follows. oligonucleotides containing sequences from the bovine rotavirus VP4, GnRH and SRIF genes were constructed on a Pharmacia Gene Assembler using standard phosphoramidite chemistry. The sequences of these oligonucleotides are shown in FIG. 4 SEQ ID NOS:3–8. The oligonucleotides were annealed and ligated into the vector pAA352 (ATCC No. 68283, and described above), which had been digested with the restriction endonuclease BamH1. This vector contains the *P. haemloytica* leukotoxin gene. The ligated DNA was used to transform *E. coli* strain JM105 (in the case of SRIF) or MH3000 (for VP4 and GnRH). Transformants containing the oligonucleotide inserts were identified by restriction endonuclease mapping. Plasmid DNA from the *E. coli* MH3000 strains was then isolated and used to transform the strain JM105. The recombinant plasmids were designated pAA496 (LKT-SRIF, FIG. 5), pAA502 (LKT-GnRH, FIG. 7), and pAA501 (LKT-VP4, FIG. 9). The nucleotide sequences of these three fusions are shown in FIGS. 6, 8 and 10, respectively.

EXAMPLE 3

Purification of LXT-antigen Fusions

The recombinant LKT-antigen fusions from Example 2 were purified using the following procedure. For each fusion, five to ten colonies of the transformed *E. coli* strains were inoculated into 10 ml of TB broth supplemented with 100 micrograms/ml of ampicillin and incubated at 37° C. for 6 hours on a G10 shaker, 220 rpm. Pour ml of this culture was diluted into each of two baffled Fernbach flasks containing 400 ml of TB broth+ampicillin and incubated overnight as described above. Cells were harvested by centrifugation for 10 minutes at 4,000 rpm in polypropylene bottles, 500 ml volume, using a Sorvall GS3 rotor. The pellet was resuspended in an equal volume of TB broth containing ampicillin which had been prewarmed to 37° C. (i.e., 2×400 ml), and the cells were incubated for 2 hours as described above.

3.2 ml of isopropyl-B,D-thiogalactopyranoside (IPTG, Gibco/BRL), 500 mM in water (final concentration=4 mM), was added to each culture in order to induce synthesis of the recombinant fusion proteins. Cultures were incubated for two hours. Cells were harvested by centrifugation as described above, resuspended in 30 ml of 50 mM Tris-hydrochloride, 25% (w/v) sucrose, pH 8.0, and frozen at −70° C. The frozen cells were thawed at room temperature after 60 minutes at −70° C., and 5 ml of lysozyme (Sigma, 20 mg/ml in 250 mM Tris-HCl, pH 8.0) was added. The mixture was vortexed at high speed for 10 seconds and then placed on ice for 15 minutes. The cells were then added to 500 ml of lysis buffer in a 1000 ml beaker and mixed by stirring with a 2 ml pipette. The beaker containing the lysed cell suspension was placed on ice and sonicated for a total of 2.5 minutes (5–30 second bursts with 1 minute cooling between each) with a Braun sonicator, large probe, set at 100 watts power. Equal volumes of the solution were placed in Teflon SS34 centrifuge tubes and centrifuged for 20 minutes. at 10,000 rpm in a Sorvall SS34 rotor. The pellets were resuspended in a total of 100 ml of sterile double distilled water by vortexing at high speed, and the centrifugation step repeated. Supernatants were discarded and the pellets combined in 20 ml of 10 mM Tris-HCl, 150 MN NaCl, pH 8.0 (Tris-buffered saline) and the suspension frozen overnight at −20° C.

The recombinant suspension was thawed at room temperature and added to 100 ml of 8 M Guanidine HCl (Sigma) in Tris-buffered saline and mixed vigorously. A magnetic stir bar was placed in the bottle and the solubilized sample was mixed at room temperature for 30 minutes. The solution was transferred to a 2000 ml Ehrlenmyer flask and 1200 ml of Tris-buffered saline was quickly added. This mixture was stirred at room temperature for an additional 2 hours. 500 ml aliquots were placed in dialysis bags (Spectrum, 63.7 mm diameter, 6,000–8,000 MW cutoff, #132670, from Fisher scientific) and these were placed in 4,000 ml beakers containing 3,500 ml of Tris-buffered saline+0.5 M Guanidine HCl The beakers were placed in a 40° C. room on a magnetic stirrer overnight after which dialysis buffer was replaced with Tris-buffered saline+0.1 M Guanidine HCl and dialysis continued for 12 hours. The buffer was then replaced with Tris-buffered saline+0.05 M Guanidine HCl and dialysis continued overnight. The buffer was replaced with Tris-buffered saline (no guanidine), and dialysis continued for 12 hours. This was repeated three more times. The final solution was poured into a 2000 ml plastic roller bottle (Corning) and 13 ml of 100 mM PMSF (in ethanol) was added to inhibit protease activity. The solution was stored at −200° C. in 100 ml aliquots.

To confirm that the fusion proteins had been isolated, aliquots of each preparation were diluted 20-fold in double distilled water, mixed with an equal volume of SDS-PAGE sample buffer, placed in a boiling water bath for five minutes and run through 12% polyacrylamide gels. Recombinant leukotoxin controls were also run. Western blots of the purification products were performed by reacting the LKT-SRIF preparation with swine anti-SRIF serum at a 1:500 dilution and the LKT-GnRH and LXT-VP4 preparations with mouse anti-VP4 serum at a 1:50 dilution. The only band visible in the LKT-SRIF western blot was that associated with the LKT-SRIF protein sample. No cross-reactivity with the leukotoxin was observed. Both the LKT-GnRH and LKT-VP4 proteins had similar apparent molecular weights, however, the anti-VP4 serum reacted only with the LKT-VP4 a fusion protein.

All fusion proteins were expressed at high levels as inclusion bodies. The predicted molecular weights based on the DNA sequences of the three proteins (depicted in FIGS. 6, 8 and 10) were 101,366 (LKT-SRIF); 100,521 (LKT-GnRH); and 102,120 (LKT-VP4). The molecular weight of the recombinant leukotoxin molecule was 99,338. Both the SRIF and VP4 fusions were shown to react with monospecific antisera against the corresponding peptide.

EXAMPLE 4

In Vivo Immunologic Activity of LXT-antigen Fusions

To test for enhanced immunogenicity of the LXT-antigen fusions as compared to the antigens alone, LKT-SRIF fusion protein was purified from *E. coli* cultures induced with IPTG, as described in Example 2. Aggregated protein was dissolved by treating with guanidine-HCl at a final concentration of three molar. The leukotoxin concentration of this material was assayed using a standard quantitative leukotoxin specific ELISA. The assay utilized recombinant leukotoxin in 4 N guanidine-HCl (2 mg/ml) as a standard. Rabbit anti-leukotoxin antiserum was used as a detection and quantitation system.

A vaccine was formulated to a volume of 1 ml by mixing equal volumes of LKT-SRIF, diluted in Hanks Buffered Saline, and Emulsigen Plus (MVP Laboratories, Ralston, Nebr.). Four three month old lambs were immunized twice with 100 micrograms of fusion protein (containing an equivalent of approximately 1.4 micrograms of SRIF peptide). Blood samples were taken 10 days after the second injection and were analyzed for leukotoxin and SRIF specific antisera. All of the animals were found to have anti-leukotoxin titers of greater than 1 in 50,000, as determined by a leukotoxin specific ELISA. SRIF titers were assayed by a radioimunoassay as described in Laarveld, B., et al., *Can. J. Anim. Sci.* (1986) 66:77–83. Two animals were found to have titers greater than 1 in 100.

To further test the ability of the LKT-SRIF chimeras to induce an anti-SRIF immunological response in vivo, and to compare this response to that produced by other SRIF conjugates, the following vaccination trial was performed. Three groups of 8 female pigs, approximately 8 weeks of age (35–50 kg) were used which were Specific Pathogen Free. The animals were maintained in a minimal disease facility and were vaccinated on days 0, 21 and 35 of the trial with the following formulations:

Group 1—placebo which was saline formulated in Emulsigen Plus adjuvant containing 15 mg DDA (Kodak) (2 ml);

Group 2—LKT-SRIF (250 μg LKT, prepared as described above) formulated in th same adjuvant (2 ml);

Group 3—SRIF-avidin, biotinylated SRIF (10 μg) and 2.5 μg avidin, formulated in the same adjuvant (2 ml).

Blood samples were taken on days 0, 21 and 35, allowed to clot, centrifuged at 1500 g, and the serum removed. The serum antibody titers against SRIF were measured using the RIA procedure of Laarveld et al., *Can. J. Anim. Sci.* (1986) 6:77–83.

7 of the 8 animals immunized with the LKT-SRIF formulation produced significant titers against SRIF (>1:700) whereas only 2 of 8 animals immunized with the SRIF-Avidin responded with serum titers of >700.

This example demonstrates that leukotoxin chimeric molecules are highly immunogenic. It has been reported by Laarveld, et al., *Can. J. Animal Sci.* (1986) 66:77, that repeated immunization with greater than 100 micrograms of SRIF peptide conjugated to an ovalbumin carrier was necessary to evoke an immune reaction.

EXAMPLE 5

In Vivo Immunologic Activity of LKT-GnRH Fusions

To test for the ability of LKT-GNRH to induce an anti GnRH immunological response in vivo, and to compare this response to other GnRH carrier conjugates, the following vaccination trial was performed. Three groups of 8 male pigs, approximately 8 weeks of age (35–50 kg) were used which were Specific Pathogen Free. The animals were maintained in a minimal disease facility and were vaccinated on days 0 and 21 of the trial with the following formulations:

Group 1—placebo which consisted of saline formulated in Emulsigen Plus adjuvant containing 15 mg of DDA (2 ml);

Group 2—LKT-GnRH (250 μg LXT, prepared as described in the previous examples) formulated in the same adjuvant (2 ml);

Group 3—VP6-GnRH, 0.5 μg VP6 and 5 μg GnRH, formulated in the same adjuvant (2 ml). The VP6 preparation was made as described in U.S. Pat. No. 5,071,651, using the binding peptide described therein.

Blood samples were taken on days 0, 21 and 35, allowed to clot, centrifuged at 1500 g, and the serum removed. The serum antibody titers against GnRH were measured using the RIA procedure of Silversides et al., *J. Reprod. Immunol.* (1985) 7:171–184.

The results of this trial indicated that only those animals immunized with the LKT-GnRH formulation produced significant titers against GnRH (titers >1:70). Neither the placebo nor the VP6-GnRH groups produced anti-GnRH titers. Previously, multiple vaccinations with doses of GnRH of more than 100 μg, conjugated to other carrier proteins, were required to induce anti-hormone titers.

Thus, chimeric proteins including leukotoxin fused to a selected antigen, have been disclosed. Although preferred embodiments of the subject invention have been described in some detail, it is understood that obvious variations can be made without departing from the spirit and the scope of the invention as defined by the appended claims.

SEQUENCE LISTING (1) GENERAL INFORMATION:

(iii) NUMBER OF SEQUENCES: 15

(2) INFORMATION FOR SEQ ID NO: 1:

(i) SEQUENCE CHARACTERISTICS:

-continued

```
          (A) LENGTH: 2794 base pairs
          (B) TYPE: nucleic acid
          (C) STRANDEDNESS: double
          (D) TOPOLOGY: linear (ii) MOLECULE TYPE: DNA (genomic)

(ix) FEATURE:
          (A) NAME/KEY: CDS
          (B) LOCATION: 1..2778

(xi) SEQUENCE DESCRIPTION: SEQ ID NO: 1:

ATG GCT ACT GTT ATA GAT CTA AGC TTC CCA AAA ACT GGG GCA AAA AAA       48
Met Ala Thr Val Ile Asp Leu Ser Phe Pro Lys Thr Gly Ala Lys Lys
  1               5                  10                  15

ATT ATC CTC TAT ATT CCC CAA AAT TAC CAA TAT GAT ACT GAA CAA GGT       96
Ile Ile Leu Tyr Ile Pro Gln Asn Tyr Gln Tyr Asp Thr Glu Gln Gly
                 20                  25                  30

AAT GGT TTA CAG GAT TTA GTC AAA GCG GCC GAA GAG TTG GGG ATT GAG      144
Asn Gly Leu Gln Asp Leu Val Lys Ala Ala Glu Glu Leu Gly Ile Glu
             35                  40                  45

GTA CAA AGA GAA GAA CGC AAT AAT ATT GCA ACA GCT CAA ACC AGT TTA      192
Val Gln Arg Glu Glu Arg Asn Asn Ile Ala Thr Ala Gln Thr Ser Leu
     50                  55                  60

GGC ACG ATT CAA ACC GCT ATT GGC TTA ACT GAG CGT GGC ATT GTG TTA      240
Gly Thr Ile Gln Thr Ala Ile Gly Leu Thr Glu Arg Gly Ile Val Leu
 65                  70                  75                  80

TCC GCT CCA CAA ATT GAT AAA TTG CTA CAG AAA ACT AAA GCA GGC CAA      288
Ser Ala Pro Gln Ile Asp Lys Leu Leu Gln Lys Thr Lys Ala Gly Gln
                 85                  90                  95

GCA TTA GGT TCT GCC GAA AGC ATT GTA CAA AAT GCA AAT AAA GCC AAA      336
Ala Leu Gly Ser Ala Glu Ser Ile Val Gln Asn Ala Asn Lys Ala Lys
            100                 105                 110

ACT GTA TTA TCT GGC ATT CAA TCT ATT TTA GGC TCA GTA TTG GCT GGA      384
Thr Val Leu Ser Gly Ile Gln Ser Ile Leu Gly Ser Val Leu Ala Gly
        115                 120                 125

ATG GAT TTA GAT GAG GCC TTA CAG AAT AAC AGC AAC CAA CAT GCT CTT      432
Met Asp Leu Asp Glu Ala Leu Gln Asn Asn Ser Asn Gln His Ala Leu
    130                 135                 140

GCT AAA GCT GGC TTG GAG CTA ACA AAT TCA TTA ATT GAA AAT ATT GCT      480
Ala Lys Ala Gly Leu Glu Leu Thr Asn Ser Leu Ile Glu Asn Ile Ala
145                 150                 155                 160

AAT TCA GTA AAA ACA CTT GAC GAA TTT GGT GAG CAA ATT AGT CAA TTT      528
Asn Ser Val Lys Thr Leu Asp Glu Phe Gly Glu Gln Ile Ser Gln Phe
                165                 170                 175

GGT TCA AAA CTA CAA AAT ATC AAA GGC TTA GGG ACT TTA GGA GAC AAA      576
Gly Ser Lys Leu Gln Asn Ile Lys Gly Leu Gly Thr Leu Gly Asp Lys
            180                 185                 190

CTC AAA AAT ATC GGT GGA CTT GAT AAA GCT GGC CTT GGT TTA GAT GTT      624
Leu Lys Asn Ile Gly Gly Leu Asp Lys Ala Gly Leu Gly Leu Asp Val
        195                 200                 205

ATC TCA GGG CTA TTA TCG GGC GCA ACA GCT GCA CTT GTA CTT GCA GAT      672
Ile Ser Gly Leu Leu Ser Gly Ala Thr Ala Ala Leu Val Leu Ala Asp
    210                 215                 220

AAA AAT GCT TCA ACA GCT AAA AAA GTG GGT GCG GGT TTT GAA TTG GCA      720
Lys Asn Ala Ser Thr Ala Lys Lys Val Gly Ala Gly Phe Glu Leu Ala
225                 230                 235                 240

AAC CAA GTT GTT GGT AAT ATT ACC AAA GCC GTT TCT TCT TAC ATT TTA      768
Asn Gln Val Val Gly Asn Ile Thr Lys Ala Val Ser Ser Tyr Ile Leu
                245                 250                 255

GCC CAA CGT GTT GCA GCA GGT TTA TCT TCA ACT GGG CCT GTG GCT GCT      816
Ala Gln Arg Val Ala Ala Gly Leu Ser Ser Thr Gly Pro Val Ala Ala
```

-continued

|  |  |  |  |  |  |  |  |  |  |  |  |  |  |  |  |
|---|---|---|---|---|---|---|---|---|---|---|---|---|---|---|---|
| | | | 260 | | | | | 265 | | | | | 270 | | |

```
          260                    265                    270
TTA ATT GCT TCT ACT GTT TCT CTT GCG ATT AGC CCA TTA GCA TTT GCC       864
Leu Ile Ala Ser Thr Val Ser Leu Ala Ile Ser Pro Leu Ala Phe Ala
        275                 280                 285

GGT ATT GCC GAT AAA TTT AAT CAT GCA AAA AGT TTA GAG AGT TAT GCC       912
Gly Ile Ala Asp Lys Phe Asn His Ala Lys Ser Leu Glu Ser Tyr Ala
        290                 295                 300

GAA CGC TTT AAA AAA TTA GGC TAT GAC GGA GAT AAT TTA TTA GCA GAA       960
Glu Arg Phe Lys Lys Leu Gly Tyr Asp Gly Asp Asn Leu Leu Ala Glu
305                 310                 315                 320

TAT CAG CGG GGA ACA GGG ACT ATT GAT GCA TCG GTT ACT GCA ATT AAT      1008
Tyr Gln Arg Gly Thr Gly Thr Ile Asp Ala Ser Val Thr Ala Ile Asn
        325                 330                 335

ACC GCA TTG GCC GCT ATT GCT GGT GGT GTG TCT GCT GCT GCA GCC GGC      1056
Thr Ala Leu Ala Ala Ile Ala Gly Gly Val Ser Ala Ala Ala Ala Gly
        340                 345                 350

TCG GTT ATT GCT TCA CCG ATT GCC TTA TTA GTA TCT GGG ATT ACC GGT      1104
Ser Val Ile Ala Ser Pro Ile Ala Leu Leu Val Ser Gly Ile Thr Gly
        355                 360                 365

GTA ATT TCT ACG ATT CTG CAA TAT TCT AAA CAA GCA ATG TTT GAG CAC      1152
Val Ile Ser Thr Ile Leu Gln Tyr Ser Lys Gln Ala Met Phe Glu His
        370                 375                 380

GTT GCA AAT AAA ATT CAT AAC AAA ATT GTA GAA TGG GAA AAA AAT AAT      1200
Val Ala Asn Lys Ile His Asn Lys Ile Val Glu Trp Glu Lys Asn Asn
385                 390                 395                 400

CAC GGT AAG AAC TAC TTT GAA AAT GGT TAC GAT GCC CGT TAT CTT GCG      1248
His Gly Lys Asn Tyr Phe Glu Asn Gly Tyr Asp Ala Arg Tyr Leu Ala
        405                 410                 415

AAT TTA CAA GAT AAT ATG AAA TTC TTA CTG AAC TTA AAC AAA GAG TTA      1296
Asn Leu Gln Asp Asn Met Lys Phe Leu Leu Asn Leu Asn Lys Glu Leu
        420                 425                 430

CAG GCA GAA CGT GTC ATC GCT ATT ACT CAG CAG CAA TGG GAT AAC AAC      1344
Gln Ala Glu Arg Val Ile Ala Ile Thr Gln Gln Gln Trp Asp Asn Asn
        435                 440                 445

ATT GGT GAT TTA GCT GGT ATT AGC CGT TTA GGT GAA AAA GTC CTT AGT      1392
Ile Gly Asp Leu Ala Gly Ile Ser Arg Leu Gly Glu Lys Val Leu Ser
        450                 455                 460

GGT AAA GCC TAT GTG GAT GCG TTT GAA GAA GGC AAA CAC ATT AAA GCC      1440
Gly Lys Ala Tyr Val Asp Ala Phe Glu Glu Gly Lys His Ile Lys Ala
465                 470                 475                 480

GAT AAA TTA GTA CAG TTG GAT TCG GCA AAC GGT ATT ATT GAT GTG AGT      1488
Asp Lys Leu Val Gln Leu Asp Ser Ala Asn Gly Ile Ile Asp Val Ser
        485                 490                 495

AAT TCG GGT AAA GCG AAA ACT CAG CAT ATC TTA TTC AGA ACG CCA TTA      1536
Asn Ser Gly Lys Ala Lys Thr Gln His Ile Leu Phe Arg Thr Pro Leu
        500                 505                 510

TTG ACG CCG GGA ACA GAG CAT CGT GAA CGC GTA CAA ACA GGT AAA TAT      1584
Leu Thr Pro Gly Thr Glu His Arg Glu Arg Val Gln Thr Gly Lys Tyr
        515                 520                 525

GAA TAT ATT ACC AAG CTC AAT ATT AAC CGT GTA GAT AGC TGG AAA ATT      1632
Glu Tyr Ile Thr Lys Leu Asn Ile Asn Arg Val Asp Ser Trp Lys Ile
        530                 535                 540

ACA GAT GGT GCA GCA AGT TCT ACC TTT GAT TTA ACT AAC GTT GTT CAG      1680
Thr Asp Gly Ala Ala Ser Ser Thr Phe Asp Leu Thr Asn Val Val Gln
545                 550                 555                 560

CGT ATT GGT ATT GAA TTA GAC AAT GCT GGA AAT GTA ACT AAA ACC AAA      1728
Arg Ile Gly Ile Glu Leu Asp Asn Ala Gly Asn Val Thr Lys Thr Lys
        565                 570                 575

GAA ACA AAA ATT ATT GCC AAA CTT GGT GAA GGT GAT GAC AAC GTA TTT      1776
```

```
                Glu Thr Lys Ile Ile Ala Lys Leu Gly Glu Gly Asp Asp Asn Val Phe
                                580                 585                 590

GTT GGT TCT GGT ACG ACG GAA ATT GAT GGC GGT GAA GGT TAC GAC CGA              1824
Val Gly Ser Gly Thr Thr Glu Ile Asp Gly Gly Glu Gly Tyr Asp Arg
            595                 600                 605

GTT CAC TAT AGC CGT GGA AAC TAT GGT GCT TTA ACT ATT GAT GCA ACC              1872
Val His Tyr Ser Arg Gly Asn Tyr Gly Ala Leu Thr Ile Asp Ala Thr
        610                 615                 620

AAA GAG ACC GAG CAA GGT AGT TAT ACC GTA AAT CGT TTC GTA GAA ACC              1920
Lys Glu Thr Glu Gln Gly Ser Tyr Thr Val Asn Arg Phe Val Glu Thr
625                 630                 635                 640

GGT AAA GCA CTA CAC GAA GTG ACT TCA ACC CAT ACC GCA TTA GTG GGC              1968
Gly Lys Ala Leu His Glu Val Thr Ser Thr His Thr Ala Leu Val Gly
                645                 650                 655

AAC CGT GAA GAA AAA ATA GAA TAT CGT CAT AGC AAT AAC CAG CAC CAT              2016
Asn Arg Glu Glu Lys Ile Glu Tyr Arg His Ser Asn Asn Gln His His
            660                 665                 670

GCC GGT TAT TAC ACC AAA GAT ACC TTG AAA GCT GTT GAA GAA ATT ATC              2064
Ala Gly Tyr Tyr Thr Lys Asp Thr Leu Lys Ala Val Glu Glu Ile Ile
        675                 680                 685

GGT ACA TCA CAT AAC GAT ATC TTT AAA GGT AGT AAG TTC AAT GAT GCC              2112
Gly Thr Ser His Asn Asp Ile Phe Lys Gly Ser Lys Phe Asn Asp Ala
690                 695                 700

TTT AAC GGT GGT GAT GGT GTC GAT ACT ATT GAC GGT AAC GAC GGC AAT              2160
Phe Asn Gly Gly Asp Gly Val Asp Thr Ile Asp Gly Asn Asp Gly Asn
705                 710                 715                 720

GAC CGC TTA TTT GGT GGT AAA GGC GAT GAT ATT CTC GAT GGT GGA AAT              2208
Asp Arg Leu Phe Gly Gly Lys Gly Asp Asp Ile Leu Asp Gly Gly Asn
                725                 730                 735

GGT GAT GAT TTT ATC GAT GGC GGT AAA GGC AAC GAC CTA TTA CAC GGT              2256
Gly Asp Asp Phe Ile Asp Gly Gly Lys Gly Asn Asp Leu Leu His Gly
            740                 745                 750

GGC AAG GGC GAT GAT ATT TTC GTT CAC CGT AAA GGC GAT GGT AAT GAT              2304
Gly Lys Gly Asp Asp Ile Phe Val His Arg Lys Gly Asp Gly Asn Asp
        755                 760                 765

ATT ATT ACC GAT TCT GAC GGC AAT GAT AAA TTA TCA TTC TCT GAT TCG              2352
Ile Ile Thr Asp Ser Asp Gly Asn Asp Lys Leu Ser Phe Ser Asp Ser
770                 775                 780

AAC TTA AAA GAT TTA ACA TTT GAA AAA GTT AAA CAT AAT CTT GTC ATC              2400
Asn Leu Lys Asp Leu Thr Phe Glu Lys Val Lys His Asn Leu Val Ile
785                 790                 795                 800

ACG AAT AGC AAA AAA GAG AAA GTG ACC ATT CAA AAC TGG TTC CGA GAG              2448
Thr Asn Ser Lys Lys Glu Lys Val Thr Ile Gln Asn Trp Phe Arg Glu
                805                 810                 815

GCT GAT TTT GCT AAA GAA GTG CCT AAT TAT AAA GCA ACT AAA GAT GAG              2496
Ala Asp Phe Ala Lys Glu Val Pro Asn Tyr Lys Ala Thr Lys Asp Glu
            820                 825                 830

AAA ATC GAA GAA ATC ATC GGT CAA AAT GGC GAG CGG ATC ACC TCA AAG              2544
Lys Ile Glu Glu Ile Ile Gly Gln Asn Gly Glu Arg Ile Thr Ser Lys
        835                 840                 845

CAA GTT GAT GAT CTT ATC GCA AAA GGT AAC GGC AAA ATT ACC CAA GAT              2592
Gln Val Asp Asp Leu Ile Ala Lys Gly Asn Gly Lys Ile Thr Gln Asp
850                 855                 860

GAG CTA TCA AAA GTT GTT GAT AAC TAT GAA TTG CTC AAA CAT AGC AAA              2640
Glu Leu Ser Lys Val Val Asp Asn Tyr Glu Leu Leu Lys His Ser Lys
865                 870                 875                 880

AAT GTG ACA AAC AGC TTA GAT AAG TTA ATC TCA TCT GTA AGT GCA TTT              2688
Asn Val Thr Asn Ser Leu Asp Lys Leu Ile Ser Ser Val Ser Ala Phe
                885                 890                 895
```

```
ACC TCG TCT AAT GAT TCG AGA AAT GTA TTA GTG GCT CCA ACT TCA ATG     2736
Thr Ser Ser Asn Asp Ser Arg Asn Val Leu Val Ala Pro Thr Ser Met
            900                 905                 910

TTG GAT CAA AGT TTA TCT TCT CTT CAA TTT GCT AGG GGA TCC             2778
Leu Asp Gln Ser Leu Ser Ser Leu Gln Phe Ala Arg Gly Ser
            915                 920                 925

TAGCTAGCTA GCCATG                                                   2794
```

(2) INFORMATION FOR SEQ ID NO: 2:

(i) SEQUENCE CHARACTERISTICS:
        (A) LENGTH: 926 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Ala Thr Val Ile Asp Leu Ser Phe Pro Lys Thr Gly Ala Lys Lys
 1               5                  10                  15

Ile Ile Leu Tyr Ile Pro Gln Asn Tyr Gln Tyr Asp Thr Glu Gln Gly
            20                  25                  30

Asn Gly Leu Gln Asp Leu Val Lys Ala Ala Glu Glu Leu Gly Ile Glu
        35                  40                  45

Val Gln Arg Glu Glu Arg Asn Asn Ile Ala Thr Ala Gln Thr Ser Leu
 50                  55                  60

Gly Thr Ile Gln Thr Ala Ile Gly Leu Thr Glu Arg Gly Ile Val Leu
 65                  70                  75                  80

Ser Ala Pro Gln Ile Asp Lys Leu Leu Gln Lys Thr Lys Ala Gly Gln
                85                  90                  95

Ala Leu Gly Ser Ala Glu Ser Ile Val Gln Asn Ala Asn Lys Ala Lys
            100                 105                 110

Thr Val Leu Ser Gly Ile Gln Ser Ile Leu Gly Ser Val Leu Ala Gly
        115                 120                 125

Met Asp Leu Asp Glu Ala Leu Gln Asn Asn Ser Asn Gln His Ala Leu
130                 135                 140

Ala Lys Ala Gly Leu Glu Leu Thr Asn Ser Leu Ile Glu Asn Ile Ala
145                 150                 155                 160

Asn Ser Val Lys Thr Leu Asp Glu Phe Gly Glu Gln Ile Ser Gln Phe
                165                 170                 175

Gly Ser Lys Leu Gln Asn Ile Lys Gly Leu Gly Thr Leu Gly Asp Lys
            180                 185                 190

Leu Lys Asn Ile Gly Gly Leu Asp Lys Ala Gly Leu Gly Leu Asp Val
        195                 200                 205

Ile Ser Gly Leu Leu Ser Gly Ala Thr Ala Ala Leu Val Leu Ala Asp
210                 215                 220

Lys Asn Ala Ser Thr Ala Lys Lys Val Gly Ala Gly Phe Glu Leu Ala
225                 230                 235                 240

Asn Gln Val Val Gly Asn Ile Thr Lys Ala Val Ser Ser Tyr Ile Leu
                245                 250                 255

Ala Gln Arg Val Ala Ala Gly Leu Ser Ser Thr Gly Pro Val Ala Ala
            260                 265                 270

Leu Ile Ala Ser Thr Val Ser Leu Ala Ile Ser Pro Leu Ala Phe Ala
        275                 280                 285

Gly Ile Ala Asp Lys Phe Asn His Ala Lys Ser Leu Glu Ser Tyr Ala
290                 295                 300
```

-continued

```
Glu Arg Phe Lys Lys Leu Gly Tyr Asp Gly Asp Asn Leu Leu Ala Glu
305                 310                 315                 320

Tyr Gln Arg Gly Thr Gly Thr Ile Asp Ala Ser Val Thr Ala Ile Asn
            325                 330                 335

Thr Ala Leu Ala Ala Ile Ala Gly Gly Val Ser Ala Ala Ala Ala Gly
            340                 345                 350

Ser Val Ile Ala Ser Pro Ile Ala Leu Leu Val Ser Gly Ile Thr Gly
            355                 360                 365

Val Ile Ser Thr Ile Leu Gln Tyr Ser Lys Gln Ala Met Phe Glu His
        370                 375                 380

Val Ala Asn Lys Ile His Asn Lys Ile Val Glu Trp Glu Lys Asn Asn
385                 390                 395                 400

His Gly Lys Asn Tyr Phe Glu Asn Gly Tyr Asp Ala Arg Tyr Leu Ala
                405                 410                 415

Asn Leu Gln Asp Asn Met Lys Phe Leu Leu Asn Leu Asn Lys Glu Leu
            420                 425                 430

Gln Ala Glu Arg Val Ile Ala Ile Thr Gln Gln Gln Trp Asp Asn Asn
        435                 440                 445

Ile Gly Asp Leu Ala Gly Ile Ser Arg Leu Gly Glu Lys Val Leu Ser
    450                 455                 460

Gly Lys Ala Tyr Val Asp Ala Phe Glu Glu Gly Lys His Ile Lys Ala
465                 470                 475                 480

Asp Lys Leu Val Gln Leu Asp Ser Ala Asn Gly Ile Ile Asp Val Ser
                485                 490                 495

Asn Ser Gly Lys Ala Lys Thr Gln His Ile Leu Phe Arg Thr Pro Leu
            500                 505                 510

Leu Thr Pro Gly Thr Glu His Arg Glu Arg Val Gln Thr Gly Lys Tyr
        515                 520                 525

Glu Tyr Ile Thr Lys Leu Asn Ile Asn Arg Val Asp Ser Trp Lys Ile
    530                 535                 540

Thr Asp Gly Ala Ala Ser Ser Thr Phe Asp Leu Thr Asn Val Val Gln
545                 550                 555                 560

Arg Ile Gly Ile Glu Leu Asp Asn Ala Gly Asn Val Thr Lys Thr Lys
                565                 570                 575

Glu Thr Lys Ile Ile Ala Lys Leu Gly Glu Gly Asp Asp Asn Val Phe
            580                 585                 590

Val Gly Ser Gly Thr Thr Glu Ile Asp Gly Gly Glu Gly Tyr Asp Arg
        595                 600                 605

Val His Tyr Ser Arg Gly Asn Tyr Gly Ala Leu Thr Ile Asp Ala Thr
    610                 615                 620

Lys Glu Thr Glu Gln Gly Ser Tyr Thr Val Asn Arg Phe Val Glu Thr
625                 630                 635                 640

Gly Lys Ala Leu His Glu Val Thr Ser Thr His Thr Ala Leu Val Gly
                645                 650                 655

Asn Arg Glu Glu Lys Ile Glu Tyr Arg His Ser Asn Asn Gln His His
            660                 665                 670

Ala Gly Tyr Tyr Thr Lys Asp Thr Leu Lys Ala Val Glu Glu Ile Ile
        675                 680                 685

Gly Thr Ser His Asn Asp Ile Phe Lys Gly Ser Lys Phe Asn Asp Ala
    690                 695                 700

Phe Asn Gly Gly Asp Gly Val Asp Thr Ile Asp Gly Asn Asp Gly Asn
705                 710                 715                 720

Asp Arg Leu Phe Gly Gly Lys Gly Asp Asp Ile Leu Asp Gly Gly Asn
```

```
                    725                 730                 735
Gly Asp Asp Phe Ile Asp Gly Gly Lys Gly Asn Asp Leu Leu His Gly
                740                 745                 750
Gly Lys Gly Asp Asp Ile Phe Val His Arg Lys Gly Asp Gly Asn Asp
                755                 760                 765
Ile Ile Thr Asp Ser Asp Gly Asn Asp Lys Leu Ser Phe Ser Asp Ser
                770                 775                 780
Asn Leu Lys Asp Leu Thr Phe Glu Lys Val Lys His Asn Leu Val Ile
785                 790                 795                 800
Thr Asn Ser Lys Lys Glu Lys Val Thr Ile Gln Asn Trp Phe Arg Glu
                805                 810                 815
Ala Asp Phe Ala Lys Glu Val Pro Asn Tyr Lys Ala Thr Lys Asp Glu
                820                 825                 830
Lys Ile Glu Glu Ile Ile Gly Gln Asn Gly Glu Arg Ile Thr Ser Lys
                835                 840                 845
Gln Val Asp Asp Leu Ile Ala Lys Gly Asn Gly Lys Ile Thr Gln Asp
                850                 855                 860
Glu Leu Ser Lys Val Val Asp Asn Tyr Glu Leu Leu Lys His Ser Lys
865                 870                 875                 880
Asn Val Thr Asn Ser Leu Asp Lys Leu Ile Ser Ser Val Ser Ala Phe
                885                 890                 895
Thr Ser Ser Asn Asp Ser Arg Asn Val Leu Val Ala Pro Thr Ser Met
                900                 905                 910
Leu Asp Gln Ser Leu Ser Ser Leu Gln Phe Ala Arg Gly Ser
                915                 920                 925
```

(2) INFORMATION FOR SEQ ID NO: 3:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

```
GATCCAGCTC TTCTGCCGGC TGCAAAAACT TCTTCTGGAA AACCTTCACC AGCTGCTAGG    60
```

(2) INFORMATION FOR SEQ ID NO: 4:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

```
GATCCCTAGC AGCTGGTGAA GGTTTTCCAG AAGAAGTTTT TGCAGCCGGC AGAAGAGCTG    60
```

(2) INFORMATION FOR SEQ ID NO: 5:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

GATCTCAGCA TTGGAGCTAC GGCCTGCGCC CTGGCTAAG                                   39

(2) INFORMATION FOR SEQ ID NO: 6:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 6:

GATCCTTAGC CAGGGCGCAG GCCGTAGCTC CAATGCTGA                                   39

(2) INFORMATION FOR SEQ ID NO: 7:

(i) SEQUENCE CHARACTERISTICS:
            (A) LENGTH: 83 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 7:

GATCTTGCAA CATTGTGCCT GTGAGCATTG TGAGCCGCAA CATTGTGTAC ACCCGCGCGC            60

AACCTAACCA AGACATTGTG TAG                                                   83

(2) INFORMATION FOR SEQ ID NO: 8:

(i) SEQUENCE CHARACTERISTICS:
            (A) LENGTH: 83 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 8:

GATCCTACAC AATGTCTTGG TTAAGTTGCG CGCGGGTGTA CACAATGTTG CGGCTCACAA            60

TCGTCACAGG CACAATGTTG CAA                                                   83

(2) INFORMATION FOR SEQ ID NO: 9:

(i) SEQUENCE CHARACTERISTICS:
            (A) LENGTH: 2838 base pairs
            (B) TYPE: nucleic acid
            (C) STRANDEDNESS: double
            (D) TOPOLOGY: linear (ii) MOLECULE TYPE: DNA (genomic)

(ix) FEATURE:
            (A) NAME/KEY: CDS
            (B) LOCATION: 1..2829

(xi) SEQUENCE DESCRIPTION: SEQ ID NO: 9:

ATG GCT ACT GTT ATA GAT CTA AGC TTC CCA AAA ACT GGG GCA AAA AAA             48
Met Ala Thr Val Ile Asp Leu Ser Phe Pro Lys Thr Gly Ala Lys Lys
 1               5                  10                  15

ATT ATC CTC TAT ATT CCC CAA AAT TAC CAA TAT GAT ACT GAA CAA GGT             96
Ile Ile Leu Tyr Ile Pro Gln Asn Tyr Gln Tyr Asp Thr Glu Gln Gly
                20                  25                  30

AAT GGT TTA CAG GAT TTA GTC AAA GCG GCC GAA GAG TTG GGG ATT GAG            144

```
                                                          -continued

Asn Gly Leu Gln Asp Leu Val Lys Ala Ala Glu Glu Leu Gly Ile Glu
         35                  40                  45

GTA CAA AGA GAA GAA CGC AAT AAT ATT GCA ACA GCT CAA ACC AGT TTA       192
Val Gln Arg Glu Glu Arg Asn Asn Ile Ala Thr Ala Gln Thr Ser Leu
 50                  55                  60

GGC ACG ATT CAA ACC GCT ATT GGC TTA ACT GAG CGT GGC ATT GTG TTA       240
Gly Thr Ile Gln Thr Ala Ile Gly Leu Thr Glu Arg Gly Ile Val Leu
 65                  70                  75                  80

TCC GCT CCA CAA ATT GAT AAA TTG CTA CAG AAA ACT AAA GCA GGC CAA       288
Ser Ala Pro Gln Ile Asp Lys Leu Leu Gln Lys Thr Lys Ala Gly Gln
                 85                  90                  95

GCA TTA GGT TCT GCC GAA AGC ATT GTA CAA AAT GCA AAT AAA GCC AAA       336
Ala Leu Gly Ser Ala Glu Ser Ile Val Gln Asn Ala Asn Lys Ala Lys
                100                 105                 110

ACT GTA TTA TCT GGC ATT CAA TCT ATT TTA GGC TCA GTA TTG GCT GGA       384
Thr Val Leu Ser Gly Ile Gln Ser Ile Leu Gly Ser Val Leu Ala Gly
            115                 120                 125

ATG GAT TTA GAT GAG GCC TTA CAG AAT AAC AGC AAC CAA CAT GCT CTT       432
Met Asp Leu Asp Glu Ala Leu Gln Asn Asn Ser Asn Gln His Ala Leu
130                 135                 140

GCT AAA GCT GGC TTG GAG CTA ACA AAT TCA TTA ATT GAA AAT ATT GCT       480
Ala Lys Ala Gly Leu Glu Leu Thr Asn Ser Leu Ile Glu Asn Ile Ala
145                 150                 155                 160

AAT TCA GTA AAA ACA CTT GAC GAA TTT GGT GAG CAA ATT AGT CAA TTT       528
Asn Ser Val Lys Thr Leu Asp Glu Phe Gly Glu Gln Ile Ser Gln Phe
                165                 170                 175

GGT TCA AAA CTA CAA AAT ATC AAA GGC TTA GGG ACT TTA GGA GAC AAA       576
Gly Ser Lys Leu Gln Asn Ile Lys Gly Leu Gly Thr Leu Gly Asp Lys
            180                 185                 190

CTC AAA AAT ATC GGT GGA CTT GAT AAA GCT GGC CTT GGT TTA GAT GTT       624
Leu Lys Asn Ile Gly Gly Leu Asp Lys Ala Gly Leu Gly Leu Asp Val
        195                 200                 205

ATC TCA GGG CTA TTA TCG GGC GCA ACA GCT GCA CTT GTA CTT GCA GAT       672
Ile Ser Gly Leu Leu Ser Gly Ala Thr Ala Ala Leu Val Leu Ala Asp
210                 215                 220

AAA AAT GCT TCA ACA GCT AAA AAA GTG GGT GCG GGT TTT GAA TTG GCA       720
Lys Asn Ala Ser Thr Ala Lys Lys Val Gly Ala Gly Phe Glu Leu Ala
225                 230                 235                 240

AAC CAA GTT GTT GGT AAT ATT ACC AAA GCC GTT TCT TCT TAC ATT TTA       768
Asn Gln Val Val Gly Asn Ile Thr Lys Ala Val Ser Ser Tyr Ile Leu
                245                 250                 255

GCC CAA CGT GTT GCA GCA GGT TTA TCT TCA ACT GGG CCT GTG GCT GCT       816
Ala Gln Arg Val Ala Ala Gly Leu Ser Ser Thr Gly Pro Val Ala Ala
            260                 265                 270

TTA ATT GCT TCT ACT GTT TCT CTT GCG ATT AGC CCA TTA GCA TTT GCC       864
Leu Ile Ala Ser Thr Val Ser Leu Ala Ile Ser Pro Leu Ala Phe Ala
        275                 280                 285

GGT ATT GCC GAT AAA TTT AAT CAT GCA AAA AGT TTA GAG AGT TAT GCC       912
Gly Ile Ala Asp Lys Phe Asn His Ala Lys Ser Leu Glu Ser Tyr Ala
        290                 295                 300

GAA CGC TTT AAA AAA TTA GGC TAT GAC GGA GAT AAT TTA TTA GCA GAA       960
Glu Arg Phe Lys Lys Leu Gly Tyr Asp Gly Asp Asn Leu Leu Ala Glu
305                 310                 315                 320

TAT CAG CGG GGA ACA GGG ACT ATT GAT GCA TCG GTT ACT GCA ATT AAT      1008
Tyr Gln Arg Gly Thr Gly Thr Ile Asp Ala Ser Val Thr Ala Ile Asn
                325                 330                 335

ACC GCA TTG GCC GCT ATT GCT GGT GGT GTG TCT GCT GCT GCA GCC GGC      1056
Thr Ala Leu Ala Ala Ile Ala Gly Gly Val Ser Ala Ala Ala Ala Gly
            340                 345                 350
```

-continued

```
TCG GTT ATT GCT TCA CCG ATT GCC TTA TTA GTA TCT GGG ATT ACC GGT      1104
Ser Val Ile Ala Ser Pro Ile Ala Leu Leu Val Ser Gly Ile Thr Gly
        355                 360                 365

GTA ATT TCT ACG ATT CTG CAA TAT TCT AAA CAA GCA ATG TTT GAG CAC      1152
Val Ile Ser Thr Ile Leu Gln Tyr Ser Lys Gln Ala Met Phe Glu His
        370                 375                 380

GTT GCA AAT AAA ATT CAT AAC AAA ATT GTA GAA TGG GAA AAA AAT AAT      1200
Val Ala Asn Lys Ile His Asn Lys Ile Val Glu Trp Glu Lys Asn Asn
385                 390                 395                 400

CAC GGT AAG AAC TAC TTT GAA AAT GGT TAC GAT GCC CGT TAT CTT GCG      1248
His Gly Lys Asn Tyr Phe Glu Asn Gly Tyr Asp Ala Arg Tyr Leu Ala
                405                 410                 415

AAT TTA CAA GAT AAT ATG AAA TTC TTA CTG AAC TTA AAC AAA GAG TTA      1296
Asn Leu Gln Asp Asn Met Lys Phe Leu Leu Asn Leu Asn Lys Glu Leu
            420                 425                 430

CAG GCA GAA CGT GTC ATC GCT ATT ACT CAG CAG CAA TGG GAT AAC AAC      1344
Gln Ala Glu Arg Val Ile Ala Ile Thr Gln Gln Gln Trp Asp Asn Asn
                435                 440                 445

ATT GGT GAT TTA GCT GGT ATT AGC CGT TTA GGT GAA AAA GTC CTT AGT      1392
Ile Gly Asp Leu Ala Gly Ile Ser Arg Leu Gly Glu Lys Val Leu Ser
        450                 455                 460

GGT AAA GCC TAT GTG GAT GCG TTT GAA GAA GGC AAA CAC ATT AAA GCC      1440
Gly Lys Ala Tyr Val Asp Ala Phe Glu Glu Gly Lys His Ile Lys Ala
465                 470                 475                 480

GAT AAA TTA GTA CAG TTG GAT TCG GCA AAC GGT ATT ATT GAT GTG AGT      1488
Asp Lys Leu Val Gln Leu Asp Ser Ala Asn Gly Ile Ile Asp Val Ser
                485                 490                 495

AAT TCG GGT AAA GCG AAA ACT CAG CAT ATC TTA TTC AGA ACG CCA TTA      1536
Asn Ser Gly Lys Ala Lys Thr Gln His Ile Leu Phe Arg Thr Pro Leu
            500                 505                 510

TTG ACG CCG GGA ACA GAG CAT CGT GAA CGC GTA CAA ACA GGT AAA TAT      1584
Leu Thr Pro Gly Thr Glu His Arg Glu Arg Val Gln Thr Gly Lys Tyr
                515                 520                 525

GAA TAT ATT ACC AAG CTC AAT ATT AAC CGT GTA GAT AGC TGG AAA ATT      1632
Glu Tyr Ile Thr Lys Leu Asn Ile Asn Arg Val Asp Ser Trp Lys Ile
        530                 535                 540

ACA GAT GGT GCA GCA AGT TCT ACC TTT GAT TTA ACT AAC GTT GTT CAG      1680
Thr Asp Gly Ala Ala Ser Ser Thr Phe Asp Leu Thr Asn Val Val Gln
545                 550                 555                 560

CGT ATT GGT ATT GAA TTA GAC AAT GCT GGA AAT GTA ACT AAA ACC AAA      1728
Arg Ile Gly Ile Glu Leu Asp Asn Ala Gly Asn Val Thr Lys Thr Lys
                565                 570                 575

GAA ACA AAA ATT ATT GCC AAA CTT GGT GAA GGT GAT GAC AAC GTA TTT      1776
Glu Thr Lys Ile Ile Ala Lys Leu Gly Glu Gly Asp Asp Asn Val Phe
            580                 585                 590

GTT GGT TCT GGT ACG ACG GAA ATT GAT GGC GGT GAA GGT TAC GAC CGA      1824
Val Gly Ser Gly Thr Thr Glu Ile Asp Gly Gly Glu Gly Tyr Asp Arg
                595                 600                 605

GTT CAC TAT AGC CGT GGA AAC TAT GGT GCT TTA ACT ATT GAT GCA ACC      1872
Val His Tyr Ser Arg Gly Asn Tyr Gly Ala Leu Thr Ile Asp Ala Thr
        610                 615                 620

AAA GAG ACC GAG CAA GGT AGT TAT ACC GTA AAT CGT TTC GTA GAA ACC      1920
Lys Glu Thr Glu Gln Gly Ser Tyr Thr Val Asn Arg Phe Val Glu Thr
625                 630                 635                 640

GGT AAA GCA CTA CAC GAA GTG ACT TCA ACC CAT ACC GCA TTA GTG GGC      1968
Gly Lys Ala Leu His Glu Val Thr Ser Thr His Thr Ala Leu Val Gly
                645                 650                 655

AAC CGT GAA GAA AAA ATA GAA TAT CGT CAT AGC AAT AAC CAG CAC CAT      2016
Asn Arg Glu Glu Lys Ile Glu Tyr Arg His Ser Asn Asn Gln His His
            660                 665                 670
```

```
GCC GGT TAT TAC ACC AAA GAT ACC TTG AAA GCT GTT GAA GAA ATT ATC       2064
Ala Gly Tyr Tyr Thr Lys Asp Thr Leu Lys Ala Val Glu Glu Ile Ile
            675                 680                 685

GGT ACA TCA CAT AAC GAT ATC TTT AAA GGT AGT AAG TTC AAT GAT GCC       2112
Gly Thr Ser His Asn Asp Ile Phe Lys Gly Ser Lys Phe Asn Asp Ala
        690                 695                 700

TTT AAC GGT GGT GAT GGT GTC GAT ACT ATT GAC GGT AAC GAC GGC AAT       2160
Phe Asn Gly Gly Asp Gly Val Asp Thr Ile Asp Gly Asn Asp Gly Asn
705                 710                 715                 720

GAC CGC TTA TTT GGT GGT AAA GGC GAT GAT ATT CTC GAT GGT GGA AAT       2208
Asp Arg Leu Phe Gly Gly Lys Gly Asp Asp Ile Leu Asp Gly Gly Asn
                725                 730                 735

GGT GAT GAT TTT ATC GAT GGC GGT AAA GGC AAC GAC CTA TTA CAC GGT       2256
Gly Asp Asp Phe Ile Asp Gly Gly Lys Gly Asn Asp Leu Leu His Gly
            740                 745                 750

GGC AAG GGC GAT GAT ATT TTC GTT CAC CGT AAA GGC GAT GGT AAT GAT       2304
Gly Lys Gly Asp Asp Ile Phe Val His Arg Lys Gly Asp Gly Asn Asp
        755                 760                 765

ATT ATT ACC GAT TCT GAC GGC AAT GAT AAA TTA TCA TTC TCT GAT TCG       2352
Ile Ile Thr Asp Ser Asp Gly Asn Asp Lys Leu Ser Phe Ser Asp Ser
770                 775                 780

AAC TTA AAA GAT TTA ACA TTT GAA AAA GTT AAA CAT AAT CTT GTC ATC       2400
Asn Leu Lys Asp Leu Thr Phe Glu Lys Val Lys His Asn Leu Val Ile
                785                 790                 795                 800

ACG AAT AGC AAA AAA GAG AAA GTG ACC ATT CAA AAC TGG TTC CGA GAG       2448
Thr Asn Ser Lys Lys Glu Lys Val Thr Ile Gln Asn Trp Phe Arg Glu
                805                 810                 815

GCT GAT TTT GCT AAA GAA GTG CCT AAT TAT AAA GCA ACT AAA GAT GAG       2496
Ala Asp Phe Ala Lys Glu Val Pro Asn Tyr Lys Ala Thr Lys Asp Glu
            820                 825                 830

AAA ATC GAA GAA ATC ATC GGT CAA AAT GGC GAG CGG ATC ACC TCA AAG       2544
Lys Ile Glu Glu Ile Ile Gly Gln Asn Gly Glu Arg Ile Thr Ser Lys
        835                 840                 845

CAA GTT GAT GAT CTT ATC GCA AAA GGT AAC GGC AAA ATT ACC CAA GAT       2592
Gln Val Asp Asp Leu Ile Ala Lys Gly Asn Gly Lys Ile Thr Gln Asp
850                 855                 860

GAG CTA TCA AAA GTT GTT GAT AAC TAT GAA TTG CTC AAA CAT AGC AAA       2640
Glu Leu Ser Lys Val Val Asp Asn Tyr Glu Leu Leu Lys His Ser Lys
            865                 870                 875                 880

AAT GTG ACA AAC AGC TTA GAT AAG TTA ATC TCA TCT GTA AGT GCA TTT       2688
Asn Val Thr Asn Ser Leu Asp Lys Leu Ile Ser Ser Val Ser Ala Phe
                885                 890                 895

ACC TCG TCT AAT GAT TCG AGA AAT GTA TTA GTG GCT CCA ACT TCA ATG       2736
Thr Ser Ser Asn Asp Ser Arg Asn Val Leu Val Ala Pro Thr Ser Met
            900                 905                 910

TTG GAT CAA AGT TTA TCT TCT CTT CAA TTT GCT AGG GGA TCC AGC TCT       2784
Leu Asp Gln Ser Leu Ser Ser Leu Gln Phe Ala Arg Gly Ser Ser Ser
        915                 920                 925

TCT GCC GGC TGC AAA AAC TTC TTC TGG AAA ACC TTC ACC AGC TGC            2829
Ser Ala Gly Cys Lys Asn Phe Phe Trp Lys Thr Phe Thr Ser Cys
930                 935                 940

TAGGGATCC                                                              2838
```

(2) INFORMATION FOR SEQ ID NO: 10:

(i) SEQUENCE CHARACTERISTICS:
        (A) LENGTH: 943 amino acids
        (B) TYPE: amino acid
        (D) TOPOLOGY: linear (ii) MOLECULE TYPE: protein (xi) SEQUENCE DESCRIPTION: SEQ ID NO: 10:

```
Met Ala Thr Val Ile Asp Leu Ser Phe Pro Lys Thr Gly Ala Lys Lys
 1               5                  10                  15

Ile Ile Leu Tyr Ile Pro Gln Asn Tyr Gln Tyr Asp Thr Glu Gln Gly
                20                  25                  30

Asn Gly Leu Gln Asp Leu Val Lys Ala Glu Glu Leu Gly Ile Glu
        35                  40                  45

Val Gln Arg Glu Glu Arg Asn Asn Ile Ala Thr Ala Gln Thr Ser Leu
    50                  55                  60

Gly Thr Ile Gln Thr Ala Ile Gly Leu Thr Glu Arg Gly Ile Val Leu
 65                  70                  75                  80

Ser Ala Pro Gln Ile Asp Lys Leu Leu Gln Lys Thr Lys Ala Gly Gln
                85                  90                  95

Ala Leu Gly Ser Ala Glu Ser Ile Val Gln Asn Ala Asn Lys Ala Lys
                100                 105                 110

Thr Val Leu Ser Gly Ile Gln Ser Ile Leu Gly Ser Val Leu Ala Gly
            115                 120                 125

Met Asp Leu Asp Glu Ala Leu Gln Asn Asn Ser Asn Gln His Ala Leu
            130                 135                 140

Ala Lys Ala Gly Leu Glu Leu Thr Asn Ser Leu Ile Glu Asn Ile Ala
145                 150                 155                 160

Asn Ser Val Lys Thr Leu Asp Glu Phe Gly Glu Gln Ile Ser Gln Phe
                165                 170                 175

Gly Ser Lys Leu Gln Asn Ile Lys Gly Leu Gly Thr Leu Gly Asp Lys
            180                 185                 190

Leu Lys Asn Ile Gly Gly Leu Asp Lys Ala Gly Leu Gly Leu Asp Val
            195                 200                 205

Ile Ser Gly Leu Leu Ser Gly Ala Thr Ala Ala Leu Val Leu Ala Asp
210                 215                 220

Lys Asn Ala Ser Thr Ala Lys Lys Val Gly Ala Gly Phe Glu Leu Ala
225                 230                 235                 240

Asn Gln Val Val Gly Asn Ile Thr Lys Ala Val Ser Ser Tyr Ile Leu
                245                 250                 255

Ala Gln Arg Val Ala Ala Gly Leu Ser Ser Thr Gly Pro Val Ala Ala
            260                 265                 270

Leu Ile Ala Ser Thr Val Ser Leu Ala Ile Ser Pro Leu Ala Phe Ala
            275                 280                 285

Gly Ile Ala Asp Lys Phe Asn His Ala Lys Ser Leu Glu Ser Tyr Ala
            290                 295                 300

Glu Arg Phe Lys Lys Leu Gly Tyr Asp Gly Asp Asn Leu Leu Ala Glu
305                 310                 315                 320

Tyr Gln Arg Gly Thr Gly Thr Ile Asp Ala Ser Val Thr Ala Ile Asn
                325                 330                 335

Thr Ala Leu Ala Ala Ile Ala Gly Gly Val Ser Ala Ala Ala Gly
            340                 345                 350

Ser Val Ile Ala Ser Pro Ile Ala Leu Leu Val Ser Gly Ile Thr Gly
            355                 360                 365

Val Ile Ser Thr Ile Leu Gln Tyr Ser Lys Gln Ala Met Phe Glu His
            370                 375                 380

Val Ala Asn Lys Ile His Asn Lys Ile Val Glu Trp Glu Lys Asn Asn
385                 390                 395                 400
```

-continued

```
His Gly Lys Asn Tyr Phe Glu Asn Gly Tyr Asp Ala Arg Tyr Leu Ala
                405                 410                 415
Asn Leu Gln Asp Asn Met Lys Phe Leu Leu Asn Leu Asn Lys Glu Leu
            420                 425                 430
Gln Ala Glu Arg Val Ile Ala Ile Thr Gln Gln Trp Asp Asn Asn
        435                 440                 445
Ile Gly Asp Leu Ala Gly Ile Ser Arg Leu Gly Glu Lys Val Leu Ser
    450                 455                 460
Gly Lys Ala Tyr Val Asp Ala Phe Glu Glu Gly Lys His Ile Lys Ala
465                 470                 475                 480
Asp Lys Leu Val Gln Leu Asp Ser Ala Asn Gly Ile Ile Asp Val Ser
                485                 490                 495
Asn Ser Gly Lys Ala Lys Thr Gln His Ile Leu Phe Arg Thr Pro Leu
            500                 505                 510
Leu Thr Pro Gly Thr Glu His Arg Glu Arg Val Gln Thr Gly Lys Tyr
        515                 520                 525
Glu Tyr Ile Thr Lys Leu Asn Ile Asn Arg Val Asp Ser Trp Lys Ile
    530                 535                 540
Thr Asp Gly Ala Ala Ser Ser Thr Phe Asp Leu Thr Asn Val Val Gln
545                 550                 555                 560
Arg Ile Gly Ile Glu Leu Asp Asn Ala Gly Asn Val Thr Lys Thr Lys
                565                 570                 575
Glu Thr Lys Ile Ile Ala Lys Leu Gly Glu Gly Asp Asp Asn Val Phe
            580                 585                 590
Val Gly Ser Gly Thr Thr Glu Ile Asp Gly Gly Glu Gly Tyr Asp Arg
        595                 600                 605
Val His Tyr Ser Arg Gly Asn Tyr Gly Ala Leu Thr Ile Asp Ala Thr
    610                 615                 620
Lys Glu Thr Glu Gln Gly Ser Tyr Thr Val Asn Arg Phe Val Glu Thr
625                 630                 635                 640
Gly Lys Ala Leu His Glu Val Thr Ser Thr His Thr Ala Leu Val Gly
                645                 650                 655
Asn Arg Glu Glu Lys Ile Glu Tyr Arg His Ser Asn Asn Gln His His
            660                 665                 670
Ala Gly Tyr Tyr Thr Lys Asp Thr Leu Lys Ala Val Glu Glu Ile Ile
        675                 680                 685
Gly Thr Ser His Asn Asp Ile Phe Lys Gly Ser Lys Phe Asn Asp Ala
    690                 695                 700
Phe Asn Gly Gly Asp Gly Val Asp Thr Ile Asp Gly Asn Asp Gly Asn
705                 710                 715                 720
Asp Arg Leu Phe Gly Gly Lys Gly Asp Ile Leu Asp Gly Gly Asn
                725                 730                 735
Gly Asp Asp Phe Ile Asp Gly Gly Lys Gly Asn Asp Leu Leu His Gly
            740                 745                 750
Gly Lys Gly Asp Asp Ile Phe Val His Arg Lys Gly Asp Gly Asn Asp
        755                 760                 765
Ile Ile Thr Asp Ser Asp Gly Asn Asp Lys Leu Ser Phe Ser Asp Ser
    770                 775                 780
Asn Leu Lys Asp Leu Thr Phe Glu Lys Val Lys His Asn Leu Val Ile
785                 790                 795                 800
Thr Asn Ser Lys Lys Glu Lys Val Thr Ile Gln Asn Trp Phe Arg Glu
                805                 810                 815
Ala Asp Phe Ala Lys Glu Val Pro Asn Tyr Lys Ala Thr Lys Asp Glu
```

-continued

```
                820                 825                 830
Lys Ile Glu Glu Ile Ile Gly Gln Asn Gly Glu Arg Ile Thr Ser Lys
            835                 840                 845

Gln Val Asp Asp Leu Ile Ala Lys Gly Asn Gly Lys Ile Thr Gln Asp
        850                 855                 860

Glu Leu Ser Lys Val Val Asp Asn Tyr Glu Leu Leu Lys His Ser Lys
865                 870                 875                 880

Asn Val Thr Asn Ser Leu Asp Lys Leu Ile Ser Ser Val Ser Ala Phe
                885                 890                 895

Thr Ser Ser Asn Asp Ser Arg Asn Val Leu Val Ala Pro Thr Ser Met
            900                 905                 910

Leu Asp Gln Ser Leu Ser Ser Leu Gln Phe Ala Arg Gly Ser Ser Ser
        915                 920                 925

Ser Ala Gly Cys Lys Asn Phe Phe Trp Lys Thr Phe Thr Ser Cys
    930                 935                 940
```

(2) INFORMATION FOR SEQ ID NO: 11:

(i) SEQUENCE CHARACTERISTICS:
        (A) LENGTH: 2817 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..2808

(xi) SEQUENCE DESCRIPTION: SEQ ID NO: 11:

```
ATG GCT ACT GTT ATA GAT CTA AGC TTC CCA AAA ACT GGG GCA AAA AAA         48
Met Ala Thr Val Ile Asp Leu Ser Phe Pro Lys Thr Gly Ala Lys Lys
 1               5                  10                  15

ATT ATC CTC TAT ATT CCC CAA AAT TAC CAA TAT GAT ACT GAA CAA GGT         96
Ile Ile Leu Tyr Ile Pro Gln Asn Tyr Gln Tyr Asp Thr Glu Gln Gly
                20                  25                  30

AAT GGT TTA CAG GAT TTA GTC AAA GCG GCC GAA GAG TTG GGG ATT GAG        144
Asn Gly Leu Gln Asp Leu Val Lys Ala Ala Glu Glu Leu Gly Ile Glu
            35                  40                  45

GTA CAA AGA GAA GAA CGC AAT AAT ATT GCA ACA GCT CAA ACC AGT TTA        192
Val Gln Arg Glu Glu Arg Asn Asn Ile Ala Thr Ala Gln Thr Ser Leu
        50                  55                  60

GGC ACG ATT CAA ACC GCT ATT GGC TTA ACT GAG CGT GGC ATT GTG TTA        240
Gly Thr Ile Gln Thr Ala Ile Gly Leu Thr Glu Arg Gly Ile Val Leu
65                  70                  75                  80

TCC GCT CCA CAA ATT GAT AAA TTG CTA CAG AAA ACT AAA GCA GGC CAA        288
Ser Ala Pro Gln Ile Asp Lys Leu Leu Gln Lys Thr Lys Ala Gly Gln
                85                  90                  95

GCA TTA GGT TCT GCC GAA AGC ATT GTA CAA AAT GCA AAT AAA GCC AAA        336
Ala Leu Gly Ser Ala Glu Ser Ile Val Gln Asn Ala Asn Lys Ala Lys
            100                 105                 110

ACT GTA TTA TCT GGC ATT CAA TCT ATT TTA GGC TCA GTA TTG GCT GGA        384
Thr Val Leu Ser Gly Ile Gln Ser Ile Leu Gly Ser Val Leu Ala Gly
        115                 120                 125

ATG GAT TTA GAT GAG GCC TTA CAG AAT AAC AGC AAC CAA CAT GCT CTT        432
Met Asp Leu Asp Glu Ala Leu Gln Asn Asn Ser Asn Gln His Ala Leu
    130                 135                 140

GCT AAA GCT GGC TTG GAG CTA ACA AAT TCA TTA ATT GAA AAT ATT GCT        480
Ala Lys Ala Gly Leu Glu Leu Thr Asn Ser Leu Ile Glu Asn Ile Ala
145                 150                 155                 160
```

-continued

| | |
|---|---|
| AAT TCA GTA AAA ACA CTT GAC GAA TTT GGT GAG CAA ATT AGT CAA TTT<br>Asn Ser Val Lys Thr Leu Asp Glu Phe Gly Glu Gln Ile Ser Gln Phe<br>                  165                  170                  175 | 528 |
| GGT TCA AAA CTA CAA AAT ATC AAA GGC TTA GGG ACT TTA GGA GAC AAA<br>Gly Ser Lys Leu Gln Asn Ile Lys Gly Leu Gly Thr Leu Gly Asp Lys<br>            180                  185                  190 | 576 |
| CTC AAA AAT ATC GGT GGA CTT GAT AAA GCT GGC CTT GGT TTA GAT GTT<br>Leu Lys Asn Ile Gly Gly Leu Asp Lys Ala Gly Leu Gly Leu Asp Val<br>        195                  200                  205 | 624 |
| ATC TCA GGG CTA TTA TCG GGC GCA ACA GCT GCA CTT GTA CTT GCA GAT<br>Ile Ser Gly Leu Leu Ser Gly Ala Thr Ala Ala Leu Val Leu Ala Asp<br>210                  215                  220 | 672 |
| AAA AAT GCT TCA ACA GCT AAA AAA GTG GGT GCG GGT TTT GAA TTG GCA<br>Lys Asn Ala Ser Thr Ala Lys Lys Val Gly Ala Gly Phe Glu Leu Ala<br>225                  230                  235                  240 | 720 |
| AAC CAA GTT GTT GGT AAT ATT ACC AAA GCC GTT TCT TCT TAC ATT TTA<br>Asn Gln Val Val Gly Asn Ile Thr Lys Ala Val Ser Ser Tyr Ile Leu<br>                  245                  250                  255 | 768 |
| GCC CAA CGT GTT GCA GCA GGT TTA TCT TCA ACT GGG CCT GTG GCT GCT<br>Ala Gln Arg Val Ala Ala Gly Leu Ser Ser Thr Gly Pro Val Ala Ala<br>            260                  265                  270 | 816 |
| TTA ATT GCT TCT ACT GTT TCT CTT GCG ATT AGC CCA TTA GCA TTT GCC<br>Leu Ile Ala Ser Thr Val Ser Leu Ala Ile Ser Pro Leu Ala Phe Ala<br>275                  280                  285 | 864 |
| GGT ATT GCC GAT AAA TTT AAT CAT GCA AAA AGT TTA GAG AGT TAT GCC<br>Gly Ile Ala Asp Lys Phe Asn His Ala Lys Ser Leu Glu Ser Tyr Ala<br>        290                  295                  300 | 912 |
| GAA CGC TTT AAA AAA TTA GGC TAT GAC GGA GAT AAT TTA TTA GCA GAA<br>Glu Arg Phe Lys Lys Leu Gly Tyr Asp Gly Asp Asn Leu Leu Ala Glu<br>305                  310                  315                  320 | 960 |
| TAT CAG CGG GGA ACA GGG ACT ATT GAT GCA TCG GTT ACT GCA ATT AAT<br>Tyr Gln Arg Gly Thr Gly Thr Ile Asp Ala Ser Val Thr Ala Ile Asn<br>                  325                  330                  335 | 1008 |
| ACC GCA TTG GCC GCT ATT GCT GGT GGT GTG TCT GCT GCT GCA GCC GGC<br>Thr Ala Leu Ala Ala Ile Ala Gly Gly Val Ser Ala Ala Ala Ala Gly<br>            340                  345                  350 | 1056 |
| TCG GTT ATT GCT TCA CCG ATT GCC TTA TTA GTA TCT GGG ATT ACC GGT<br>Ser Val Ile Ala Ser Pro Ile Ala Leu Leu Val Ser Gly Ile Thr Gly<br>355                  360                  365 | 1104 |
| GTA ATT TCT ACG ATT CTG CAA TAT TCT AAA CAA GCA ATG TTT GAG CAC<br>Val Ile Ser Thr Ile Leu Gln Tyr Ser Lys Gln Ala Met Phe Glu His<br>        370                  375                  380 | 1152 |
| GTT GCA AAT AAA ATT CAT AAC AAA ATT GTA GAA TGG GAA AAA AAT AAT<br>Val Ala Asn Lys Ile His Asn Lys Ile Val Glu Trp Glu Lys Asn Asn<br>385                  390                  395                  400 | 1200 |
| CAC GGT AAG AAC TAC TTT GAA AAT GGT TAC GAT GCC CGT TAT CTT GCG<br>His Gly Lys Asn Tyr Phe Glu Asn Gly Tyr Asp Ala Arg Tyr Leu Ala<br>                  405                  410                  415 | 1248 |
| AAT TTA CAA GAT AAT ATG AAA TTC TTA CTG AAC TTA AAC AAA GAG TTA<br>Asn Leu Gln Asp Asn Met Lys Phe Leu Leu Asn Leu Asn Lys Glu Leu<br>            420                  425                  430 | 1296 |
| CAG GCA GAA CGT GTC ATC GCT ATT ACT CAG CAG CAA TGG GAT AAC AAC<br>Gln Ala Glu Arg Val Ile Ala Ile Thr Gln Gln Gln Trp Asp Asn Asn<br>435                  440                  445 | 1344 |
| ATT GGT GAT TTA GCT GGT ATT AGC CGT TTA GGT GAA AAA GTC CTT AGT<br>Ile Gly Asp Leu Ala Gly Ile Ser Arg Leu Gly Glu Lys Val Leu Ser<br>        450                  455                  460 | 1392 |
| GGT AAA GCC TAT GTG GAT GCG TTT GAA GAA GGC AAA CAC ATT AAA GCC<br>Gly Lys Ala Tyr Val Asp Ala Phe Glu Glu Gly Lys His Ile Lys Ala | 1440 |

```
                    465                 470                 475                 480
GAT AAA TTA GTA CAG TTG GAT TCG GCA AAC GGT ATT ATT GAT GTG AGT        1488
Asp Lys Leu Val Gln Leu Asp Ser Ala Asn Gly Ile Ile Asp Val Ser
                        485                 490                 495

AAT TCG GGT AAA GCG AAA ACT CAG CAT ATC TTA TTC AGA ACG CCA TTA        1536
Asn Ser Gly Lys Ala Lys Thr Gln His Ile Leu Phe Arg Thr Pro Leu
                500                 505                 510

TTG ACG CCG GGA ACA GAG CAT CGT GAA CGC GTA CAA ACA GGT AAA TAT        1584
Leu Thr Pro Gly Thr Glu His Arg Glu Arg Val Gln Thr Gly Lys Tyr
            515                 520                 525

GAA TAT ATT ACC AAG CTC AAT ATT AAC CGT GTA GAT AGC TGG AAA ATT        1632
Glu Tyr Ile Thr Lys Leu Asn Ile Asn Arg Val Asp Ser Trp Lys Ile
        530                 535                 540

ACA GAT GGT GCA GCA AGT TCT ACC TTT GAT TTA ACT AAC GTT GTT CAG        1680
Thr Asp Gly Ala Ala Ser Ser Thr Phe Asp Leu Thr Asn Val Val Gln
545                 550                 555                 560

CGT ATT GGT ATT GAA TTA GAC AAT GCT GGA AAT GTA ACT AAA ACC AAA        1728
Arg Ile Gly Ile Glu Leu Asp Asn Ala Gly Asn Val Thr Lys Thr Lys
                565                 570                 575

GAA ACA AAA ATT ATT GCC AAA CTT GGT GAA GGT GAT GAC AAC GTA TTT        1776
Glu Thr Lys Ile Ile Ala Lys Leu Gly Glu Gly Asp Asp Asn Val Phe
                580                 585                 590

GTT GGT TCT GGT ACG ACG GAA ATT GAT GGC GGT GAA GGT TAC GAC CGA        1824
Val Gly Ser Gly Thr Thr Glu Ile Asp Gly Gly Glu Gly Tyr Asp Arg
            595                 600                 605

GTT CAC TAT AGC CGT GGA AAC TAT GGT GCT TTA ACT ATT GAT GCA ACC        1872
Val His Tyr Ser Arg Gly Asn Tyr Gly Ala Leu Thr Ile Asp Ala Thr
        610                 615                 620

AAA GAG ACC GAG CAA GGT AGT TAT ACC GTA AAT CGT TTC GTA GAA ACC        1920
Lys Glu Thr Glu Gln Gly Ser Tyr Thr Val Asn Arg Phe Val Glu Thr
625                 630                 635                 640

GGT AAA GCA CTA CAC GAA GTG ACT TCA ACC CAT ACC GCA TTA GTG GGC        1968
Gly Lys Ala Leu His Glu Val Thr Ser Thr His Thr Ala Leu Val Gly
                645                 650                 655

AAC CGT GAA GAA AAA ATA GAA TAT CGT CAT AGC AAT AAC CAG CAC CAT        2016
Asn Arg Glu Glu Lys Ile Glu Tyr Arg His Ser Asn Asn Gln His His
                660                 665                 670

GCC GGT TAT TAC ACC AAA GAT ACC TTG AAA GCT GTT GAA GAA ATT ATC        2064
Ala Gly Tyr Tyr Thr Lys Asp Thr Leu Lys Ala Val Glu Glu Ile Ile
            675                 680                 685

GGT ACA TCA CAT AAC GAT ATC TTT AAA GGT AGT AAG TTC AAT GAT GCC        2112
Gly Thr Ser His Asn Asp Ile Phe Lys Gly Ser Lys Phe Asn Asp Ala
        690                 695                 700

TTT AAC GGT GGT GAT GGT GTC GAT ACT ATT GAC GGT AAC GAC GGC AAT        2160
Phe Asn Gly Gly Asp Gly Val Asp Thr Ile Asp Gly Asn Asp Gly Asn
705                 710                 715                 720

GAC CGC TTA TTT GGT GGT AAA GGC GAT GAT ATT CTC GAT GGT GGA AAT        2208
Asp Arg Leu Phe Gly Gly Lys Gly Asp Asp Ile Leu Asp Gly Gly Asn
                725                 730                 735

GGT GAT GAT TTT ATC GAT GGC GGT AAA GGC AAC GAC CTA TTA CAC GGT        2256
Gly Asp Asp Phe Ile Asp Gly Gly Lys Gly Asn Asp Leu Leu His Gly
                740                 745                 750

GGC AAG GGC GAT GAT ATT TTC GTT CAC CGT AAA GGC GAT GGT AAT GAT        2304
Gly Lys Gly Asp Asp Ile Phe Val His Arg Lys Gly Asp Gly Asn Asp
            755                 760                 765

ATT ATT ACC GAT TCT GAC GGC AAT GAT AAA TTA TCA TTC TCT GAT TCG        2352
Ile Ile Thr Asp Ser Asp Gly Asn Asp Lys Leu Ser Phe Ser Asp Ser
        770                 775                 780

AAC TTA AAA GAT TTA ACA TTT GAA AAA GTT AAA CAT AAT CTT GTC ATC        2400
```

```
                                                                -continued

Asn Leu Lys Asp Leu Thr Phe Glu Lys Val Lys His Asn Leu Val Ile
785                 790                 795                 800

ACG AAT AGC AAA AAA GAG AAA GTG ACC ATT CAA AAC TGG TTC CGA GAG       2448
Thr Asn Ser Lys Lys Glu Lys Val Thr Ile Gln Asn Trp Phe Arg Glu
                805                 810                 815

GCT GAT TTT GCT AAA GAA GTG CCT AAT TAT AAA GCA ACT AAA GAT GAG       2496
Ala Asp Phe Ala Lys Glu Val Pro Asn Tyr Lys Ala Thr Lys Asp Glu
                820                 825                 830

AAA ATC GAA GAA ATC ATC GGT CAA AAT GGC GAG CGG ATC ACC TCA AAG       2544
Lys Ile Glu Glu Ile Ile Gly Gln Asn Gly Glu Arg Ile Thr Ser Lys
                835                 840                 845

CAA GTT GAT GAT CTT ATC GCA AAA GGT AAC GGC AAA ATT ACC CAA GAT       2592
Gln Val Asp Asp Leu Ile Ala Lys Gly Asn Gly Lys Ile Thr Gln Asp
        850                 855                 860

GAG CTA TCA AAA GTT GTT GAT AAC TAT GAA TTG CTC AAA CAT AGC AAA       2640
Glu Leu Ser Lys Val Val Asp Asn Tyr Glu Leu Leu Lys His Ser Lys
865                 870                 875                 880

AAT GTG ACA AAC AGC TTA GAT AAG TTA ATC TCA TCT GTA AGT GCA TTT       2688
Asn Val Thr Asn Ser Leu Asp Lys Leu Ile Ser Ser Val Ser Ala Phe
                885                 890                 895

ACC TCG TCT AAT GAT TCG AGA AAT GTA TTA GTG GCT CCA ACT TCA ATG       2736
Thr Ser Ser Asn Asp Ser Arg Asn Val Leu Val Ala Pro Thr Ser Met
                900                 905                 910

TTG GAT CAA AGT TTA TCT TCT CTT CAA TTT GCT AGG GGA TCT CAG CAT       2784
Leu Asp Gln Ser Leu Ser Ser Leu Gln Phe Ala Arg Gly Ser Gln His
                915                 920                 925

TGG AGC TAC GGC CTG CGC CCT GGC TAAGGATCC                             2817
Trp Ser Tyr Gly Leu Arg Pro Gly
        930                 935

(2) INFORMATION FOR SEQ ID NO: 12:

(i) SEQUENCE CHARACTERISTICS:
        (A) LENGTH: 936 amino acids
        (B) TYPE: amino acid
        (D) TOPOLOGY: linear (ii) MOLECULE TYPE: protein (xi) SEQUENCE DESCRIPTION: SEQ ID NO: 12:

Met Ala Thr Val Ile Asp Leu Ser Phe Pro Lys Thr Gly Ala Lys Lys
1               5                   10                  15

Ile Ile Leu Tyr Ile Pro Gln Asn Tyr Gln Tyr Asp Thr Glu Gln Gly
            20                  25                  30

Asn Gly Leu Gln Asp Leu Val Lys Ala Ala Glu Glu Leu Gly Ile Glu
        35                  40                  45

Val Gln Arg Glu Glu Arg Asn Asn Ile Ala Thr Ala Gln Thr Ser Leu
    50                  55                  60

Gly Thr Ile Gln Thr Ala Ile Gly Leu Thr Glu Arg Gly Ile Val Leu
65                  70                  75                  80

Ser Ala Pro Gln Ile Asp Lys Leu Leu Gln Lys Thr Lys Ala Gly Gln
                85                  90                  95

Ala Leu Gly Ser Ala Glu Ser Ile Val Gln Asn Ala Asn Lys Ala Lys
            100                 105                 110

Thr Val Leu Ser Gly Ile Gln Ser Ile Leu Gly Ser Val Leu Ala Gly
        115                 120                 125

Met Asp Leu Asp Glu Ala Leu Gln Asn Asn Ser Asn Gln His Ala Leu
    130                 135                 140

Ala Lys Ala Gly Leu Glu Leu Thr Asn Ser Leu Ile Glu Asn Ile Ala
```

```
                        145                 150                 155                 160
Asn Ser Val Lys Thr Leu Asp Glu Phe Gly Glu Gln Ile Ser Gln Phe
                        165                 170                 175
Gly Ser Lys Leu Gln Asn Ile Lys Gly Leu Gly Thr Leu Gly Asp Lys
            180                 185                 190
Leu Lys Asn Ile Gly Gly Leu Asp Lys Ala Gly Leu Gly Leu Asp Val
        195                 200                 205
Ile Ser Gly Leu Leu Ser Gly Ala Thr Ala Ala Leu Val Leu Ala Asp
    210                 215                 220
Lys Asn Ala Ser Thr Ala Lys Lys Val Gly Ala Gly Phe Glu Leu Ala
225                 230                 235                 240
Asn Gln Val Val Gly Asn Ile Thr Lys Ala Val Ser Ser Tyr Ile Leu
                245                 250                 255
Ala Gln Arg Val Ala Ala Gly Leu Ser Ser Thr Gly Pro Val Ala Ala
            260                 265                 270
Leu Ile Ala Ser Thr Val Ser Leu Ala Ile Ser Pro Leu Ala Phe Ala
        275                 280                 285
Gly Ile Ala Asp Lys Phe Asn His Ala Lys Ser Leu Glu Ser Tyr Ala
    290                 295                 300
Glu Arg Phe Lys Lys Leu Gly Tyr Asp Gly Asp Asn Leu Leu Ala Glu
305                 310                 315                 320
Tyr Gln Arg Gly Thr Gly Thr Ile Asp Ala Ser Val Thr Ala Ile Asn
                325                 330                 335
Thr Ala Leu Ala Ala Ile Ala Gly Gly Val Ser Ala Ala Ala Ala Gly
            340                 345                 350
Ser Val Ile Ala Ser Pro Ile Ala Leu Leu Val Ser Gly Ile Thr Gly
        355                 360                 365
Val Ile Ser Thr Ile Leu Gln Tyr Ser Lys Gln Ala Met Phe Glu His
    370                 375                 380
Val Ala Asn Lys Ile His Asn Lys Ile Val Glu Trp Glu Lys Asn Asn
385                 390                 395                 400
His Gly Lys Asn Tyr Phe Glu Asn Gly Tyr Asp Ala Arg Tyr Leu Ala
                405                 410                 415
Asn Leu Gln Asp Asn Met Lys Phe Leu Leu Asn Leu Asn Lys Glu Leu
            420                 425                 430
Gln Ala Glu Arg Val Ile Ala Ile Thr Gln Gln Trp Asp Asn Asn
        435                 440                 445
Ile Gly Asp Leu Ala Gly Ile Ser Arg Leu Gly Glu Lys Val Leu Ser
    450                 455                 460
Gly Lys Ala Tyr Val Asp Ala Phe Glu Glu Gly Lys His Ile Lys Ala
465                 470                 475                 480
Asp Lys Leu Val Gln Leu Asp Ser Ala Asn Gly Ile Ile Asp Val Ser
                485                 490                 495
Asn Ser Gly Lys Ala Lys Thr Gln His Ile Leu Phe Arg Thr Pro Leu
            500                 505                 510
Leu Thr Pro Gly Thr Glu His Arg Glu Arg Val Gln Thr Gly Lys Tyr
        515                 520                 525
Glu Tyr Ile Thr Lys Leu Asn Ile Asn Arg Val Asp Ser Trp Lys Ile
    530                 535                 540
Thr Asp Gly Ala Ala Ser Ser Thr Phe Asp Leu Thr Asn Val Val Gln
545                 550                 555                 560
Arg Ile Gly Ile Glu Leu Asp Asn Ala Gly Asn Val Thr Lys Thr Lys
                565                 570                 575
```

```
Glu Thr Lys Ile Ile Ala Lys Leu Gly Glu Gly Asp Asp Asn Val Phe
            580                 585                 590
Val Gly Ser Gly Thr Thr Glu Ile Asp Gly Gly Glu Gly Tyr Asp Arg
        595                 600                 605
Val His Tyr Ser Arg Gly Asn Tyr Gly Ala Leu Thr Ile Asp Ala Thr
    610                 615                 620
Lys Glu Thr Glu Gln Gly Ser Tyr Thr Val Asn Arg Phe Val Glu Thr
625                 630                 635                 640
Gly Lys Ala Leu His Glu Val Thr Ser Thr His Thr Ala Leu Val Gly
                645                 650                 655
Asn Arg Glu Glu Lys Ile Glu Tyr Arg His Ser Asn Asn Gln His His
            660                 665                 670
Ala Gly Tyr Tyr Thr Lys Asp Thr Leu Lys Ala Val Glu Glu Ile Ile
        675                 680                 685
Gly Thr Ser His Asn Asp Ile Phe Lys Gly Ser Lys Phe Asn Asp Ala
    690                 695                 700
Phe Asn Gly Gly Asp Gly Val Asp Thr Ile Asp Gly Asn Asp Gly Asn
705                 710                 715                 720
Asp Arg Leu Phe Gly Gly Lys Gly Asp Asp Ile Leu Asp Gly Gly Asn
                725                 730                 735
Gly Asp Asp Phe Ile Asp Gly Gly Lys Gly Asn Asp Leu Leu His Gly
            740                 745                 750
Gly Lys Gly Asp Asp Ile Phe Val His Arg Lys Gly Asp Gly Asn Asp
        755                 760                 765
Ile Ile Thr Asp Ser Asp Gly Asn Asp Lys Leu Ser Phe Ser Asp Ser
    770                 775                 780
Asn Leu Lys Asp Leu Thr Phe Glu Lys Val Lys His Asn Leu Val Ile
785                 790                 795                 800
Thr Asn Ser Lys Lys Glu Lys Val Thr Ile Gln Asn Trp Phe Arg Glu
                805                 810                 815
Ala Asp Phe Ala Lys Glu Val Pro Asn Tyr Lys Ala Thr Lys Asp Glu
            820                 825                 830
Lys Ile Glu Glu Ile Ile Gly Gln Asn Gly Glu Arg Ile Thr Ser Lys
        835                 840                 845
Gln Val Asp Asp Leu Ile Ala Lys Gly Asn Gly Lys Ile Thr Gln Asp
    850                 855                 860
Glu Leu Ser Lys Val Val Asp Asn Tyr Glu Leu Leu Lys His Ser Lys
865                 870                 875                 880
Asn Val Thr Asn Ser Leu Asp Lys Leu Ile Ser Ser Val Ser Ala Phe
                885                 890                 895
Thr Ser Ser Asn Asp Ser Arg Asn Val Leu Val Ala Pro Thr Ser Met
            900                 905                 910
Leu Asp Gln Ser Leu Ser Ser Leu Gln Phe Ala Arg Gly Ser Gln His
        915                 920                 925
Trp Ser Tyr Gly Leu Arg Pro Gly
    930                 935

(2) INFORMATION FOR SEQ ID NO: 13:

(i) SEQUENCE CHARACTERISTICS:
        (A) LENGTH: 2861 base pairs
        (B) TYPE: nucleic acid
        (C) STRANDEDNESS: double
        (D) TOPOLOGY: linear
```

-continued (ii) MOLECULE TYPE: DNA (genomic)

(ix) FEATURE:
    (A) NAME/KEY: CDS
    (B) LOCATION: 1..2853

(xi) SEQUENCE DESCRIPTION: SEQ ID NO: 13:

```
ATG GCT ACT GTT ATA GAT CTA AGC TTC CCA AAA ACT GGG GCA AAA AAA      48
Met Ala Thr Val Ile Asp Leu Ser Phe Pro Lys Thr Gly Ala Lys Lys
 1               5                  10                  15

ATT ATC CTC TAT ATT CCC CAA AAT TAC CAA TAT GAT ACT GAA CAA GGT      96
Ile Ile Leu Tyr Ile Pro Gln Asn Tyr Gln Tyr Asp Thr Glu Gln Gly
                20                  25                  30

AAT GGT TTA CAG GAT TTA GTC AAA GCG GCC GAA GAG TTG GGG ATT GAG     144
Asn Gly Leu Gln Asp Leu Val Lys Ala Ala Glu Glu Leu Gly Ile Glu
             35                  40                  45

GTA CAA AGA GAA GAA CGC AAT AAT ATT GCA ACA GCT CAA ACC AGT TTA     192
Val Gln Arg Glu Glu Arg Asn Asn Ile Ala Thr Ala Gln Thr Ser Leu
         50                  55                  60

GGC ACG ATT CAA ACC GCT ATT GGC TTA ACT GAG CGT GGC ATT GTG TTA     240
Gly Thr Ile Gln Thr Ala Ile Gly Leu Thr Glu Arg Gly Ile Val Leu
 65                  70                  75                  80

TCC GCT CCA CAA ATT GAT AAA TTG CTA CAG AAA ACT AAA GCA GGC CAA     288
Ser Ala Pro Gln Ile Asp Lys Leu Leu Gln Lys Thr Lys Ala Gly Gln
                 85                  90                  95

GCA TTA GGT TCT GCC GAA AGC ATT GTA CAA AAT GCA AAT AAA GCC AAA     336
Ala Leu Gly Ser Ala Glu Ser Ile Val Gln Asn Ala Asn Lys Ala Lys
                100                 105                 110

ACT GTA TTA TCT GGC ATT CAA TCT ATT TTA GGC TCA GTA TTG GCT GGA     384
Thr Val Leu Ser Gly Ile Gln Ser Ile Leu Gly Ser Val Leu Ala Gly
            115                 120                 125

ATG GAT TTA GAT GAG GCC TTA CAG AAT AAC AGC AAC CAA CAT GCT CTT     432
Met Asp Leu Asp Glu Ala Leu Gln Asn Asn Ser Asn Gln His Ala Leu
130                 135                 140

GCT AAA GCT GGC TTG GAG CTA ACA AAT TCA TTA ATT GAA AAT ATT GCT     480
Ala Lys Ala Gly Leu Glu Leu Thr Asn Ser Leu Ile Glu Asn Ile Ala
145                 150                 155                 160

AAT TCA GTA AAA ACA CTT GAC GAA TTT GGT GAG CAA ATT AGT CAA TTT     528
Asn Ser Val Lys Thr Leu Asp Glu Phe Gly Glu Gln Ile Ser Gln Phe
                165                 170                 175

GGT TCA AAA CTA CAA AAT ATC AAA GGC TTA GGG ACT TTA GGA GAC AAA     576
Gly Ser Lys Leu Gln Asn Ile Lys Gly Leu Gly Thr Leu Gly Asp Lys
            180                 185                 190

CTC AAA AAT ATC GGT GGA CTT GAT AAA GCT GGC CTT GGT TTA GAT GTT     624
Leu Lys Asn Ile Gly Gly Leu Asp Lys Ala Gly Leu Gly Leu Asp Val
        195                 200                 205

ATC TCA GGG CTA TTA TCG GGC GCA ACA GCT GCA CTT GTA CTT GCA GAT     672
Ile Ser Gly Leu Leu Ser Gly Ala Thr Ala Ala Leu Val Leu Ala Asp
210                 215                 220

AAA AAT GCT TCA ACA GCT AAA AAA GTG GGT GCG GGT TTT GAA TTG GCA     720
Lys Asn Ala Ser Thr Ala Lys Lys Val Gly Ala Gly Phe Glu Leu Ala
225                 230                 235                 240

AAC CAA GTT GTT GGT AAT ATT ACC AAA GCC GTT TCT TCT TAC ATT TTA     768
Asn Gln Val Val Gly Asn Ile Thr Lys Ala Val Ser Ser Tyr Ile Leu
                245                 250                 255

GCC CAA CGT GTT GCA GCA GGT TTA TCT TCA ACT GGG CCT GTG GCT GCT     816
Ala Gln Arg Val Ala Ala Gly Leu Ser Ser Thr Gly Pro Val Ala Ala
            260                 265                 270

TTA ATT GCT TCT ACT GTT TCT CTT GCG ATT AGC CCA TTA GCA TTT GCC     864
Leu Ile Ala Ser Thr Val Ser Leu Ala Ile Ser Pro Leu Ala Phe Ala
        275                 280                 285
```

-continued

```
GGT ATT GCC GAT AAA TTT AAT CAT GCA AAA AGT TTA GAG AGT TAT GCC         912
Gly Ile Ala Asp Lys Phe Asn His Ala Lys Ser Leu Glu Ser Tyr Ala
    290                 295                 300

GAA CGC TTT AAA AAA TTA GGC TAT GAC GGA GAT AAT TTA TTA GCA GAA         960
Glu Arg Phe Lys Lys Leu Gly Tyr Asp Gly Asp Asn Leu Leu Ala Glu
305                 310                 315                 320

TAT CAG CGG GGA ACA GGG ACT ATT GAT GCA TCG GTT ACT GCA ATT AAT        1008
Tyr Gln Arg Gly Thr Gly Thr Ile Asp Ala Ser Val Thr Ala Ile Asn
                325                 330                 335

ACC GCA TTG GCC GCT ATT GCT GGT GGT GTG TCT GCT GCT GCA GCC GGC        1056
Thr Ala Leu Ala Ala Ile Ala Gly Gly Val Ser Ala Ala Ala Ala Gly
            340                 345                 350

TCG GTT ATT GCT TCA CCG ATT GCC TTA TTA GTA TCT GGG ATT ACC GGT        1104
Ser Val Ile Ala Ser Pro Ile Ala Leu Leu Val Ser Gly Ile Thr Gly
        355                 360                 365

GTA ATT TCT ACG ATT CTG CAA TAT TCT AAA CAA GCA ATG TTT GAG CAC        1152
Val Ile Ser Thr Ile Leu Gln Tyr Ser Lys Gln Ala Met Phe Glu His
    370                 375                 380

GTT GCA AAT AAA ATT CAT AAC AAA ATT GTA GAA TGG GAA AAA AAT AAT        1200
Val Ala Asn Lys Ile His Asn Lys Ile Val Glu Trp Glu Lys Asn Asn
385                 390                 395                 400

CAC GGT AAG AAC TAC TTT GAA AAT GGT TAC GAT GCC CGT TAT CTT GCG        1248
His Gly Lys Asn Tyr Phe Glu Asn Gly Tyr Asp Ala Arg Tyr Leu Ala
                405                 410                 415

AAT TTA CAA GAT AAT ATG AAA TTC TTA CTG AAC TTA AAC AAA GAG TTA        1296
Asn Leu Gln Asp Asn Met Lys Phe Leu Leu Asn Leu Asn Lys Glu Leu
            420                 425                 430

CAG GCA GAA CGT GTC ATC GCT ATT ACT CAG CAG CAA TGG GAT AAC AAC        1344
Gln Ala Glu Arg Val Ile Ala Ile Thr Gln Gln Gln Trp Asp Asn Asn
        435                 440                 445

ATT GGT GAT TTA GCT GGT ATT AGC CGT TTA GGT GAA AAA GTC CTT AGT        1392
Ile Gly Asp Leu Ala Gly Ile Ser Arg Leu Gly Glu Lys Val Leu Ser
    450                 455                 460

GGT AAA GCC TAT GTG GAT GCG TTT GAA GAA GGC AAA CAC ATT AAA GCC        1440
Gly Lys Ala Tyr Val Asp Ala Phe Glu Glu Gly Lys His Ile Lys Ala
465                 470                 475                 480

GAT AAA TTA GTA CAG TTG GAT TCG GCA AAC GGT ATT ATT GAT GTG AGT        1488
Asp Lys Leu Val Gln Leu Asp Ser Ala Asn Gly Ile Ile Asp Val Ser
                485                 490                 495

AAT TCG GGT AAA GCG AAA ACT CAG CAT ATC TTA TTC AGA ACG CCA TTA        1536
Asn Ser Gly Lys Ala Lys Thr Gln His Ile Leu Phe Arg Thr Pro Leu
            500                 505                 510

TTG ACG CCG GGA ACA GAG CAT CGT GAA CGC GTA CAA ACA GGT AAA TAT        1584
Leu Thr Pro Gly Thr Glu His Arg Glu Arg Val Gln Thr Gly Lys Tyr
        515                 520                 525

GAA TAT ATT ACC AAG CTC AAT ATT AAC CGT GTA GAT AGC TGG AAA ATT        1632
Glu Tyr Ile Thr Lys Leu Asn Ile Asn Arg Val Asp Ser Trp Lys Ile
    530                 535                 540

ACA GAT GGT GCA GCA AGT TCT ACC TTT GAT TTA ACT AAC GTT GTT CAG        1680
Thr Asp Gly Ala Ala Ser Ser Thr Phe Asp Leu Thr Asn Val Val Gln
545                 550                 555                 560

CGT ATT GGT ATT GAA TTA GAC AAT GCT GGA AAT GTA ACT AAA ACC AAA        1728
Arg Ile Gly Ile Glu Leu Asp Asn Ala Gly Asn Val Thr Lys Thr Lys
                565                 570                 575

GAA ACA AAA ATT ATT GCC AAA CTT GGT GAA GGT GAT GAC AAC GTA TTT        1776
Glu Thr Lys Ile Ile Ala Lys Leu Gly Glu Gly Asp Asp Asn Val Phe
            580                 585                 590

GTT GGT TCT GGT ACG ACG GAA ATT GAT GGC GGT GAA GGT TAC GAC CGA        1824
Val Gly Ser Gly Thr Thr Glu Ile Asp Gly Gly Glu Gly Tyr Asp Arg
```

-continued

|  |  |  |  |  |  |  |  | 595 |  |  |  |  |  | 600 |  |  |  |  |  | 605 |  |  |  |  |  |  |
| --- |

```
GTT CAC TAT AGC CGT GGA AAC TAT GGT GCT TTA ACT ATT GAT GCA ACC      1872
Val His Tyr Ser Arg Gly Asn Tyr Gly Ala Leu Thr Ile Asp Ala Thr
    610             615                 620

AAA GAG ACC GAG CAA GGT AGT TAT ACC GTA AAT CGT TTC GTA GAA ACC      1920
Lys Glu Thr Glu Gln Gly Ser Tyr Thr Val Asn Arg Phe Val Glu Thr
625             630                 635                 640

GGT AAA GCA CTA CAC GAA GTG ACT TCA ACC CAT ACC GCA TTA GTG GGC      1968
Gly Lys Ala Leu His Glu Val Thr Ser Thr His Thr Ala Leu Val Gly
                645                 650                 655

AAC CGT GAA GAA AAA ATA GAA TAT CGT CAT AGC AAT AAC CAG CAC CAT      2016
Asn Arg Glu Glu Lys Ile Glu Tyr Arg His Ser Asn Asn Gln His His
            660                 665                 670

GCC GGT TAT TAC ACC AAA GAT ACC TTG AAA GCT GTT GAA GAA ATT ATC      2064
Ala Gly Tyr Tyr Thr Lys Asp Thr Leu Lys Ala Val Glu Glu Ile Ile
        675                 680                 685

GGT ACA TCA CAT AAC GAT ATC TTT AAA GGT AGT AAG TTC AAT GAT GCC      2112
Gly Thr Ser His Asn Asp Ile Phe Lys Gly Ser Lys Phe Asn Asp Ala
    690                 695                 700

TTT AAC GGT GGT GAT GGT GTC GAT ACT ATT GAC GGT AAC GAC GGC AAT      2160
Phe Asn Gly Gly Asp Gly Val Asp Thr Ile Asp Gly Asn Asp Gly Asn
705                 710                 715                 720

GAC CGC TTA TTT GGT GGT AAA GGC GAT GAT ATT CTC GAT GGT GGA AAT      2208
Asp Arg Leu Phe Gly Gly Lys Gly Asp Asp Ile Leu Asp Gly Gly Asn
                725                 730                 735

GGT GAT GAT TTT ATC GAT GGC GGT AAA GGC AAC GAC CTA TTA CAC GGT      2256
Gly Asp Asp Phe Ile Asp Gly Gly Lys Gly Asn Asp Leu Leu His Gly
            740                 745                 750

GGC AAG GGC GAT GAT ATT TTC GTT CAC CGT AAA GGC GAT GGT AAT GAT      2304
Gly Lys Gly Asp Asp Ile Phe Val His Arg Lys Gly Asp Gly Asn Asp
        755                 760                 765

ATT ATT ACC GAT TCT GAC GGC AAT GAT AAA TTA TCA TTC TCT GAT TCG      2352
Ile Ile Thr Asp Ser Asp Gly Asn Asp Lys Leu Ser Phe Ser Asp Ser
    770                 775                 780

AAC TTA AAA GAT TTA ACA TTT GAA AAA GTT AAA CAT AAT CTT GTC ATC      2400
Asn Leu Lys Asp Leu Thr Phe Glu Lys Val Lys His Asn Leu Val Ile
785                 790                 795                 800

ACG AAT AGC AAA AAA GAG AAA GTG ACC ATT CAA AAC TGG TTC CGA GAG      2448
Thr Asn Ser Lys Lys Glu Lys Val Thr Ile Gln Asn Trp Phe Arg Glu
                805                 810                 815

GCT GAT TTT GCT AAA GAA GTG CCT AAT TAT AAA GCA ACT AAA GAT GAG      2496
Ala Asp Phe Ala Lys Glu Val Pro Asn Tyr Lys Ala Thr Lys Asp Glu
            820                 825                 830

AAA ATC GAA GAA ATC ATC GGT CAA AAT GGC GAG CGG ATC ACC TCA AAG      2544
Lys Ile Glu Glu Ile Ile Gly Gln Asn Gly Glu Arg Ile Thr Ser Lys
        835                 840                 845

CAA GTT GAT GAT CTT ATC GCA AAA GGT AAC GGC AAA ATT ACC CAA GAT      2592
Gln Val Asp Asp Leu Ile Ala Lys Gly Asn Gly Lys Ile Thr Gln Asp
    850                 855                 860

GAG CTA TCA AAA GTT GTT GAT AAC TAT GAA TTG CTC AAA CAT AGC AAA      2640
Glu Leu Ser Lys Val Val Asp Asn Tyr Glu Leu Leu Lys His Ser Lys
865                 870                 875                 880

AAT GTG ACA AAC AGC TTA GAT AAG TTA ATC TCA TCT GTA AGT GCA TTT      2688
Asn Val Thr Asn Ser Leu Asp Lys Leu Ile Ser Ser Val Ser Ala Phe
                885                 890                 895

ACC TCG TCT AAT GAT TCG AGA AAT GTA TTA GTG GCT CCA ACT TCA ATG      2736
Thr Ser Ser Asn Asp Ser Arg Asn Val Leu Val Ala Pro Thr Ser Met
            900                 905                 910

TTG GAT CAA AGT TTA TCT TCT CTT CAA TTT GCT AGG GGA TCT TGC AAC      2784
```

```
Leu Asp Gln Ser Leu Ser Ser Leu Gln Phe Ala Arg Gly Ser Cys Asn
        915                 920                 925

ATT GTG CCT GTG AGC ATT GTG AGC CGC AAC ATT GTG TAC ACC CGC GCG      2832
Ile Val Pro Val Ser Ile Val Ser Arg Asn Ile Val Tyr Thr Arg Ala
        930                 935                 940

CAA CCT AAC CAA GAC ATT GTG TAGGATCC                                 2861
Gln Pro Asn Gln Asp Ile Val
945                 950
```

(2) INFORMATION FOR SEQ ID NO: 14:

(i) SEQUENCE CHARACTERISTICS:
        (A) LENGTH: 951 amino acids
        (B) TYPE: amino acid
        (D) TOPOLOGY: linear (ii) MOLECULE TYPE: protein (xi) SEQUENCE DESCRIPTION: SEQ ID NO: 14:

```
Met Ala Thr Val Ile Asp Leu Ser Phe Pro Lys Thr Gly Ala Lys Lys
 1               5                  10                  15

Ile Ile Leu Tyr Ile Pro Gln Asn Tyr Gln Tyr Asp Thr Glu Gln Gly
            20                  25                  30

Asn Gly Leu Gln Asp Leu Val Lys Ala Ala Glu Glu Leu Gly Ile Glu
        35                  40                  45

Val Gln Arg Glu Glu Arg Asn Asn Ile Ala Thr Ala Gln Thr Ser Leu
    50                  55                  60

Gly Thr Ile Gln Thr Ala Ile Gly Leu Thr Glu Arg Gly Ile Val Leu
65                  70                  75                  80

Ser Ala Pro Gln Ile Asp Lys Leu Leu Gln Lys Thr Lys Ala Gly Gln
                85                  90                  95

Ala Leu Gly Ser Ala Glu Ser Ile Val Gln Asn Ala Asn Lys Ala Lys
            100                 105                 110

Thr Val Leu Ser Gly Ile Gln Ser Ile Leu Gly Ser Val Leu Ala Gly
        115                 120                 125

Met Asp Leu Asp Glu Ala Leu Gln Asn Asn Ser Asn Gln His Ala Leu
130                 135                 140

Ala Lys Ala Gly Leu Glu Leu Thr Asn Ser Leu Ile Glu Asn Ile Ala
145                 150                 155                 160

Asn Ser Val Lys Thr Leu Asp Glu Phe Gly Glu Gln Ile Ser Gln Phe
                165                 170                 175

Gly Ser Lys Leu Gln Asn Ile Lys Gly Leu Gly Thr Leu Gly Asp Lys
            180                 185                 190

Leu Lys Asn Ile Gly Gly Leu Asp Lys Ala Gly Leu Gly Leu Asp Val
        195                 200                 205

Ile Ser Gly Leu Leu Ser Gly Ala Thr Ala Ala Leu Val Leu Ala Asp
    210                 215                 220

Lys Asn Ala Ser Thr Ala Lys Lys Val Gly Ala Gly Phe Glu Leu Ala
225                 230                 235                 240

Asn Gln Val Val Gly Asn Ile Thr Lys Ala Val Ser Ser Tyr Ile Leu
                245                 250                 255

Ala Gln Arg Val Ala Ala Gly Leu Ser Ser Thr Gly Pro Val Ala Ala
            260                 265                 270

Leu Ile Ala Ser Thr Val Ser Leu Ala Ile Ser Pro Leu Ala Phe Ala
        275                 280                 285

Gly Ile Ala Asp Lys Phe Asn His Ala Lys Ser Leu Glu Ser Tyr Ala
    290                 295                 300
```

```
Glu Arg Phe Lys Lys Leu Gly Tyr Asp Gly Asp Asn Leu Leu Ala Glu
305                 310                 315                 320

Tyr Gln Arg Gly Thr Gly Thr Ile Asp Ala Ser Val Thr Ala Ile Asn
                325                 330                 335

Thr Ala Leu Ala Ala Ile Ala Gly Gly Val Ser Ala Ala Ala Ala Gly
            340                 345                 350

Ser Val Ile Ala Ser Pro Ile Ala Leu Leu Val Ser Gly Ile Thr Gly
        355                 360                 365

Val Ile Ser Thr Ile Leu Gln Tyr Ser Lys Gln Ala Met Phe Glu His
    370                 375                 380

Val Ala Asn Lys Ile His Asn Lys Ile Val Glu Trp Glu Lys Asn Asn
385                 390                 395                 400

His Gly Lys Asn Tyr Phe Glu Asn Gly Tyr Asp Ala Arg Tyr Leu Ala
                405                 410                 415

Asn Leu Gln Asp Asn Met Lys Phe Leu Leu Asn Leu Asn Lys Glu Leu
            420                 425                 430

Gln Ala Glu Arg Val Ile Ala Ile Thr Gln Gln Trp Asp Asn Asn
        435                 440                 445

Ile Gly Asp Leu Ala Gly Ile Ser Arg Leu Gly Glu Lys Val Leu Ser
    450                 455                 460

Gly Lys Ala Tyr Val Asp Ala Phe Glu Glu Gly Lys His Ile Lys Ala
465                 470                 475                 480

Asp Lys Leu Val Gln Leu Asp Ser Ala Asn Gly Ile Ile Asp Val Ser
                485                 490                 495

Asn Ser Gly Lys Ala Lys Thr Gln His Ile Leu Phe Arg Thr Pro Leu
            500                 505                 510

Leu Thr Pro Gly Thr Glu His Arg Glu Arg Val Gln Thr Gly Lys Tyr
        515                 520                 525

Glu Tyr Ile Thr Lys Leu Asn Ile Asn Arg Val Asp Ser Trp Lys Ile
    530                 535                 540

Thr Asp Gly Ala Ala Ser Ser Thr Phe Asp Leu Thr Asn Val Val Gln
545                 550                 555                 560

Arg Ile Gly Ile Glu Leu Asp Asn Ala Gly Asn Val Thr Lys Thr Lys
                565                 570                 575

Glu Thr Lys Ile Ile Ala Lys Leu Gly Glu Gly Asp Asp Asn Val Phe
            580                 585                 590

Val Gly Ser Gly Thr Thr Glu Ile Asp Gly Gly Glu Gly Tyr Asp Arg
        595                 600                 605

Val His Tyr Ser Arg Gly Asn Tyr Gly Ala Leu Thr Ile Asp Ala Thr
    610                 615                 620

Lys Glu Thr Glu Gln Gly Ser Tyr Thr Val Asn Arg Phe Val Glu Thr
625                 630                 635                 640

Gly Lys Ala Leu His Glu Val Thr Ser Thr His Thr Ala Leu Val Gly
                645                 650                 655

Asn Arg Glu Glu Lys Ile Glu Tyr Arg His Ser Asn Asn Gln His His
            660                 665                 670

Ala Gly Tyr Tyr Thr Lys Asp Thr Leu Lys Ala Val Glu Glu Ile Ile
        675                 680                 685

Gly Thr Ser His Asn Asp Ile Phe Lys Gly Ser Lys Phe Asn Asp Ala
    690                 695                 700

Phe Asn Gly Gly Asp Gly Val Asp Thr Ile Asp Gly Asn Asp Gly Asn
705                 710                 715                 720
```

```
Asp Arg Leu Phe Gly Gly Lys Gly Asp Ile Leu Asp Gly Gly Asn
            725                 730                 735
Gly Asp Asp Phe Ile Asp Gly Gly Lys Gly Asn Asp Leu Leu His Gly
            740                 745                 750
Gly Lys Gly Asp Asp Ile Phe Val His Arg Lys Gly Asp Gly Asn Asp
            755                 760                 765
Ile Ile Thr Asp Ser Asp Gly Asn Asp Lys Leu Ser Phe Ser Asp Ser
            770                 775                 780
Asn Leu Lys Asp Leu Thr Phe Glu Lys Val Lys His Asn Leu Val Ile
785                 790                 795                 800
Thr Asn Ser Lys Lys Glu Lys Val Thr Ile Gln Asn Trp Phe Arg Glu
                    805                 810                 815
Ala Asp Phe Ala Lys Glu Val Pro Asn Tyr Lys Ala Thr Lys Asp Glu
                    820                 825                 830
Lys Ile Glu Glu Ile Ile Gly Gln Asn Gly Glu Arg Ile Thr Ser Lys
                    835                 840                 845
Gln Val Asp Asp Leu Ile Ala Lys Gly Asn Gly Lys Ile Thr Gln Asp
850                 855                 860
Glu Leu Ser Lys Val Val Asp Asn Tyr Glu Leu Leu Lys His Ser Lys
865                 870                 875                 880
Asn Val Thr Asn Ser Leu Asp Lys Leu Ile Ser Ser Val Ser Ala Phe
                    885                 890                 895
Thr Ser Ser Asn Asp Ser Arg Asn Val Leu Val Ala Pro Thr Ser Met
                    900                 905                 910
Leu Asp Gln Ser Leu Ser Ser Leu Gln Phe Ala Arg Gly Ser Cys Asn
                    915                 920                 925
Ile Val Pro Val Ser Ile Val Ser Arg Asn Ile Val Tyr Thr Arg Ala
                    930                 935                 940
Gln Pro Asn Gln Asp Ile Val
945                 950

(2) INFORMATION FOR SEQ ID NO: 15:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /note= "The amino acid at this
            location can be either Lys, Asp, Val or Asn."

(ix) FEATURE:
        (A) NAME/KEY: Modified-site
        (B) LOCATION: 5
        (D) OTHER INFORMATION: /note= "The amino acid at this
            location can be either Lys, Asp, Val or Asn."

(xi) SEQUENCE DESCRIPTION: SEQ ID NO: 15:

Gly Gly Xaa Gly Xaa Asp
1                   5
```

What is claimed is:

1. A chimeric protein comprising an antigen coupled to a carrier protein, wherein said carrier protein is a leukotoxin polypeptide that activates helper T-cells and said antigen is a selected peptide hormone which is not a cytokine, and further wherein said leukotoxin polypeptide is an RTX leukotoxin from a bacterium selected from the group consisting of *Pasteurella haemolytica, E. coli* and *Actinobacillus pleuropneumoniae.*

2. The chimeric protein of claim 1, wherein said leukotoxin polypeptide is coupled to gonadotropin releasing hormone (GnRH) or an epitope thereof.

3. The chimeric protein of claim 2, comprising the amino acid sequence of SEQ ID NO:12.

4. The chimeric protein of claim 1, wherein the leukotoxin polypeptide is a *Pasteurella haemolytica* leukotoxin polypeptide.

5. The chimeric protein of claim 2, wherein the leukotoxin polypeptide is a *Pasteurella haemolytica* leukotoxin polypeptide.

* * * * *